United States Patent
Pajon Feyt

(10) Patent No.: US 9,260,489 B2
(45) Date of Patent: Feb. 16, 2016

(54) **ENGINEERED SEQUENCES TO FACILITATE EXPRESSION OF ANTIGENS IN *NEISSERIA* AND METHODS OF USE**

(75) Inventor: Rolando Pajon Feyt, Novato, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 0 days.

(21) Appl. No.: 14/239,072

(22) PCT Filed: Aug. 30, 2012

(86) PCT No.: PCT/US2012/053142
§ 371 (c)(1),
(2), (4) Date: Apr. 4, 2014

(87) PCT Pub. No.: WO2013/033398
PCT Pub. Date: Mar. 7, 2013

(65) Prior Publication Data
US 2014/0220632 A1 Aug. 7, 2014

Related U.S. Application Data

(60) Provisional application No. 61/529,776, filed on Aug. 31, 2011.

(51) Int. Cl.
*C07K 14/22* (2006.01)
*A61K 39/095* (2006.01)
*C07K 14/195* (2006.01)
*C12N 15/74* (2006.01)

(52) U.S. Cl.
CPC ............... *C07K 14/22* (2013.01); *A61K 39/095* (2013.01); *C07K 14/195* (2013.01); *C12N 15/74* (2013.01)

(58) Field of Classification Search
None
See application file for complete search history.

(56) References Cited

U.S. PATENT DOCUMENTS

| | | |
|---|---|---|
| 2007/0026021 A1 | 2/2007 | Fraser et al. |
| 2009/0035328 A1 | 2/2009 | Granoff |
| 2009/0117147 A1 | 5/2009 | Berthet et al. |
| 2009/0155913 A1 | 6/2009 | Barrangou et al. |
| 2011/0182942 A1 | 7/2011 | Zollinger et al. |

FOREIGN PATENT DOCUMENTS

| | | |
|---|---|---|
| WO | 9957280 | 11/1999 |
| WO | 0134642 | 5/2001 |
| WO | 0164922 | 9/2001 |
| WO | 0209746 | 2/2002 |
| WO | 2004048404 | 6/2004 |
| WO | 2010025964 | 3/2010 |

OTHER PUBLICATIONS

Van Der Ende et al. Multiple Mechanisms of Phase Variation of PorA in *Neisseria meningitides*. Infect mmun 68(12): 6685-90. Dec. 2000.*
van den Ende et al., Infection and Immunity, 2000, vol. 68 pp. 6685-6690.*
Sawaya, R. et al., (1999) "Mutational analysis of the promoter region of the pow A gene of *Neisseria meningitidis*", Gene Elsevier Amsterdam NL, 233(1-2):49-57.
Van Der Ende, A. et al, (1995) "Variable expression of class 1 outer membrane protein in *Neisseria meningitidis* is caused by variation in the spacing between the −10 and −35 regions of the promoter", Journal of Bacteriology, 177 (9):2475-2480.
Koeberling, Oliver, et al. (2009) "Meningococcal Outer Membrane Vesicle Vaccines Derived from Mutant Strains Engineered to Express Factor H Binding Proteins from Antigenic Variant Groups 1 and 2", Clinical and Vaccine Immunology, 16(2):156-162.
Van Der Ende et al., "Multiple Mechanisms of Phase Varitation of PorA in *Nesseria meningitides*," Infect Immun. 68 (12): 6685-6690 (2000).
Adu-Bobie et al., "GNA33 of *Neisseria meningitidis* is a lipoprotein required for cell separation, membrane architecture, and virulence," Infect Immun.72: 1914-1919 (2004).
Beernink, "Fine antigenic specificity and cooperative bactericidal activity of monoclonal antibodies directed at the meningococcal vaccine candidate factor h-binding protein,"Infect Immun.76(9): 4232-4240 (2008).
Biegel et al, "Ferric enterobactin binding and utilization by *Neisseria gonorrhoeae*," J. Bacteriology 181(9): 2895-2901 (1999).
Comanducci et al., "NadA diversity and carriage in *Neisseria meningitides*," Infect. Immun. 72(7) 4217-4223 (2004).
Dolan-Livengood et al., "Genetic basis for nongroupable *Neisseria meningitidis*," J. Infect. Dis. 187(10):1616-1628 (2003).
Fisseha et al., "Characterization of native outer membrane vesicles from lpxL mutant strains of *Neisseria meningitidis* for use in parenteral vaccination," Infect Immun. 73(7):4070-4080 (2005).
Fletcher et al., "Vaccine Potential of the *Neisseria meningitidis*2086 Lipoprotein," Infect Immun. 2088-2100 (2004).
Frasch, C.E. and Chapman, "Classification of *Neisseria meningitidis* group B into distinct serotypes. 3. Application of a new bactericidal-inhibition technique to distribution of serotypes among cases and carriers," J. Infect Dis. 127:149-154 (1973).
Frosch et al., "Generation of capsule-deficient *Neisseria meningitidis* strains by homologous recombination," Mol. Microbiol. 4(7): 1215-1218 (1990).
Gunn et al., "PmrA-PmrB-regulated genes necessary for 4-aminoarabinose lipid a modification and polymyxin resistance,"Mol. Microbiol. 27: 1171-1182 (1998).
Hobbs et al., "Recombinational reassortment among opa genes from ET-37 complex *Neisseria meningitidis* isolates of diverse geographical origins," Microbiology 144: 157-166 (1998).

(Continued)

*Primary Examiner* — Michele K Joike
*Assistant Examiner* — Mindy G Brown
(74) *Attorney, Agent, or Firm* — Carol L. Francis; Bozicevic, Field & Francis LLP

(57) ABSTRACT

The present disclosure generally provides non-naturally-occurring polynucleotide sequences that facilitate high-level expression of one or more gene products (e.g., polypeptides, RNA) of interest in *Neisseria meningitidis*. Methods of use of such sequences, e.g., use in vaccine production, are also provided.

33 Claims, 40 Drawing Sheets

(56) References Cited

OTHER PUBLICATIONS

Martin et al., "Highly conserved *Neisseria meningitidis* surface protein confers protection against experimental infection," J. Exp. Med. 185(7): (1997).

Masignani et al., "Vaccination against *Neisseria meningitidis* using three variants of the lipoprotein GNA1870," Exp Med. 197:789-799 (2003).

Moe et al., "Differences in surface expression of NspA among *Neisseria meningitidis* group B strains," Infect Immun. 67: 5664 (1999).

Moe et al., "Molecular analysis of anti-N-propionyl *Neisseria meningitidis* group B polysaccharide monoclonal antibodies," Mol Immunol. 43(9): 1424-1431 (2006).

Needleman and Wunsch, "A general method applicable to the search for similarities in the amino acid sequence of two proteins," J. Mol. Biol. 48:443 (1970).

O'Dwyer et. al., "Expression of heterologous antigens in commensal *Neisseria* spp.: preservation of conformational epitopes with vaccine potential,"Infect Immun. 72: 6511-6580 (2004).

Pearson and Lipman, "Improved tools for biological sequence comparison," Proc. Natl. Acad. Sci. 85(8):2444-2448 (1988).

Pettersson et al., "Vaccine potential of the *Neisseria meningitidis* lactoferrin-binding proteins LbpA and LbpB.," Vaccine 24(17): 3545-3557 (2006).

Pintor et al., "Analysis of TbpA and TbpB functionality in defective mutants of *Neisseria meningitides*," J. Med Microbiol. 47(9): 757-760 (1998).

Porro et al., "Natural and synthetic polypeptides that recognize the conserved lipid a binding site of lipopolysaccharides," Prog Clin Biol Res. 397:315-325 (1998).

Rokbi et al., "Heterogeneity of tbpB, the transferrinbinding protein B gene, amoung serogroup B *Neisseria meningitides* strains of the ET-5 complex," Clinical and Diagnostic Lab. Immun. 4(5):522-529 (1997).

Russell et al., "PorA variable regions of *Neisseria meningitidis*,"Emerging Infect Dis. 10:674-678 (2004).

Rustici et al., "Molecular mapping and detoxification of the lipid A binding site by synthetic peptides," Science 259: 361-365 (1993).

Sacchi et al., "Proposed standardization of *Neisseria meningitidis* PorA variable-region typing nomenclature," Clin Diagn Lab Immunol 5:845-855 (1998).

Sacchi et al., "Diversity and prevalence of PorA types in *Neisseria meningitidis* serogroup B in the United States, 1992-1998," J. Infect. Dis. 182:1169-1176 (2000).

Serruto et al., "*Neisseria meningitidis* GNA2132, a heparin-binding protein that induces protective immunity in humans,"Proc Natl. Acad. Sci. 107(8): 3770-3775 (2010).

Smith and Waterman, "Comparison of Biosequences,"Adv. Appl. Math. 2:482-489 (1981).

Steeghs et al., "mmunogenicity of outer membrane proteins in a lipopolysaccharide-deficient mutant of *Neisseria meningitidis*: influence of adjuvants on the immune response," Infect Immun. 67:4988-4993 (1999).

Steeghs et al., "Teasing apart structural determinants of 'toxicity' and 'adjuvanticity': implications for meningococcal vaccine development," J. Endotoxin Res. 10: 113-119 (2004).

Stephens et al., "Insertion of Tn916 in *Neisseria meningitidis* resulting in loss of group B capsular polysaccharide," Infect Immun. 59(11):4097-4102 (1991).

Swartley and Stephens, "Identification of a genetic locus involved in the biosynthesis of N-acetyl-D-mannosamine, a precursor of the (alpha 2→8)-linked polysialic acid capsule of serogroup B *Neisseria meningitidis*,"J. Bacteriol. 176(5) 1530-1540 (1994).

Van Der Ley et al., "Modification of lipid A biosynthesis in *Neisseria meningitidis* lpxL mutants: influence on lipopolysaccharide structure, toxicity, and adjuvant activity," Infect Immun.69:5981-5990 (2001).

Welsch et al., "Protective activity of monoclonal antibodies to genome-derived neisserial antigen 1870, a *Neisseria meningitidis* candidate vaccine,"J. Immunol. 172:5606-5615 (2004).

Welsch, "Complement-dependent synergistic bactericidal activity of antibodies against factor H-binding protein, a sparsely distributed meningococcal vaccine antigen,"J. Infect. Dis. 197(7): 1053-1061 (2008).

\* cited by examiner

FIG. 1A pNadA

TAACAGATATTAATGCCGAACTACCTAACTGCAAGAAT<u>AAATAAATAAATAAATAAATAAATAAATAAAT</u>

-35                            -10         +1

<u>AAA</u>TTGCGACAATGTATTGTATATATGCCTCCTTTCATATATACTTTAATATGTAAACAAACTT

GGTGGGGATAAAATACTTACAAAAGATTTCCGCCCCATTTTTTATCCACTCACAAAGGTAATG pPorA

AATAAGCTATTGTTTTATATCAAAATATAATCATTTTTAAAATAAAGGTTGCGGCATTTATCAGATATTTG

TTCTGAAAAATGGTTTTTTGC<u>GGGGGGGGGGG</u>TATAATTGAAGACGTATCGGGTGTTTGCCCCGA

TGTTTTTAGGTTTTTATCAAATTTACAAAAGGAAGCCCATATG

NadA    GACAATGTATTGTATATATGCCTCCTTTCATATATACTTTAATAT

PorA    TTCTGAAAAATGGTTTTTTGC<u>GGGGGGGGGGG</u>TATAATTGAAGAC

FIG. 2
Capsular group B strain MC58
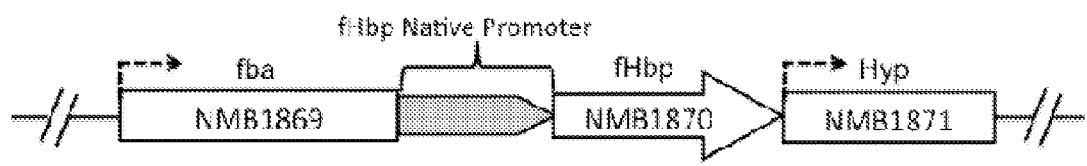
Capsular group A strain Z2491
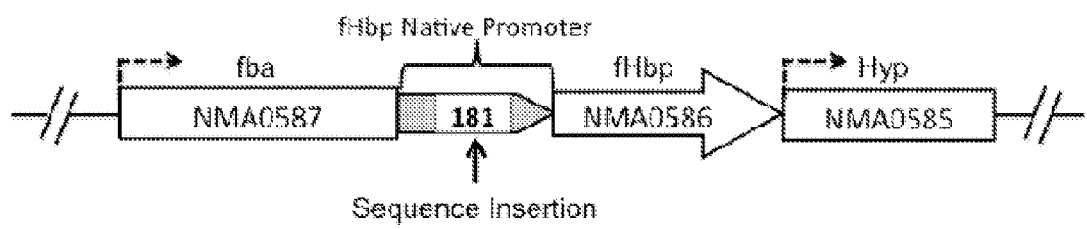
fba = fructose-1,6-bisphosphate aldolase
fHbp = factor H binding protein
Hyp = hypothetical protein

FIG. 5

|  | -35 | Spacer | -10 | +1 | Spacer |
|---|---|---|---|---|---|
| X0 | AATGGTTTTTTGCGGGGGGGGGG---- | | TATAAT | TGAAGACGTA | ← porA (control) |
| X1 | AATGGTT--ATATGCCTCCTTTCATA-- | | TATAAT | TGAAGACGTA | ← nadA |
| X2 | AATGGTT//ATATGCCTCCTTTCATA-- | | TATAAT | TGAAGACGTA | ← nadA variant |
| X3 | AATGGTT//AT//ATGCCTCCTTTCATA-- | | TATAAT | TGAAGACGTA | ← nadA variant |
| X4 | AATGGTT--ATATGC//TCATTTCATA-- | | TATAAT | TGAAGACGTA | ← nadA variant |
| X5 | AATGGTTTTTTGCGGGC--TTTCATA-- | | TATAAT | TGAAGACGTA | ← nadA variant |
| X6 | AATGGTTTTTTGCGGGC--TTTCAGG | | TATAAT | TGAAGACGTA | ← porA/nadA |
| X7 | AATGGTTTTTTGCGGGC--TTTCA--G | | TATAAT | TGAAGACGTA | ← porA/nadA |

FIG. 6
nmb1523 full length promoter
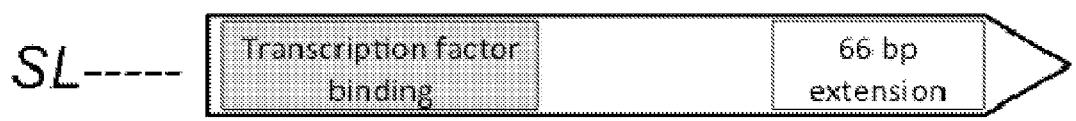
nmb1523 engineered promoters
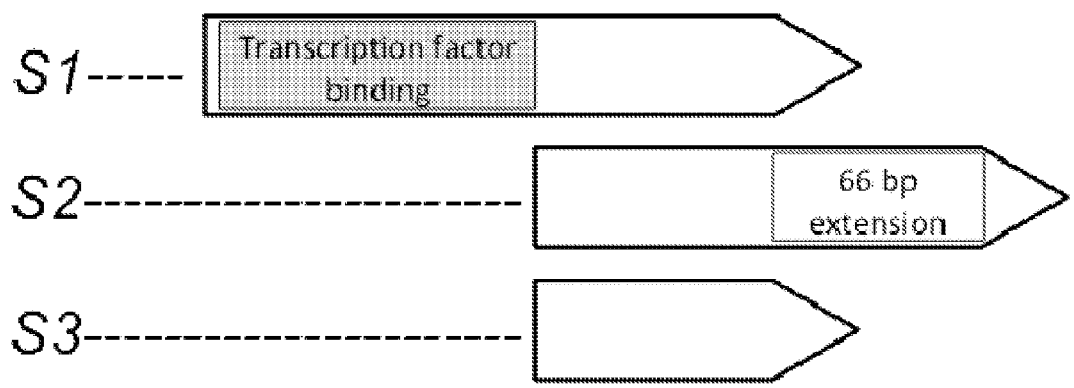

FIG. 16

| FAM18 | | | | | | | | | | | |
|---|---|---|---|---|---|---|---|---|---|---|---|
| Codon | Mean | SD | Codon | Mean | SD | Codon | Mean | SD | Codon | Mean | SD |
| GCT(A) | 9.2 | 10 | CAT(H) | 9.1 | 7.7 | CCT(P) | 7.5 | 7 | AGT(S) | 4.8 | 5.6 |
| GCC(A)* | 41 | 23 | CAC(H)* | 13.1 | 9.7 | CCC(P) | 14.3 | 10 | AGC(S)* | 15.9 | 9.6 |
| GCG(A) | 28.8 | 19 | ATT(I) | 22.4 | 14 | CCG(P)* | 17.9 | 11 | ACT(T) | 5.9 | 6.9 |
| GCA(A) | 20.4 | 12 | ATC(I)* | 30.4 | 15 | CCA(P) | 2.4 | 4.1 | ACC(T)* | 25.1 | 14 |
| TGT(C) | 3.3 | 4.6 | ATA(I) | 6 | 8.5 | CAG(Q) | 16.9 | 11 | ACG(T) | 13.1 | 9.1 |
| TGC(C)* | 8 | 7.3 | AAG(K) | 11.2 | 10 | CAA(Q)* | 22 | 13 | ACA(T) | 6.6 | 7 |
| GAT(D) | 22.9 | 15 | AAA(K)* | 46 | 20 | CGT(R) | 11.5 | 11 | GTT(V) | 16.9 | 11 |
| GAC(D)* | 29.1 | 15 | TTG(L) | 31.1 | 17 | CGC(R)* | 26.9 | 16 | GTC(V)* | 23.5 | 13 |
| GAG(E) | 12.8 | 10 | TTA(L) | 7.9 | 11 | CGG(R) | 6.8 | 7.4 | GTG(V) | 17.7 | 13 |
| GAA(E)* | 49.2 | 21 | CTT(L) | 10.3 | 7.6 | CGA(R) | 2.6 | 3.9 | GTA(V) | 10.2 | 8.5 |
| TTT(F)* | 21.5 | 15 | CTC(L) | 13.3 | 12 | AGG(R) | 3.9 | 5.5 | TGG(W)* | 12.2 | 10 |
| TTC(F) | 20.5 | 12 | CTG(L)* | 35 | 19 | AGA(R) | 2.8 | 5 | TAT(Y) | 14.8 | 12 |
| GGT(G) | 16.5 | 13 | CTA(L) | 2 | 3.8 | TCT(S) | 6.3 | 7.4 | TAC(Y)* | 15.2 | 10 |
| GGC(G)* | 42.4 | 20 | ATG(M)* | 25.1 | 12 | TCC(S) | 13.5 | 8.5 | TGA(.) | 1.6 | 2.4 |
| GGG(G) | 7.7 | 7.2 | AAT(N) | 15 | 14 | TCG(S) | 9.6 | 7.8 | TAG(.) | 0.4 | 1.5 |
| GGA(G) | 8.9 | 7.8 | AAC(N)* | 24.4 | 13 | TCA(S) | 4.3 | 5.7 | TAA(.)* | 2.1 | 2.6 |

| Codon | Mean | SD | Codon | Mean | SD | Codon | Mean | SD | Codon | Mean | SD |
|---|---|---|---|---|---|---|---|---|---|---|---|
| GCT ( A ) | 9.3 | 11 | CAT ( H ) | 9 | 7.6 | CCT ( P ) | 7.3 | 7.1 | AGT ( S ) | 4.7 | 5.7 |
| GCC ( A )* | 41.7 | 23 | CAC ( H )* | 13.1 | 9.8 | CCC ( P ) | 14.3 | 10 | AGC ( S )* | 16.1 | 9.8 |
| GCG ( A ) | 29.6 | 19 | ATT ( I ) | 22.2 | 14 | CCG ( P )* | 17.8 | 11 | ACT ( T ) | 6 | 6.8 |
| GCA ( A ) | 20.2 | 12 | ATC ( I )* | 30.5 | 15 | CCA ( P ) | 2.3 | 4.2 | ACC ( T )* | 25.2 | 14 |
| TGT ( C ) | 3.2 | 4.5 | ATA ( I ) | 5.8 | 8.1 | CAG ( Q ) | 17 | 12 | ACG ( T ) | 13.3 | 9.3 |
| TGC ( C )* | 8 | 7.6 | AAG ( K ) | 11.3 | 10 | CAA ( Q )* | 21.9 | 13 | ACA ( T ) | 6.4 | 7.2 |
| GAT ( D ) | 22.6 | 14 | AAA ( K )* | 45.7 | 20 | CGT ( R ) | 11.4 | 11 | GTT ( V ) | 16.6 | 11 |
| GAC ( D )* | 29.2 | 15 | TTG ( L ) | 31.2 | 17 | CGC ( R )* | 27.3 | 16 | GTC ( V )* | 23.6 | 13 |
| GAG ( E ) | 13 | 10 | TTA ( L ) | 7.7 | 11 | CGG ( R ) | 6.7 | 7.5 | GTG ( V ) | 18.1 | 13 |
| GAA ( E )* | 48.9 | 21 | CTT ( L ) | 10 | 7.5 | CGA ( R ) | 2.5 | 3.8 | GTA ( V ) | 10.2 | 8.5 |
| TTT ( F )* | 21.7 | 16 | CTC ( L ) | 13.6 | 12 | AGG ( R ) | 3.7 | 5.6 | TGG ( W )* | 12.2 | 10 |
| TTC ( F ) | 20.3 | 12 | CTG ( L )* | 35.6 | 19 | AGA ( R ) | 2.8 | 5.1 | TAT ( Y ) | 14.4 | 12 |
| GGT ( G ) | 16.3 | 13 | CTA ( L ) | 2.1 | 3.9 | TCT ( S ) | 6.2 | 7.5 | TAC ( Y )* | 15.2 | 9.9 |
| GGC ( G )* | 42.9 | 20 | ATG ( M )* | 25.1 | 12 | TCC ( S ) | 13.3 | 8.7 | TGA ( . ) | 1.5 | 2.4 |
| GGG ( G ) | 7.6 | 7.3 | AAT ( N ) | 14.7 | 14 | TCG ( S ) | 9.7 | 7.8 | TAG ( . ) | 0.5 | 1.5 |
| GGA ( G ) | 8.7 | 7.5 | AAC ( N )* | 24.5 | 13 | TCA ( S ) | 4.1 | 5.5 | TAA ( . )* | 2.1 | 2.6 |

FIG. 18

```
Optimized    1  ATG░░░░░░░AAA░░░░░░░░░░ACC░░TTCTGC░░░░CTGACCGCC░░
Original     1  ATGACTAGGAGCAAACCTGTGAACCGAACTACCTTTTTCTGCCTTTCTCTGACCGCCGCC Optimized   61  CTG░░░░░ACCGCCTGC░░░░░░░GGC░░░░AGC░░GGC░░░░░░░░░░░
Original    61  CTGATTCTGACCGCCTGCAGTAGCGGAGGCGGCGGAAGCGGAGGCGGCGGTGTCGCCGCC Optimized  121  ░░ATCGGT░░░░░░░░░░GCA░░ACCGCACCG░░░░░░AAAGACAAA░░
Original   121  GACATCGGTGCGGGGCTTGCTGATGCACTAACCGCACCGCTCGACCATAAAGACAAAGGT Optimized  181  ░░░░░TTGACGCTGGATCAG░░GTC░░AAAAAC░░AAA░░░░░CTG░░░░
Original   181  TTGCAGTCTTTGACGCTGGATCAGTCCGTCAGCAAAAACGAGAAACTGAAGCTGGCGGCA Optimized  241  CAA░░░░GAAAAA░░TAT░░AACGGCGACAGC░░AATACGGGCAAATTG░░░░
Original   241  CAAGGTGCGGAAAAAACTTATGGAAACGGCGACAGCCTCAATACGGGCAAATTGAAGAAC Optimized  301  ░░░░GTC░░CGC░░GAC░░ATC░░CAA░░GAA░░░░░░CAG░░ATTACC
Original   301  GACAAGGTCAGCCGCTTCGACTTTATCCGTCAAATCGAAGTGGACGGGCAGCTCATTACC Optimized  361  ░░░░AGC░░░░░░CAA░░TACAAA░░░░░░░GCC░░ACC░░░░░
Original   361  TTGGAGAGCGGAGAGTTCCAAGTGTACAAACAAAGCCATTCCGCCTTAACCGCCCTTCAG Optimized  421  ░░░░CAA░░░░░░TCG░░░░░░░░ATG░░░AAACGCCAG░░░░
Original   421  ACTGAGCAAGTACAAGACTCGGAGGATTCCGGGAAGATGGTTGCGAAACGCCAGTTCAGA Optimized  481  ATC░░░░░░GCGGGCGAACAT░░░░░░GAC░░░░CCCAAA░░GGC░░GCG
Original   481  ATCGGCGACATAGCGGGCGAACATACGTCTTTTGACAAGCTTCCCAAAGGCGGCAGTGCG Optimized  541  ░░TATCGC░░ACG░░░░░░░░░░░░░░AAACTGACC░░░░░
Original   541  ACATATCGCGGGACGGCGTTCGGTTCAGACGATGCTGGCGGAAAACTGACCTATACTATA Optimized  601  ░░TTCGCC░░AAA░░░░░CACGGCAAA░░GAACATTTGAAA░░░░GAA░░░
Original   601  GATTTCGCCGTCAAACAGGGACACGGCAAAATCGAACATTTGAAATCGCCCGAACTCAAT Optimized  661  ░░░░░░░░GCCTATATC░░░░░░AAAAAACGCCATGCCGTC░░░░
Original   661  GTCGACCTGGCCGCCGCCTATATCAAGCCGGATAAAAAACGCCATGCCGTCATCAGCGGT Optimized  721  ░░░░░░░░░░░░░░AAA░░░TACTCC░░GGCATC░░░░░░CAA
Original   721  TCCGTCCTTTACAACCAAGACGAGAAAGGCAGTTACTCCCTCGGCATCTTTGGCGGGCAA Optimized  781  ░░CAGGAA░░GCCGGC░░GCGGAA░░GAA░░░░AAC░░░░░░░░ATC░░
Original   781  GCCCAGGAAGTTGCCGGCAGCGCGGAAGTGGAAACCGCAAACGGCATACACCATATCGGT Optimized  841  ░░░░░░░░CAGTAA
Original   841  CTTGCCGCCAAGCAGTAA
```

FIG. 19 fHbp ID 23

ATGACCGGCTCCAAACCCGTGAACCGCACCGCATTCTGCTGCTTTTCGTTGAC
CGCCGCACTGATTCTGACCGCCTGCTCGTCGGGCGGCGGTGGCGTGGCAGCA
GATATCGGTGCAGGCTTGGCGGACGCACTGACCGCACCGTTGGATCATAAAGA
CAAAGGCCTGCAATCCTTGACGCTGGATCAGTCGGTACGCAAAAACGAAAAAT
TGAAACTGGCAGCCCAAGGCGCCGAAAAAACCTATGGTAACGGCGACTCCCTG
AATACGGGCAAATTGAAAAATGATAAAGTGTCGCGCTTTGACTTCATCCGCCAA
ATTGAAGTAGATGGCCAGTTGATCACCCTGGAATCGGGCGAATTTCAAATTTAC
AAACAGGACCACAGCGCAGTCGTTGCCCTGCAAATCGAAAAAATCAACAACCC
GGATAAAATCGACAGCTTGATTAACCAGCGCTCGTTTCTGGTTAGCGGCTTGG
GTGGCGAACACACCGCCTTCAATCAACTGCCGAGCGGTAAAGCCGAATATCAT
GGCAAAGCGTTTAGCTCCGATGACCCCAACGGCCGCCTGCACTATTCCATCGA
TTTCACCAAAAAACAAGGTTACGGCCGCATTGAACATTTGAAAACGCCCGAACA
GAATGTCGAACTGGCCAGCGCGGAATTGAAAGCAGATGAAAAATCCCATGCGG
TTATCTTGGGCGACACCCGCTATGGTGGCGAAGAAAAAGGCACGTACCACTTG
GCACTGTTCGGTGACCGCGCACAGGAAATTGCAGGCTCGGCGACGGTAAAAAT
CCGCGAAAAAGTTCACGAAATCGGTATTGCAGGTAAACAGTAA

FIG. 20 fHbp ID 4

ATGACCCGCTCGAAACCCGTGAACCGCACCGCATTCTGCTGCTTGTCGTTGAC
CGCCGCCCTGATTTTGACCGCCTGCTCGTCCGGCGGCGGTGGCGTGGCAGCA
GATATCGGTGCAGGCTTGGCAGACGCCCTGACCGCACCGTTGGATCACAAAGA
CAAATCGCTGCAAAGCTTGACGCTGGATCAGAGCGTATCCAAAAACGAAAAATT
GAAACTGGCAGCCCAAGGCGCCGAAAAAACCTATGGTAACGGCGACAGCCTG
AATACGGGCAAATTGAAAAATGATAAAGTCTCCCGCTTTGACTTCATCCGCCAA
ATTGAAGTTGATGGCCAGTTGATTACCCTGGAAAGCGGCGAATTTCAAGTCTAC
AAACAGTCGCACAGCGCGTTGACCGCACTGCAAACGGAACAAGTGCAGGACTC
CGAACATTCGGGCAAAATGGTAGCGAAACGCCAGTTTCGCATCGGTGATATTG
CCGGCGAACACACCAGCTTCGACAAATTGCCCGAAGGTGGCCGCGCAACCTAT
CGCGGTACGGCATTTGGCAGCGATGACGCGTCCGGCAAACTGACCTACACGA
TCGATTTCGCGGCAAAACAAGGTCACGGCAAAATTGAACATTTGAAATCGCCG
GAACTGAACGTGGACTTGGCCGCGTCCGATATCAAACCCGACAAAAAACGCCA
TGCGGTCATTTCCGGCTCGGTTCTGTATAATCAGGCCGAAAAAGGTAGCTACTC
CTTGGGCATCTTCGGTGGCCAAGCCCAGGAAGTTGCGGGCTCGGCAGAAGTA
GAAACCGCAAATGGTATCCGCCACATCGGCTTGGCAGCAAAACAATAA

FIG. 21 fHbp ID 28

GGCGTAGCAGCTGACATCGGTACCGGCCTGGCGGACGCTCTGACCGCCCCGT
TGGACCATAAAGACAAAGGCCTGAAAAGCCTGACCTTGGAAGACAGCATTCCG
CAAAACGGTACACTCACGCTGAGCGCTCAAGGCGCCGAAAAAACCTTCAAAGC
GGGCGACAAAGATAACTCTCTGAACACCGGCAAACTGAAAAATGACAAAATTTC
TCGCTTCGACTTCGTACAAAAAATCGAAGTCGACGGTCAAACAATCACATTGGC
AAGCGGCGAATTCCAAATTTATAAACAAACCACTCAGCCGTTGTCGCCCTGCA
AATTGAGAAAATTAACAACCCTGACAAAACGGACTCCCTGATCAACCAACGTTC
CTTCTTGGTGTCTGGCCTGGGCGGTGAACATACCGCGTTCAATCAACTACCTG
GTGGTAAAGCGGAATATCACGGTAAAGCTTTCTCTTCCGACGACCCCAACGGC
CGTTTGCACTACTCCATCGATTTCACCAAAAAACAGGGTTATGGTCGCATTGAA
CACCTGAAAACCCTGGAGCAAAATGTAGAATTGGCCGCTGCCGAACTGAAGGC
TGACGAAAATCTCACGCCGTTATCCTGGGTGATACCCGCTACGGTTCTGAAG
AAAAAGGCACTTACCACCTGGCCCTGTTTGGCGACCGTGCGCAAGAAATTGCC
GGCAGCGCCACCGTCAAAATCGGTGAAAAGTCCACGAAATCGGCATTGCGG
GCAAGCAA

FIG. 22 fHbp ID 1

GGTGTTGCGGCCGACATCGGCGCCGGGCTGGCCGACGCGCTGACGGCGCCT
CTGGACCACAAAGACAAAGGCTTGCAGTCTTTGACTCTGGACCAATCTGTACG
CAAGAACGAAAAACTCAAACTGGCCGCTCAAGGTGCGGAAAAGACCTACGGCA
ACGGCGACAGCCTGAACACTGGCAAACTGAAAAACGACAAAGTGTCTCGCTTT
GACTTCATCCGTCAAATTGAAGTCGACGGCCAGTTGATTACCTTAGAATCCGGC
GAATTCCAAGTTTACAAACAGTCTCACAGCGCCTTGACGGCGTTCCAGACTGAA
CAAATCCAAGATAGCGAACACTCTGGCAAAATGGTTGCCAAACGCCAGTTTCG
CATCGGCGACATCGCAGGTGAACACACTAGCTTCGATAAACTGCCGGAAGGCG
GCCGCGCCACCTACCGCGGTACCGCGTTCGGCAGCGACGATGCCGGTGGCAA
ATTGACTTATACCATTGATTTTGCCGCAAAACAAGGCAACGGCAAAATTGAACA
CTTGAAATCTCCTGAACTGAACGTAGACCTCGCGGCAGCAGACATCAAGCCGG
ATGGTAAGCGCCACGCTGTGATCAGCGGCAGCGTTTTGTACAACCAAGCAGAA
AAAGGCTCCTATTCCTTAGGCATCTTCGGCGGCAAAGCACAAGAGGTAGCCGG
CTCGGCCGAAGTAAAAACTGTGAACGGCATCCGCCACATCGGTCTGGCCGCCA
AACAA

FIG. 23 fHbp ID 14

GGGGTCGCTGCAGACATTGGCGCTGGCCTGGCCGATGCCTTGACCGCGCCGC
TGGATCACAAAGACAAATCCTTGCAAAGTTTGACTCTGGACCAATCCGTGCGCA
AAAATGAAAAACTGAAGCTGGCGGCTCAAGGCGCGGAGAAAACCTATGGCAAC
GGCGATAGCCTGAACACTGGCAAACTGAAAAATGACAAAGTAAGCCGTTTCGA
CTTTATCCGCCAAATTGAAGTTGACGGCCAATTGATTACCCTGGAATCCGGCGA
ATTCCAAGTGTACAAACAATCTCACAGCGCTTTGACCGCACTCCAAACCGAGCA
AGAACAAGACCCTGAACACTCGGGTAAAATGGTCGCGAAACGCCGTTTTAAAAT
CGGCGATATCGCCGGTGAACACACGAGCTTCGATAAATTGCCGAAGGATGTTA
TGGCGACCTACCGCGGCACTGCCTTTGGCTCCGACGACGCCGGCGGTAAATT
GACCTACACTATTGACTTCGCCGCCAAACAAGGTCACGGCAAGATTGAACACC
TGAAAAGCCCGGAACTCAACGTGGAACTGGCAACCGCATACATCAAACCGGAT
GAGAAACACCACGCGGTTATCTCTGGCAGCGTCCTGTACAATCAAGATGAAAA
AGGCTCCTACTCTTTGGGTATCTTCGGTGGTCAAGCTCAAGAAGTAGCGGGCT
CGGCGGAAGTGGAAACCGCCAACGGCATTCACCACATTGGCCTGGCAGCGAA
ACAG

FIG. 24 fHbp ID 45

GGCGTCGCGGCCGACATTGGCGCCGGTTTGGCGGACGCGCTCACCGCTCCGT
TGGACCATAAAGATAAAGGCTTGCAATCCCTGACGTTGGATCAAAGCGTTCGCA
AAAACGAAAAACTGAAATTGGCCGCGCAAGGTGCTGAAAAAACCTACGGTAAC
GGTGACTCTTTGAACACCGGTAAATTAAAAAACGATAAAGTCAGCCGTTTCGAC
TTTATCCGCCAAATTGAAGTTGACGGTAAATTGATTACCTTGGAAAGCGGCGAA
TTCCAAGTCTACAAACAAAGCCACAGCGCCCTGACCGCTTTGCAAACGGAACA
AGTTCAAGATTCCGAAGACTCCGGCAAAATGGTTGCAAAACGCCAGTTCCGTAT
CGGGGATATCGCGGGCGAACACACCAGCTTCGACAAATTGCCTAAAGGTGGTT
CGGCAACCTATCGCGGTACCGCCTTCGGTTCTGATGACGCGGGTGGCAAATTA
ACCTATACCATTGATTTCGCTGCCAAACAAGGCCATGGTAAAATCGAGCACTTG
AAATCACCGGAGCTGAACGTTGAACTGGCCACGGCCTACATCAAACCGGACGA
AAAACGCCACGCCGTAATCTCCGGTTCTGTTTTGTACAACCAAGATGAAAAAGG
CTCCTATTCTTTGGGCATTTTCGGCGGCCAAGCCCAAGAAGTGGCGGGCTCTG
CAGAAGTCGAAACCGCAAACGGCATCCGTCACATTGGTCTGGCCGCAAAACAG

FIG. 25 fHbp ID 55

GGTGTCGCGGCCGACATCGGTGCTGGCCTGGCTGACGCCCTGACCGCACCTT
TGGACCACAAAGACAAAGGCTTGCAATCCCTGATGCTGGACCAATCCGTCCGG
AAGAACGAAAAATTGAAGTTGGCGGCCCAGGGCGCTGAAAAAACCTACGGTAA
TGGTGACTCCCTGAACACTGGCAAACTGAAAAACGATAAAGTGTCCCGCTTTGA
CTTCATTCGCCAAATTGAAGTGGATGGTAAACTGATTACCCTGGAAAGCGGCGA
ATTCCAAATTTACAAACAAGACCATAGCGCGGTCGTGGCACTGCAAATCGAAAA
AATTAACAACCCCGACAAAATCGATTCTTTGATCAATCAGCGCTCCTTCTTGGTC
AGCGGCTTGGGCGGCGAGCACACCGCATTTAACCAATTGCCTAGCGGCAAAG
CAGAATACCACGGTAAAGCGTTTTCCTCAGACGACGCAGGTGGCAAATTGACC
TACACCATTGATTTTGCCGCCAAACAAGGTCATGGCAAAATCGAACACCTGAAA
ACTCCGGAGCAAAATGTAGAGCTGGCATCCGCCGAACTGAAAGCCGACGAAAA
ATCTCACGCAGTGATCTTGGGCGACACGCGTTATGGCGGCGAAGAAAAAGGCA
CCTACCACCTGGCCCTGTTCGGTGACCGTGCACAAGAAATTGCAGGTAGCGCC
ACTGTGAAAATCCGCGAGAAAGTACACGAAATTGGCATTGCAGGTAAACAA

FIG. 26 fHbp ID 19

GGTGTGGCGGCGGACATCGGCGCTGGCTTGGCCGACGCGCTGACGGCGCCT
CTGGATCATAAAGATAAAAGCCTGCAATCTTTGACGTTGGACCAATCTGTCCGT
AAAAATGAAAAACTGAAGTTGGCCGCGCAGGGCGCAGAAAAGACTTATGGTAA
CGGTGACTCTTTAAATACCGGCAAACTGAAAAACGATAAAGTCTCCCGCTTTGA
TTTCATCCGCCAAATTGAGGTCGATGGCCAATTGATCACGCTGGAGTCTGGCG
AATTCCAAATCTACAAACAAGACCATTCCGCTGTTGTGGCTCTGCAAATCGAAA
AAATCAATAACCCCGACAAAATCGACTCTTTGATCAACCAACGTAGCTTCCTCG
TATCTGGTCTGGGCGGTGAGCACACCGCGTTCAACCAATTGCCCAGCGGTAAG
GCCGAATACCATGGCAAAGCGTTCTCTTCTGACGATGCAGGTGGTAAACTGAC
CTACACCATTGATTTCGCAGCTAAACAAGGCCATGGTAAAATCGAACATCTGAA
AACCCCGGAACAGAATGTAGAGCTGGCATCTGCAGAACTGAAAGCCGACGAGA
AATCACACGCCGTAATCCTGGGCGATACCCGCTACGGTGGTGAAGAAAAGGC
ACCTATCACTTGGCACTGTTCGGTGACCGTGCACAAGAAATCGCTGGTTCTGCA
ACCGTGAAAATTCGTGAAAAGTACACGAAATTGGCATTGCCGGAAAACAA

FIG. 27 fHbp ID 77

GGCGTAGCCGCTGATATCGGCGCCGGCCTGGCGGATGCGTTGACAGCACCGC
TGGACCATAAAGATAAAGGTCTGCAATCCCTGACCTTGGATCAAAGCGTACGTA
AAAACGAAAAATTGAAACTAGCCGCCCAAGGTGCGGAAAAAACCTACGGTAAC
GGCGATTCTTTGAACACGGGCAAATTGAAAAATGACAAAGTCTCCCGCTTTGAC
TTCATCCGCCAAATTGAAGTTGACGGAAAATTGATTACCCTGGAAAGCGGTGAA
TTCCAAGTATACAAACAAAGCCACTCTGCCTTGACCGCATTGCAGACCGAACAA
GTGCAAGACAGCGAAGATAGCGGCAAAATGGTTGCCAAACGCCAATTCCGCAT
TGGTGACATAGCCGGCGAACACACCAGTTTCGACAAACTGCCTAAAGGCGGTT
CTGCTACTTACCGTGGCACAGCCTTGGGCTCCGACGACGCCGGCGGTAAATTG
ACCTACACTATCGACTTCGCCGCCAAACAAGGCCACGGCAAATCGAGCACTT
GAAATCACCGGAATTGAACGTCGAATTGGCCACCGCCTACATCAAACCGGACG
AAAAACGTCATGCCGTGATTTCTGGCTCTGTTTTGTACAACCAAGACGAGAAAG
GCAGCTACAGCTTGGGTATTTTCGGCGGTCAAGCCCAAGAAGTTGCGGGCTCC
GCAGAAGTAGAAACCGTGAACGGCATTCACCACATTGGCCTGGCTGCAAAACA
A

FIG. 28

NspA (nmb0663)

ATGAAAAAAGCCCTGGCCACCCTGATTGCGCTGGCACTGCCTGCGGCGGCAC
TCGCCGAAGGCGCAAGCGGTTTCTACGTGCAAGCCGATGCCGCACACGCCAA
AGCCTCGTCCTCCCTGGGTTCTGCCAAAGGCTTTTCTCCTCGCATCAGCGCCG
GTTACCGTATCAACGATCTGAGGTTTGCCGTAGACTACACGCGTTATAAAAACT
ACAAAGCACCCAGCACTGACTTCAAATTGTACTCTATCGGCGCGTCTGCTATCT
ATGATTTCGACACCCAATCCCCGGTTAAACCTTACTTGGGAGCCCGTTTGTCCT
TGAACCGCGCATCCGTGGACCTGGGTGGCAGCGACTCCTTTTCACAAACCAGC
ATCGGTCTGGGCGTGCTGACCGGTGTAAGCTACGCTGTCACGCCTAACGTAGA
TCTGGACGCCGGTTACCGTTACAATTACATTGGTAAAGTTAACACTGTGAAAAA
TGTACGCTCCGGCGAACTGTCCGCGGGCGTCCGCGTAAAATTCTGA

FIG. 29

NspA (nmc0612, nma0862)

ATGAAAAAAGCCTTGGCCACCTTGATCGCCTTGGCCTTGCCGGCCGCCGCCTT
GGCCGAAGGCGCCTCCGGCTTCTACGTTCAAGCCGACGCCGCCCACGCCAAA
GCCTCCTCCTCCTTGGGCTCCGCCAAAGGCTTCTCCCCGCGCATCTCCGCCGG
CTACCGCATCAACGACTTGCGCTTCGCCGTTGACTACACCCGCTACAAAAACTA
CAAAGCCCCGTCCACCGACTTCAAATTGTACTCCATCGGCGCCTCCGCCATCT
ACGACTTCGACACCCAATCCCCGGTTAAACCGTACTTGGGCGCCCGCTTGTCC
TTGAACCGCGCCTCCGTTGACTTGGGCGGCTCCGACTCCTTCTCCCAAACCTC
CACCGGCTTGGGCGTTTTGGCCGGCGTTTCCTACGCCGTTACCCCGAACGTTG
ACTTGGACGCCGGCTACCGCTACAACTACATCGGCAAAGTTAACACCGTTAAAA
ACGTTCGCTCCGGCGAATTGTCCGCCGGCGTTCGCGTTAAATTCTGA

FIG. 30

NHbp(nmb2132)

```
ATGTTTAAGCGTTCCGTTATTGCTATGGCCTGCATTTTCGCCTTGTCCGCCTGC
GGTGGCGGTGGTGGCGGCAGCCCCGACGTAAAATCTGCCGACACCTTGAGCA
AACCCGCTGCGCCTGTTGTATCTGAAAAAGAAACCGAAGCGAAAGAAGATGCT
CCGCAGGCGGGCTCCCAAGGTCAAGGCGCACCTTCTGCCCAAGGCTCACAAG
ACATGGCCGCGGTGTCCGAAGAAAATACCGGTAATGGTGGCGCTGTTACCGCA
GACAATCCGAAAAACGAAGATGAAGTTGCTCAAAACGACATGCCACAGAACGC
CGCCGGCACTGACTCTTCCACCCCCAACCACACCCCTGACCCTAATATGTTGG
CCGGCAACATGGAAAACCAAGCCACCGACGCAGGCGAGTCCAGCCAACCC
GCCAACCAGCCTGATATGGCGAACGCGGCCGACGGTATGCAAGGCGATGACC
CGAGCGCAGGCGGTCAAAACGCGGGCAACACCGCCGCCCAAGGCGCTAACCA
GGCTGGTAACAACCAAGCCGCAGGCAGCAGCGACCCGATCCCGGCATCAAAC
CCGGCACCTGCAAACGGCGGAAGCAACTTCGGCCGCGTTGACTTGGCAAACG
GCGTGCTGATCGACGGCCCGTCTCAAAACATCACCTTGACCCATTGTAAAGGC
GACTCTTGCTCCGGCAACAATTTCCTGGACGAGGAAGTCCAGTTGAAATCCGA
ATTTGAAAAGCTGAGCGACGCGGATAAAATTTCTAACTATAAAAAGACGGCAA
AAACGACAAATTCGTAGGCCTGGTTGCCGATAGTGTGCAGATGAAAGGCATC
AACCAATACATTATCTTCTATAAACCGAAACCTACCTCCTTCGCTCGTTTCCGCC
GTAGCGCCCGCTCCCGCCGTTCCTTGCCGGCCGAAATGCCCCTGATCCCCGT
AAACCAAGCTGACACTTTGATCGTAGATGGCGAGGCAGTTTCTCTCACCGGCC
ACAGCGGCAATATTTTCGCACCCGAAGGTAACTACCGCTACCTGACTTATGGC
GCCGAAAAACTGCCGGGTGGCTCTTATGCGCTGCGCGTCCAAGGCGAGCCGG
CAAAAGGTGAAATGTTGGCCGGCGCTGCCGTATATAACGGCGAAGTGTTGCAC
TTCCATACCGAAAACGGTCGCCCGTACCCGACCCGCGGCCGATTTGCTGCTAA
AGTCGACTTCGGCAGCAAAAGTGTTGACGGTATTATCGACTCAGGCGACGATT
TGCACATGGGTACGCAAAAATTCAAAGCCGCGATCGACGGTAATGGCTTCAAA
GGCACCTGGACGGAAAACGGTTCTGGTGACGTTTCTGGTAAATTCTACGGCCC
CGCCGGCGAAGAGGTCGCGGGCAAATATTCATACCGCCCTACCGACGCCGAA
AAAGGGGGCTTTGGTGTTTTCGCCGGTAAAAAGAACAAGACTGA
```

FIG. 31

TbpB (Tbp2, nmb0461)

```
ATGAACAACCCGTTGGTTAACCAAGCCGCCATGGTTTTGCCGGTTTTCTTGTTGTCCGCCTGCTT
GGGCGGCGGCGGCTCCTTCGACTTGGACTCCGTTGACACCGAAGCCCCGCGCCCGGCCCCGA
AATACCAAGACGTTTTCTCCGAAAAACCGCAAGCCCAAAAAGACCAAGGCGGCTACGGCTTCGC
CATGCGCTTGAAACGCCGCAACTGGTACCCGCAAGCCAAAGAAGACGAAGTTAAATTGGACGAA
TCCGACTGGGAAGCCACCGGCTTGCCGGACGAACCGAAAGAATTGCCGAAACGCCAAAAATCC
GTTATCGAAAAAGTTGAAACCGACTCCGACAACAACATCTACTCCTCCCCGTACTTGAAACCGTC
CAACCACCAAAACGGCAACACCGGCAACGGCATCAACCAACCGAAAAACCAAGCCAAAGACTAC
GAAAACTTCAAATACGTTTACTCCGGCTGGTTCTACAAACACGCCAAACGCGAATTCAACTTGAA
AGTTGAACCGAAATCCGCCAAAAACGGCGACGACGGCTACATCTTCTACCACGGCAAAGAACCG
TCCCGCCAATTGCCGGCCTCCGGCAAAATCACCTACAAAGGCGTTTGGCACTTCGCCACCGACA
CCAAAAAAGGCCAAAAATTCCGCGAAATCATCCAACCGTCCAAATCCCAAGGCGACCGCTACTC
CGGCTTCTCCGGCGACGACGGCGAAGAATACTCCAACAAAAACAAATCCACCTTGACCGACGG
CCAAGAAGGCTACGGCTTCACCTCCAACTTGGAAGTTGACTTCCACAACAAAAAATTGACCGGC
AAATTGATCCGCAACAACGCCAACACCGACAACAACCAAGCCACCACCACCCAATACTACTCCTT
GGAAGCCCAAGTTACCGGCAACCGCTTCAACGGCAAAGCCACCGCCACCGACAAACCGCAACA
AAACTCCGAAACCAAAGAACACCCGTTCGTTTCCGACTCCTCCTCCTTGTCCGGCGGCTTCTTC
GGCCCGCAAGGCGAAGAATTGGGCTTCCGCTTCTTGTCCGACGACCAAAAAGTTGCCGTTGTTG
GCTCCGCCAAAACCAAAGACAAACCGGCCAACGGCAACACCGCCGCCGCCTCCGGCGGCACC
GACGCCGCCGCCTCCAACGGCGCCGCCGGCACCTCCTCCGAAAACGGCAAATTGACCACCGTT
TTGGACGCCGTTGAATTGAAATTGGGCGACAAAGAAGTTCAAAAATTGGACAACTTCTCCAACGC
CGCCCAATTGGTTGTTGACGGCATCATGATCCCGTTGTTGCCGGAAGCCTCCGAATCCGGCAAC
AACCAAGCCAACCAAGGCACCAACGGCGGCACCGCCTTCACCCGCAAATTCGACCACACCCCG
GAATCCGACAAAAAAGACGCCCAAGCCGGCACCCAAACCAACGGCGCCCAAACCGCCTCCAAC
ACCGCCGGCGACACCAACGGCAAAACCAAAACCTACGAAGTTGAAGTTTGCTGCTCCAACTTGA
ACTACTTGAAATACGGCATGTTGACCCGCAAAAACTCCAAATCCGCCATGCAAGCCGGCGAATC
CTCCTCCCAAGCCGACGCCAAAACCGAACAAGTTGAACAATCCATGTTCTTGCAAGGCGAACGC
ACCGACGAAAAAGAAATCCCGTCCGAACAAAACATCGTTTACCGCGGCTCCTGGTACGGCTACA
TCGCCAACGACAAATCCACCTCCTGGTCCGGCAACGCCTCCAACGCCACCTCCGGCAACCGCG
CCGAATTCACCGTTAACTTCGCCGACAAAAAAATCACCGGCACCTTGACCGCCGACAACCGCCA
AGAAGCCACCTTCACCATCGACGGCAACATCAAAGACAACGGCTTCGAAGGCACCGCCAAACC
GCCGAATCCGGCTTCGACTTGGACCAATCCAACACCACCCGCACCCCGAAAGCCTACATCACC
GACGCCAAAGTTCAAGGCGGCTTCTACGGCCCGAAAGCCGAAGAATTGGGCGGCTGGTTCGCC
TACCCGGGCGACAAACAAACCAAAAACGCCACCAACGCCTCCGGCAACTCCTCCGCCACCGTT
GTTTTCGGCGCCAAACGCCAACAACCGGTTCGCTAA
```

FIG. 32

TbpA (Tbp1, nmb0461)

```
ATGCAGCAACAACACCTGTTCCGCTTCAACATTCTGTGCCTGAGCCTGATGACTGCCCTG
CCTGCGTACGCGGAGAACGTACAAGCCGGCCAAGCCCAAGAAAAACAGCTGGACACCATC
CAAGTAAAAGCCAAAAAACAAAAAACTCGCCGCGATAACGAGGTTACCGGTCTGGGCAAA
TTGGTGAAATCGTCGGACACCTTGAGCAAGGAGCAAGTATTGAATATTCGTGACCTGACC
CGCTACGACCCTGGTATCGCCGTCGTAGAACAGGGCCGTGGCGCAAGCTCAGGTTATTCC
ATTCGTGGTATGGACAAAAATCGCGTAAGCCTGACCGTTGACGGCGTCTCCCAGATCCAG
TCTTACACAGCCCAAGCCGCTCTGGGCGGTACCCGCACCGCCGGCAGCTCAGGCGCCATT
AACGAAATCGAATACGAAATGTTAAAGCAGTTGAAATTAGCAAAGGCTCCAACTCCGTT
GAGCAAGGCTCCGGCGCCTTGGCCGGCAGCGTAGCCTTTCAAACTAAAACCGCTGATGAC
GTGATTGGCGAAGGTCGTCAATGGGGCATCCAATCGAAAACCGCTTACAGCGGCAAAAAC
CGCGGCTTGACCCAATCTATCGCATTGGCGGGTCGTATTGGCGGTGCCGAGGCACTGCTG
ATCCACACCGGTCGTCGCGCAGGCGAAATCCGCGCCCACGAAGATGCCGGCAGGGGTGTT
CAGTCCTTTAACCGCTTGGTTCCCGTGGAAGATTCATCGAACTACGCATACTTCATCGTG
AAAGAAGAATGCAAAAACGGTAGCTACGAAACGTGCAAAGCTAACCCTAAAAAGGACGTT
GTTGGCAAGGACGAACGCCAAACTGTTAGCACTCGTGATTACACCGGTCCCAACCGCTTT
CTGGCAGACCCGCTGTCATATGAATCCCGCTCCTGGCTCTTCCGCCCGGGTTCCGCTTC
GAGAACAAACGACACTATATTGGGGGCATCTTGGAACACACTCAACAAACCTTCGACACC
CGTGATATGACAGTACCCGCCTTCTTGACCAAAGCTGTCTTCGATGCGAACAAAAAACAA
GCGGGTTCTCTACCTGGCAATGGTAAATACGCCGGCAATCACAAATACGGCGGTCTGTTT
ACCAACGGTGAAAACGGTGCATTGGTCGGCGCCGAATACGGCACGGGCGTCTTTTACGAC
GAGACCCATACGAAAAGTCGCTACGGCTTGGAGTATGTTTATACAAACGCCGACAAAGAC
ACGTGGGCCGACTACGCCCGCTTGTCTTACGACCGTCAGGGTATTGGCCTGGACAACCAC
TTTCAACAAACTCACTGCTCCGCGGACGGGAGCGACAAATATTGCCGCCCTTCTGCGGAC
AAACCGTTCTCCTACTACAAATCCGATCGCGTGATCTATGGCGAAAGTCATCGACTGTTA
CAGGCCGCGTTCAAAAAAGCTTCGACACCGCCAAAATTCGTCACAATCTGTCGGTCAAT
TTGGGCTTCGACCGCTTCGGTAGCAACCTGCGTCACCAAGATTACTATTACCAACATGCT
AATCGCGCCTACTCAAGTAACACCCCCCTCAAAACAACGGCAAAAAAATCTCACCCAAC
GGCTCCGAAACTTCCCCTTACTGGGTGACCATTGGTCGTGGCAACGTAGTTACTGGCCAA
ATTTGCCGTCTGGGTAACAATACCTATACCGATTGCACTCCGCGCTCAATCAACGGCAAA
AGCTACTACGCAGCCGTTCGCGACAACGTCCGCCTCGGCCGTTGGGCAGACGTCGGCGCT
GGTCTGCGCTACGACTACCGCTCTACTCACAGCGACGACGGCAGTGTGAGTACTGGTACT
CACCGTACCTTGTCCTGGAATGCCGGCATCGTCCTCAAACCTACCGACTGGCTGGATTTG
ACCTACCGTACATCCACCGGCTTTCGTTTGCCTTCATTCGCGGAGATGTACGGTTGGCGT
GCAGGCGTACAAAGCAAAGCTGTGAAATTGATCCGGAAAAATCCTTCAATAAAGAAGCT
GGCATCGTATTCAAAGGCGACTTCGGCAACCTGGAAGCATCCTGGTTCAACAACGCCTAT
CGTGACCTGATTGTGCGTGGCTATGAAGCCCAAATTAAAGACGGCAAAGAAGAAGCGAAA
GGCGACCCGGCTTACCTGAACGCGCAATCTGCGCGCATCACCGGCATCAATATCCTGGGC
AAAATCGACTGGAACGGCGTGTGGGATAAACTGCCCGAAGGCTGGTACTCCACTTTCGCT
TATAACCGCGTGCGTGTCCGCGATATCAAAAAACGTGCTGACCGCACAGATATCCAATCT
CACTTATTCGATGCAATTCAACCTTCCCGCTATGTCGTTGGCTTGGGTTATGACCAACCT
GAAGGTAAATGGGGCGTGAATGGCATGTTGACTTACTCCAAAGCCAAAGAGATTACCGAA
CTGTTGGGCTCTCGTGCGTTGTTGAACGGCAACAGCCGTAACACTAAAGCAACCGCGCGT
CGCACGCGCCCTTGGTATATTGTCGATGTATCAGGTTACTATACCGTTAAAAAACACTTC
ACCCTGCGCGCCGGCGTTTACAATTTGTTGAACTATCGTTATGTCACCTGGGAAAATGTA
CGTCAAACCGCTGGAGGCGCCGTTAACCAACATAAAAACGTGGGCGTTTACAACCGTTAC
GCGGCGCCAGGTCGTAACTACACCTTCAGCTTGGAAATGAAATTCTAA
```

FIG. 33

LbpB (nmb1541)

```
ATGTGCAAACCCAATTACGGTGGTATCGTGTTGTTGCCCTTGCTGCTGGCTTCCTGTATT
GGCGGCAACTTTGGCGTACAACCGGTAGTTGAAAGCACCCCTACTGCGTACCCAGTGACC
TTCAAATCTAAAGACGTTCCGACCCCGCCGCCGGCCGGTTCCAGCGTGGAAACAACCCCA
GTTAACCGCCCGGCAGTAGGCGCCGCTATGCGTCTCCCGCGCCGCAATATCGCTAGCTAC
AAACAGGACGGCACTGAAATCCCTGACAAACACCAAGCAGAAGAACACCTGCCTCTGAAA
GAAAAAGACATCCTGTTCCTGGACGGCACCCTGAAAGAACAAGCAGACAAATTGAAAAAG
AAAATCAACGAACGCTATAGCGATGTTCGCGTTATTACCTCCAAAAAAGAAGAAGAGAAA
TACCAATACCAATTCGTACGCGCGGGTTACGTGTTCACGCGCGCCGAAGGCAAAGACAAC
GAAAAAGAAAAAACCTCTGATGGCAAAGAATTCGTCAACCGCTTCTCCTACGACGGTTTC
GTTTATTACTCTGGCGAACGCCCTTCCCAATCGTTGCCTTCCGCAGGCACCGTGCAATAT
AGCGGCAACTGGCAATATATGACCGACGCAAAACGCCACCGCACTGGCAAAGCAGTCTCA
AGCACTGACTTGGGCTACACCACGTACTACGGTAACGAAATCGGTGCCACCTCCTACGAA
GCTCGCGACGCGGACGACCGCGAAAAACACCCTGCTGAATATACTGTCGACTTCGACAAT
AAAACCCTGAACGGCAAACTGATCAAAAACCAGTACGTTCAAAACAAAAGCAACCCCAAC
GAACCGAAAAAACCGTTGACCATCTACGACATCACTGCCACCCTGGATGGTAACCGCTTC
ACCGGCTCCGCAAAGGTATCCACCGAAGTGAAAACCCAACACGCTGATAAAGAATACCTG
TTTTTCCACACCGATGCCGACCAACGCTTGGAAGGCGGCTTCTTCGGCGACAACGGCGAA
GAATTGGCCGGACGCTTCATTTCGAACGATAACTCTGTGTTTGGCGTTTTCGCTGGCAAA
CAAAAAACTGAAACCGAAAATGCGGCTGACACAAAACCGGCCCTCTCAAGCGGCAAACAC
ACTAAAATCCTGGACTCTCTGAAAATTTCCGTTGACGAAGCTAGCGACAAAAACCCGCGC
GAATTCGCTATCTCGAGTATGCCCGACTTTGGTCACCCGGACAAACTGTTGGTCGAAGGT
CGCGAAATCCCTCTGGTGAACAAAGAACAAACCATCGAGCTGGCAGACGGCCGCAAAACT
ACTATTCGCACGTGCTGTGACTTCCTCACTTACGTCAAAATTGGCCGTATGCAAACTGAG
CGCCCGGCCGCAAAACCTAAAGCCCAGGATGAAGAACGTGATGAGGAAGACACCGGTGTG
GACTCAGTTGAAGAGGGCGAAGATGAGATCGATGACGAAGAAGGTACCGAAGACGCAGCC
GTGAAAGACGAAGGCTCCGAAGAAGATGAGGCTGTGGAAGGTGAGGACGAAGCTGAAGAA
CCAGAAGAAGAGTCTCCTACTGAAGAAGGCGGTTCCGGTAGCGACGGCATCTTGCCGGCC
CCTGAAGCCCCGAAAGGTCGTAATATTGACTTGTTCTTGAAAGGCATTCGCACGGCGGAA
ACCGATATTCCGAAAACCGGCGAAGCTCACTACACCGGTACCTGGGAAGCCCGCATCGGC
AAACCGATCCAATGGGACAACCAAGCCGACAAAGAAGCTGCTAAAGCTGTGTTTACCGTT
GACTTCGGCAAAAAATCCATTTCTGGTACCTTGACCGAAGAGAACGGCGTCGAACCCGCG
TTCCACATTGAAAACGGCAAAATCGAAGGCAACGGTTTTTATGCGACCGCCCGTACTCGC
GAGAATGGCATTAATTTGTCTGGCAACGGCTCCACAGATCCGAAAACCTTTCAAGCCTCG
AACTTGCGCGTAGAAGGCGGCTTCTACGGCCCACAAGCAGAAGAGCTGGGTGGTATCATC
TTCAACAACGACGGCAAAGCCTGGGCATTACCGAGGGCACTGAAAACAAAGTGGACGTA
GAAGCTGAAGTTGATGCTGAAGTTGATGTCGGCAAGCAATTGGAGAGCGAAGTAAAACAC
CAGTTTGGTGTCGTCTTCGGTGCCAAAAAAGACATGCAGGAAGTCGAGAAATGA
```

FIG. 34

LbpA(nmb1540)

ATGAACAAAAAACACGGCTTTCCGTTGACTCTTACCGCCTTGGCTATCGCCACCGCCTTT
CCGGCTTACGCTGCTCAAGCCGGCGGCGCCACTCCTGACGCAGCGCAAACCCAGTCTCTG
AAAGAAATTACCGTACGTGCTGCTAAAGTAGGTCGCCGCAGCAAAGAAGCTACCGGCTTG
GGCAAAATCGTTAAACCTCCGAAACCCTCAACAAAGAACAAGTTCTGGGCATTCGCGAC
CTGACTCGCTACGATCCTGGTGTTGCCGTAGTCGAACAAGGTAATGGCGCCTCGGGCGGT
TATAGCATCCGTGGCGTAGATAAAAACCGTGTCGCAGTTAGCGTTGATGGTGTTGCCCAA
ATCCAAGCATTTACCGTGCAAGGTTCCTTGTCCGGCTACGGTGGTCGCGGCGGTTCCGGC
GCCATCAATGAAATCGAATACGAAAACATATCCACTGTAGAGATTGATAAAGGTGCAGGT
TCCAGCGATCACGGTTCTGGCGCACTGGGTGGCGCTGTTGCATTCCGCACAAAAGAAGCC
GCCGACTTGATTAGCGACGGCAAAAGCTGGGGTATTCAAGCCAAAACTGCCTACGGCTCT
AAGAACCGTCAATTCATGAAAAGCTTGGGTGCTGGCTTTTCCAAAGATGGTTGGGAAGGT
CTGCTGATCCGCACTGAACGTCAAGGTAGGGAAACCCGTCCGCACGGTGACATTGCTGAT
GGCGTTGAATACGGCATTGACCGTCTGGACGCCTTCCGCCAAACCTACGATATCAAACGC
AAAACCAGAGAGCCCTTCTTTTCTGTCGAAGGTGAGCGCGAATCAAAACCTGTCGCCAAA
CTGGCAGGCTACGGTAAATACCTGAACAATCAATTGAACCGTTGGGTTAAAGAACGTATT
GAACAAAATCAGCCCCTGTCTGCAGAAGAAGAGGCTCAAGTCCGCGAAGCACAAGCTCGT
CACGAAAACTTGAGCGCACAAGCCTACACCGGCGGACGCATTTTGCCTGACCCTATG
GATTATCGCTCCGGCAGCTGGTTGGCCAAGCTCGGCTACCGTTTTGGTGGCCGCCACTAC
GTTGGTGGTGTTTTCGAAGACACGAAGCAACGTTATGATATCCGCGACATGACTGAAAAA
CAATACTATGGCACCGATGAAGCCGAGAAATTTCGTGATAAATCCGGCGTATATGACGGC
GATGATTTCCGTGACGGTTTGTACTTCGTTCCGAACATCGAAGAATGGAAAGGCGATAAA
AATTTGGTGCGTGGCATTGGTTTGAAATATTCTCGCACCAAATTCATTGATGAACACCAC
CGTCGTCGTCGTATGGGTCTGCTGTATCGCTACGAAAATGAAGCCTACTCCGACAATTGG
GCGGATAAAGCCGTTTTGTCCTTCGATAAGCAGGGTGTTGCTACCGATAACAATACCCTC
AAACTGAACTGCGCTGTTTACCCCGCTGTGGATAAATCTTGCCGTGCCTCAGCCGACAAA
CCATACTCTTACGACTCCAGCGATCGCTTCCACTACCGCGAACAACACAACGTTTTGAAC
GCGTCTTTCGAAAAATCTTTGAAAAACAAATGGACTAAACATCACTTGACCCTGGGTTTT
GGTTACGACGCATCTAAAGCTATCAGCCGTCCGGAACAATTGAGCCATAACGCCGCCGG
ATTTCCGAAAGCACCGGTTTCGATGAAAATAACCAGGACAAATACTTGTTGGGCAAGCCT
GAGGTCGTGGAAGGCTCAGTCTGCGGCTACATTGAAACCTTGCGCTCTCGTAAATGTGTT
CCTCGCAAAATCAATGGTTCTAACATCCACATCAGCTTGAACGATCGTTTCTCCATCGGC
AAATACTTTGACTTCAGCCTGGGCGGCCGTTACGACCGCAAAAACTTCACTACGTCCGAG
GAGCTGGTACGTTCCGGCCGCTATGTTGACCGTAGCTGGAATTCAGGCATTTTGTTCAAA
CCGAATCGCCACTTCAGCGTTAGCTACCGCGCGTCGTCCGGCTTTCGCACCCCGAGCTTC
CAAGAACTCTTCGGTATTGATATTTACCACGACTACCCTAAAGGCTGGCAACGCCCGGCG
TTGAAATCCGAAAAAGCAGCTAATCGCGAAATCGGCTTGCAATGGAAAGGCGACTTCGGT
TTCCTGGAAATCTCCTCTTTCCGCAACCGTTACACGGATATGATCGCAGTCGCAGACCAC
AAAACCAAACTGCCGAACCAAGCCGGCCAACTGACCGAAATTGATATCCGCGACTACTAT
AACGCACAAAACATGTCATTGCAAGGTGTTAATATCCTGGGCAAAATCGACTGGAATGGC
GTCTATGGCAAATTGCCGGAAGGCCTCTATACGACCCTGGCTTATAACCGCATCAAACCG
AAAAGCGTGTCCAACCGCCCTGGGTTGTCCCTGCGCTCCTACGCACTGGACGCCGTACAA
CCATCGCGCTACGTACTGGGCTTCGGCTACGACCAACCCGAAGGCAAATGGGAGCGAAC
ATCATGTTGACTTACAGTAAGGGTAAAAACCCAGACGAATTGGCTTATCTGGCGGGCGAC
CAAAAACGCTATTCCACCAAGCGCGCCAGCAGCAGCTGGAGCACAGCCGACGTGTCAGCA
TACTTGAACCTGAAAAAACGCTTGACCTTGCGCGCTGCCATTTATAACATCGGTAATTAT
CGCTATGTGACCTGGGAAAGCCTGCGCCAAACCGCTGAAAGCACCGCTAACCGCCACGGC
GGCGATAGCAATTACGGTCGTTATGCTGCCCCTGGTCGTAATTTCTCCCTGGCACTGGAA
ATGAAATTCTAA

FIG. 35

Opacity protein (Class 5,nmb1053)

ATGAAAAAGACCGTTTTTACCTGTGCCATGATTGCACTGACCGGTACCGCTGCG
GCCGCCCAGGAATTGCAAACCGCGAACGAATTCACCGTTCATACTGACCTCTC
TTCTATTTCCTCCACTCGTGCCTTCTTGAAAGAAAAACACAAAGCAGCCAAACA
CATCTCTGTACGCGCCGACATTCCTTTCGATGCCAATCAAGGTATTCGCCTGGA
AGCCGGTTTTGGTCGCTCCAAAAAAAACATTATCAATCTGGAAACCGACGAAAA
CAAGCTGGGCAAAACTAAAAACGTAAAACTGCCCACCGGTGTACCCGAAAATC
GTATCGACCTTTACACCGGTTACACCTATACACAGACCCTCAGCGACTCCTTGA
ACTTCCGCGTTGGTGCAGGCTTGGGCTTTGAGTCTTCCAAGGACTCGATCAAA
ACTACCAAACACACCCTCCACTCCTCTCGTCAGTCATGGTTGGCCAAAGTACAC
GCCGATCTGTTGTCCCAATTGGGCAACGGCTGGTATATTAACCCTTGGTCTGAG
GTTAAATTCGACTTGAACTCTCGCTACAAATTGAACACAGGCGTCACAAACCTG
AAAAAAGACATTAACCAAAAAACAAACGGCTGGGGCTTCGGCTTGGGCGCCAA
CATTGGCAAAAAACTGGGCGAAAGCGCTTCCATCGAGGCCGGTCCGTTCTACA
AACAACGTACCTACAAAGAATCCGGTGAATTCTCTGTCACTACTAAATCCGGAG
ACGTATCTTTGACAATCCCTAAAACTTCCATCCGCGAGTATGGCTTGCGCGTCG
GCATCAAATTTTGA

FIG. 36

NadA (nmb1994)

```
ATGTCCATGAAACACTTCCCGTCCAAAGTTTTGACCACCGCCATCTTGGCCACC
TTCTGCTCCGGCGCCTTGGCCGCCACCTCCGACGACGACGTTAAAAAAGCCGC
CACCGTTGCCATCGTTGCCGCCTACAACAACGGCCAAGAAATCAACGGCTTCA
AAGCCGGCGAAACCATCTACGACATCGGCGAAGACGGCACCATCACCCAAAAA
GACGCCACCGCCGCCGACGTTGAAGCCGACGACTTCAAAGGCTTGGGCTTGA
AAAAAGTTGTTACCAACTTGACCAAAACCGTTAACGAAAACAAACAAAACGTTG
ACGCCAAAGTTAAAGCCGCCGAATCCGAAATCGAAAAATTGACCACCAAATTGG
CCGACACCGACGCCGCCTTGGCCGACACCGACGCCGCCTTGGACGAAACCAC
CAACGCCTTGAACAAATTGGGCGAAAACATCACCACCTTCGCCGAAGAAACCA
AAACCAACATCGTTAAAATCGACGAAAAATTGGAAGCCGTTGCCGACACCGTTG
ACAAACACGCCGAAGCCTTCAACGACATCGCCGACTCCTTGGACGAAACCAAC
ACCAAAGCCGACGAAGCCGTTAAAACCGCCAACGAAGCCAAACAAACCGCCGA
AGAAACCAAACAAAACGTTGACGCCAAAGTTAAAGCCGCCGAAACCGCCGCCG
GCAAAGCCGAAGCCGCCGCCGGCACCGCCAACACCGCCGCCGACAAAGCCG
AAGCCGTTGCCGCCAAAGTTACCGACATCAAAGCCGACATCGCCACCAACAAA
GCCGACATCGCCAAAAACTCCGCCCGCATCGACTCCTTGGACAAAAACGTTGC
CAACTTGCGCAAAGAAACCCGCCAAGGCTTGGCCGAACAAGCCGCCTTGTCC
GGCTTGTTCCAACCGTACAACGTTGGCCGCTTCAACGTTACCGCCGCCGTTGG
CGGCTACAAATCCGAATCCGCCGTTGCCATCGGCACCGGCTTCCGCTTCACCG
AAAACTTCGCCGCCAAAGCCGGCGTTGCCGTTGGCACCTCCTCCGGCTCCTCC
GCCGCCTACCACGTTGGCGTTAACTACGAATGGTAA
```

FIG. 37

PorA (nmb1429)

ATGCGCAAAAAATTGACCGCCTTGGTTTTGTCCGCCTTGCCGTTGGCCGCCGT
TGCCGACGTTTCCTTGTACGGCGAAATCAAAGCCGGCGTTGAAGGCCGCAACT
ACCAATTGCAATTGACCGAAGCCCAAGCCGCCAACGGCGGCGCCTCCGGCCA
AGTTAAAGTTACCAAAGTTACCAAAGCCAAATCCCGCATCCGCACCAAAATCTC
CGACTTCGGCTCCTTCATCGGCTTCAAAGGCTCCGAAGACTTGGGCGACGGCT
TGAAAGCCGTTTGGCAATTGGAACAAGACGTTTCCGTTGCCGGCGGCGGCGC
CACCCAATGGGGCAACCGCGAATCCTTCATCGGCTTGGCCGGCGAATTCGGC
ACCTTGCGCGCCGGCCGCGTTGCCAACCAATTCGACGACGCCTCCCAAGCC
ATCGACCCGTGGGACTCCAACAACGACGTTGCCTCCCAATTGGGCATCTTCAA
ACGCCACGACGACATGCCGGTTTCCGTTCGCTACGACTCCCCGGAATTCTCCG
GCTTCTCCGGCTCCGTTCAATTCGTTCCGATCCAAAACTCCAAATCCGCCTACA
CCCCGGCCTACTACACCAAAAACACCAACAACAACTTGACCTTGGTTCCGGCC
GTTGTTGGCAAACCGGGCTCCGACGTTTACTACGCCGGCTTGAACTACAAAAA
CGGCGGCTTCGCCGGCAACTACGCCTTCAAATACGCCCGCCACGCCAACGTT
GGCCGCAACGCCTTCGAATTGTTCTTGATCGGCTCCGGCTCCGACCAAGCCAA
AGGCACCGACCCGTTGAAAAACCACCAAGTTCACCGCTTGACCGGCGGCTACG
AAGAAGGCGGCTTGAACTTGGCCTTGGCCGCCCAATTGGACTTGTCCGAAAAC
GGCGACAAAACCAAAAACTCCACCACCGAAATCGCCGCCACCGCCTCCTACCG
CTTCGGCAACGCCGTTCCGCGCATCTCCTACGCCCACGGCTTCGACTTCATCG
AACGCGGCAAAAAGGCGAAAACACCTCCTACGACCAAATCATCGCCGGCGTT
GACTACGACTTCTCCAAACGCACCTCCGCCATCGTTTCCGGCGCCTGGTTGAA
ACGCAACACCGGCATCGGCAACTACACCCAAATCAACGCCGCCTCCGTTGGCT
TGCGCCACAAATTCTAA

FIG. 38 feta (nmb1988)

ATGAACACCCCGTTGTTCCGCTTGTCCTTGTTGTCCTTGACCTTGGCCGCCGGCTTCGCCCACG
CCGCCGAAAACAACGCCAAAGTTGTTTTGGACACCGTTACCGTTAAAGGCGACCGCCAAGGCTC
CAAAATCCGCACCAACATCGTTACCTTGCAACAAAAAGACGAATCCACCGCCACCGACATGCGC
GAATTGTTGAAAGAAGAACCGTCCATCGACTTCGGCGGCGGCAACGGCACCTCCCAATTCTTGA
CCTTGCGCGGCATGGGCCAAAACTCCGTTGACATCAAAGTTGACAACGCCTACTCCGACTCCCA
AATCTTGTACCACCAAGGCCGCTTCATCGTTGACCCGGCCTTGGTTAAAGTTGTTTCCGTTCAAA
AAGGCGCCGGCTCCGCCTCCGCCGGCATCGGCGCCACCAACGGCGCCATCATCACCAAAACC
GTTGACGCCCAAGACTTGTTGAAAGGCTTGGACAAAAACTGGGGCGTTCGCTTGAACTCCGGCT
TCGCCTCCAACGAAGGCGTTTCCTACGGCGCCTCCGTTTTCGGCAAAGAAGGCAACTTCGACG
GCTTGTTCTCCTACAACCGCAACAACGAAAAAGACTACGAAGCCGGCAAAGGCTTCCGCAACAA
CTTCAACGGCGGCAAAACCGTTCCGTACTCCGCCTTGGACAAACGCTCCTACTTGGCCAAAATC
GGCACCTCCTTCGGCGACGGCGACCACCGCATCGTTTTGTCCCACATGAAAGACCAACACCGC
GGCATCCGCACCGTTCGCGAAGAATTCACCGTTGGCGGCGACAAAGAACGCATCTCCATGGAA
CGCCAAGCCCCGGCCTACCGCGAAACCACCCAATCCAACACCAACTTGGCCTACACCGGCAAA
AACTTGGGCTTCGTTGAAAAATTGGACGCCAACGCCTACGTTTTGGAAAAAGAACGCTACTCCG
CCGACGACTCCGGCACCGGCTACGCCGGCAACGTTAAAGGCCCGAACCACACCCAAATCACCA
CCCGCGGCATGAACTTCAACTTCGACTCCCGCTTGGCCGAACAAACCTTGTTGAAATACGGCAT
CAACTACCGCCACCAAGAAATCAAACCGCAAGCCTTCTTGAACTCCCAATTCAAAATCGAAGACA
AAGAAAAAGCCACCGACGAAGAAAAAAACAAAAACCGCGAAAACGAAAAAATCGCCAAAGCCTA
CCGCTTGACCAACCCGACCAAAACCGACACCGGCGCCTACATCGAAGCCATCCACGAAATCGA
CGGCTTCACCTTGACCGGCGGCTTGCGCTACGACCGCTTCAAAGTTAAAACCCACGACGGCAAA
ACCGTTTCCTCCAACAACTTGAACCCGTCCTTCGGCGTTATCTGGCAACCGCACGAACACTGGT
CCTTCTCCGCCTCCCACAACTACGCCTCCCGCTCCCCGCGCTTGTACGACGCCTTGCAAACCCA
CGGCAAACGCGGCATCATCTCCATCGCCGACGGCACCAAAGCCGAACGCGCCCCGCAACACCGA
AATCGGCTTCAACTACAACGACGGCACCTTCGCCGCCAACGGCTCCTACTTCTGGCAAACCATC
AAAGACGCCTTGGCCAACCCGCAAAACCGCCACGACTCCGTTGCCGTTCGCGAAGCCGTTAAC
GCCGGCTACATCAAAAACCACGGCTACGAATTGGGCGCCTCCTACCGCACCGGCGGCTTGACC
GCCAAAGTTGGCGTTTCCCACTCCAAACCGCGCTTCTACGACACCCACAAAGACAAATTGTTGT
CCGCCAACCCGGAATTCGGCGCCCAAGTTGGCCGCACCTGGACCGCCTCCTTGGCCTACCGCT
TCCAAAACCCGAACTTGGAAATCGGCTGGCGCGGCCGCTACGTTCAAAAAGCCGTTGGCTCCAT
CTTGGTTGCCGGCCAAAAAGACCGCAACGGCAAATTGGAAAACGTTGTTCGCAAAGGCTTCGGC
GTTAACGACGTTTTCGCCAACTGGAAACCGTTGGGCAAAGACACCTTGAACGTTAACTTGTCCGT
TAACAACGTTTTCAACACCTTCTACTACCCGCACTCCCAACGCTGGACCAACACCTTGCCGGGC
GTTGGCCGCGACGTTCGCTTGGGCGTTAACTACAAATTCTAA

ENGINEERED SEQUENCES TO FACILITATE EXPRESSION OF ANTIGENS IN *NEISSERIA* AND METHODS OF USE

CROSS REFERENCE TO RELATED APPLICATIONS

This application claims priority benefit of U.S. Provisional Patent Application Ser. No. 61/529,776, filed Aug. 31, 2011, which application is incorporated herein by reference in its entirety.

STATEMENT REGARDING FEDERALLY SPONSORED RESEARCH

This invention was made with government support under Grant No. AI 046464, and AI 082263, awarded by the National Institutes of Health. The government has certain rights in the invention.

INTRODUCTION

In order to ensure effective colonization and transmission, meningococcus bacteria adapt and respond to different microenvironments through differential expression of genes involved in pathogenesis. In *Neisseria meningitidis*, the presence or absence of pathogenic determinants is regulated at the transcriptional level, while more fine-tuning of the determinant level can be made at both transcriptional and translational levels. Gene activation is typically associated with reversible changes within simple DNA sequence tracts (repeats in some instances) located in promoter, coding, and/or transcription terminator sequence regions. The number of repeats can be modified during replication through mechanisms such as slipped strand mis-pairing, and can consequently influence transcription or translation by introducing frame-shift mutations or changing critical promoter spacing. The loss or gain of repeat units results in high frequency on-off switching (in the case of frame-shift/translational control) or modulation of the level (in the case of promoter control) of expression of genes typically associated with surface antigens.

PorA is an example of a surface antigen whose promoter strength is regulated at least partially by changes in a poly-G tract that is located between base pairs −35 and −10 relative to the transcription start site. NadA is an example of a surface antigen whose promoter strength is regulated in part by phase variation. A tract of repeated TAAA sequences, located upstream of the nadA promoter, together with the binding of nadR transcriptional repressor to three different operator elements, dictates the frequency of phase variation of nadA. Over-expressing a surface antigen from a strong native promoter in a *Neisseria meningitidis* host therefore presents difficulties when producing vaccines, as these mechanisms can result in inconsistent expression of surface antigens.

SUMMARY

The present disclosure generally provides engineered polynucleotide sequences that facilitate high-level expression of one or more gene products (e.g., polypeptides) of interest in *Neisseria meningitidis*. Methods of use of such sequences, e.g., use in vaccine production, are also provided.

In some embodiments, an engineered polynucleotide sequence is a promoter, including a 5' portion of a native *N. meningitidis* porA promoter comprising the sequence ATG-GTT, (SEQ ID NO: 2), a spacer portion, and a 3' portion of a native *N. meningitidis* porA promoter comprising the sequence TATAAT (SEQ ID NO: 3), wherein the spacer comprises a sequence of the formula $N^1$-TTTCA-$N^2$, (SEQ ID NO: 1), wherein $N^1$ is $X^a$(T/A)(T/A)(T/A)(T/G)(C/G)(C/G)(C/G/A)(G/T) $CX^b$ and $N^2$ is $X^c X^d X^e$, wherein: $X^a$ is present or absent, and when present is T or A, $X^b$ is present or absent, and when present is A or C, $X^c$ is present or absent, and when present is T or G, $X^d$ is present or absent, and when present is A or G; and $X^e$ is present or absent, and when present is G wherein the 5' portion, the spacer, and the 3' portion are operably linked to provide for transcription in *N. meningitidis*.

In some embodiments, the spacer comprises the sequence ATATGCCTCCTTTCATA (SEQ ID NO: 4). In some embodiments, the spacer comprises the sequence TATATGC-CTCCTTTCATA (SEQ ID NO: 5). In some embodiments, the spacer comprises the sequence ATAATGCCTC-CTTTCATA (SEQ ID NO: 6). In some embodiments, the spacer comprises the sequence ATATGCATCATTTCATA (SEQ ID NO: 7). In some embodiments, the spacer comprises the sequence TTTTGCGGGCTTTCATA (SEQ ID NO: 8) In some embodiments, the spacer comprises the sequence TTTTGCGGGCTTTCAGGG (SEQ ID NO: 9). In some embodiments, the spacer comprises the sequence TTTTGCGGGCTTTCAG(SEQ ID NO: 10).

In some embodiments, an engineered polynucleotide sequence is a promoter comprising the formula, from 5' to 3': TFB-X-E-ATG, wherein TFB refers to a transcription factor binding sequence of a native nmb1523 promoter; E refers to a 66 base pair extension sequence of a native nmb1523 promoter; and X refers to a spacer sequence of a native nmb1523 promoter positioned between TFB and E, wherein portions TFB, X, and E are operably linked to provide for transcription in *N. meningitidis*, with the proviso that when E is present, TFB is absent, and when TFB is present, E is absent. In certain embodiments, both TFB and E are absent.

In some embodiments, an engineered polynucleotide sequence is a nucleic acid construct comprising the promoter described above operably linked to a polynucleotide sequence encoding a *Neisseria meningitidis* surface antigen.

In some embodiments, an isolated *Neisseria meningitidis* bacterium comprises a promoter described above, or a nucleic acid construct described above. In some embodiments, an isolated *Neisseria meningitidis* bacterium comprises a promoter that is operably positioned in the genome of the bacterium to facilitate expression of an endogenous polynucleotide. In some embodiments, the endogenous polynucleotide encodes a *Neisseria meningitidis* surface antigen.

Some embodiments relate to a method of expressing a *Neisseria meningitidis* surface antigen, the method comprising: culturing an isolated *Neisseria meningitidis* bacterium as described above, wherein said culturing facilitates expression of the surface antigen.

Some embodiments relate to a method of expressing a *Neisseria meningitidis* surface antigen, the method comprising operably inserting a promoter sequence as described above into the genome of a *Neisseria meningitidis* host upstream of a native surface antigen gene, and culturing the *Neisseria meningitidis* host, wherein said culturing facilitates expression of the surface antigen.

Some embodiments relate to a method of expressing a *Neisseria meningitidis* surface antigen, the method comprising inserting a nucleic acid construct comprising a promoter sequence as described above operably linked to a polynucleotide sequence encoding a surface antigen into the genome of a *Neisseria meningitidis* host; and culturing the *Neisseria meningitidis* host, wherein said culturing facilitates expression of the surface antigen.

mutant isolates measured by quantitative Western blot. Panels B and C show flow cytometry data.

Figure 14:
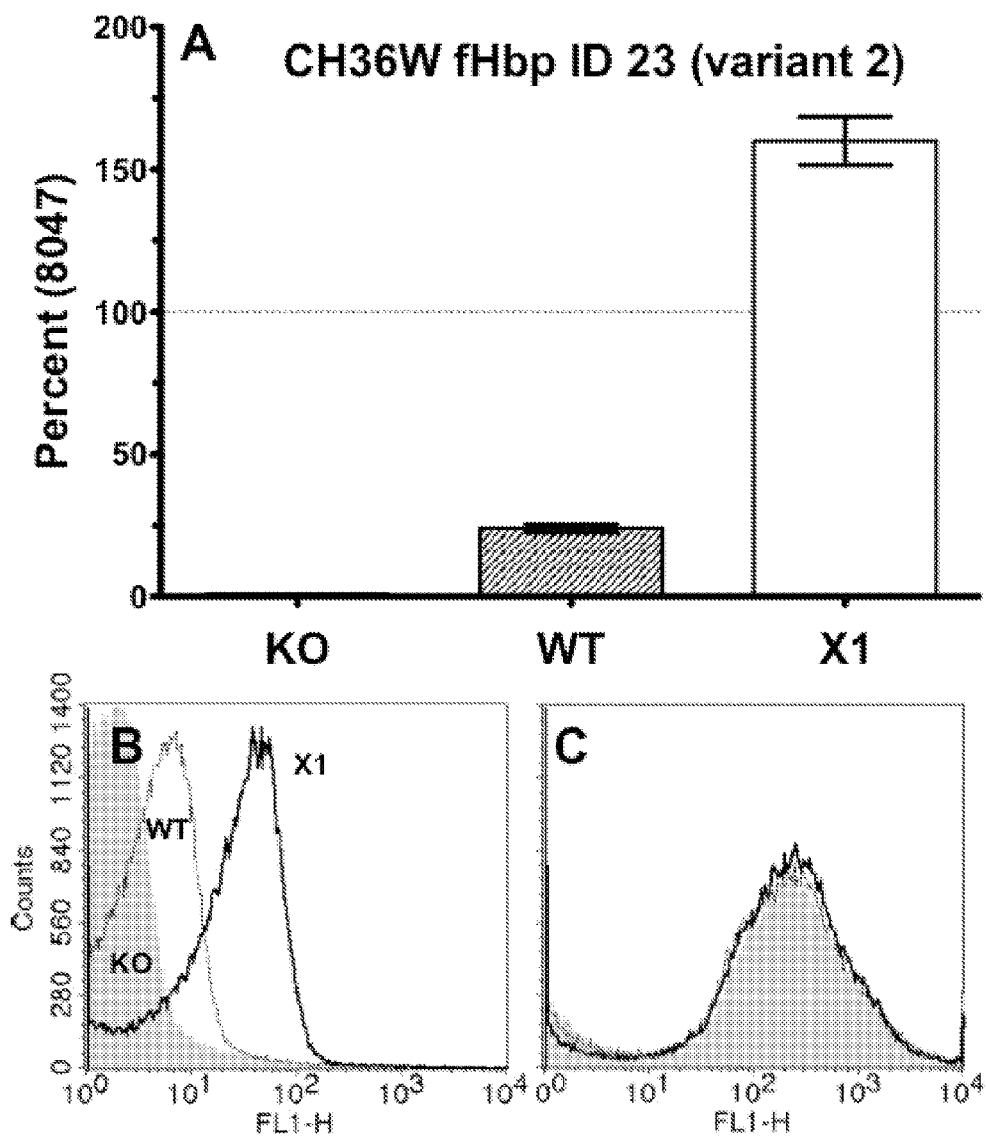

FIG. 14: Panel A shows quantitative Western blot data of expression levels in CH36W mutants. Panels B and C show flow cytometry data.

Figure 15:
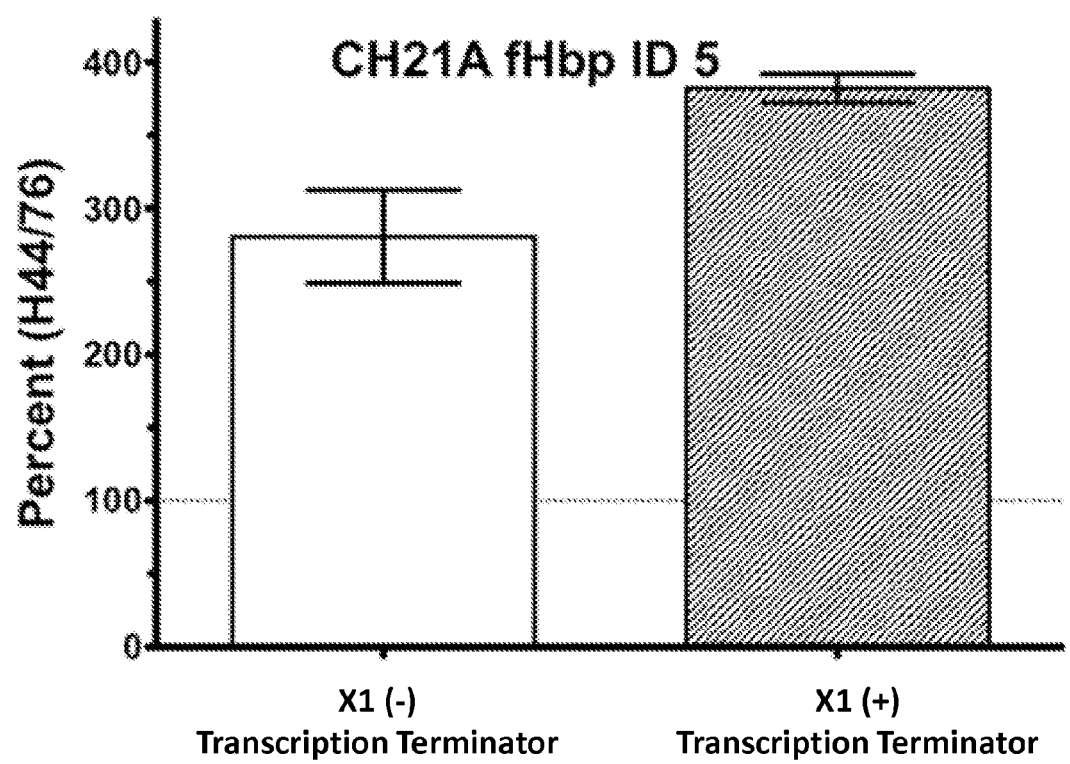
Figure 39:
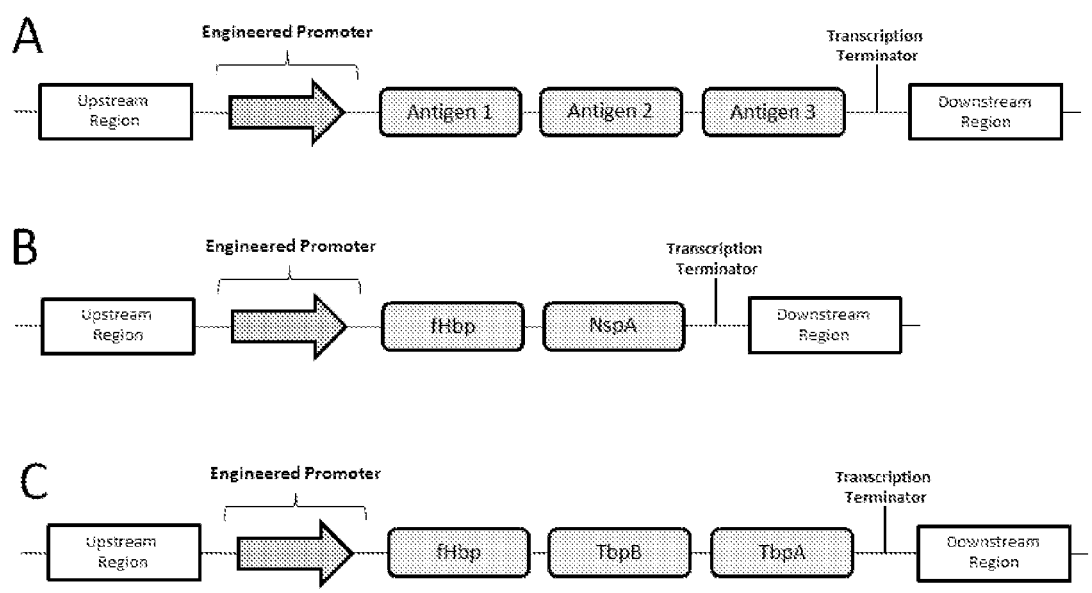
Figure 40:
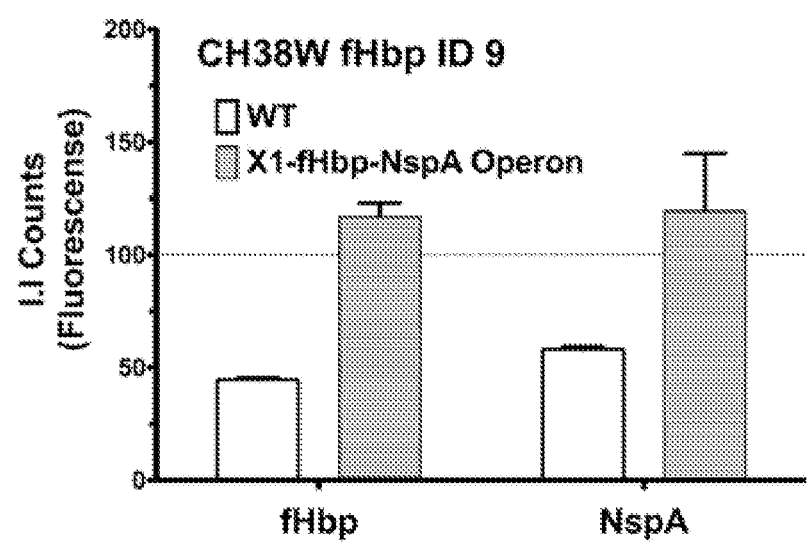

FIG. 15 shows the expression levels of fHbp ID 5 in the CH21A strain with and without a transcription terminator sequence.

FIG. 16 is a table showing the frequency of codon usage in a *Neisseria meningitidis* FAM18 strain.

FIG. 17 is a table showing the frequency of codon usage in a *Neisseria meningitidis* Z2491 strain.

FIG. 18 is a sequence comparison between a codon-optimized sequence and an original sequence for fHbp ID 9(SEQ ID NOs: 28-29). Optimized codons are shown in grey.

FIG. 19 is a codon-optimized sequence of fHbp ID 23 (SEQ ID NO: 30).

FIG. 20 is a codon-optimized sequence of fHbp ID 4 (SEQ ID NO: 31).

FIG. 21 is a codon-optimized sequence of fHbp ID 28 (SEQ ID NO: 32).

FIG. 22 is a codon-optimized sequence of fHbp ID 1 (SEQ ID NO: 33).

FIG. 23 is a codon-optimized sequence of fHbp ID 14 (SEQ ID NO: 34).

FIG. 24 is a codon-optimized sequence of fHbp ID 45 (SEQ ID NO: 35).

FIG. 25 is a codon-optimized sequence of fHbp ID 55 (SEQ ID NO: 36).

FIG. 26 is a codon-optimized sequence of fHbp ID 19 (SEQ ID NO: 37).

FIG. 27 is a codon-optimized sequence of fHbp ID 77 (SEQ ID NO: 38).

FIG. 28 is a codon-optimized sequence of NspA (nmb0663) (SEQ ID NO: 39).

FIG. 29 is a codon-optimized sequence of NspA (nmc0612, nma0862) (SEQ ID NO: 40).

FIG. 30 is a codon-optimized sequence of NHbp (nmb2132) (SEQ ID NO: 41).

FIG. 31 is a codon-optimized sequence of TbpB (Tbp2, nmb0461) (SEQ ID NO: 42).

FIG. 32 is a codon-optimized sequence of TbpA (Tbp1, nmb0461) (SEQ ID NO: 43).

FIG. 33 is a codon-optimized sequence of LbpB (nmb1541) (SEQ ID NO: 44).

FIG. 34 is a codon-optimized sequence of LbpA (nmb1540) (SEQ ID NO: 45).

FIG. 35 is a codon-optimized sequence of Opacity protein (Class 5, nmb1053) (SEQ ID NO: 46).

FIG. 36 is a codon-optimized sequence of NadA (nmb1994) (SEQ ID NO: 47).

FIG. 37 is a codon-optimized sequence of PorA (nmb1429) (SEQ ID NO: 48).

FIG. 38 is a codon-optimized sequence of feta (nmb1988) (SEQ ID NO: 49).

FIG. 39: Panel A is a schematic illustration of an engineered promoter driving expression of up to three different polynucleotide sequences that encode surface antigens, and including a transcription terminator sequence located downstream of the surface antigen-encoding sequences. Panel B is a schematic illustration of an engineered promoter driving expression of fHbp and NspA, and including a transcription terminator located downstream of the surface antigen-encoding sequences. Panel C is a schematic illustration of an engineered promoter driving expression of fHbp, TbpB, and TbpA, and including a transcription terminator located downstream of the surface antigen-encoding sequences.

FIG. 40 shows quantitative Western blot data of expression levels of both fHbp and NspA surface antigen sequences in a CH38W mutant *Neisseria meningitidis* strain, wherein expression of both of the surface antigen sequences is driven by a single engineered promoter.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporAted herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "the promoter" includes reference to one or more promoters, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The following terms have the following meanings unless otherwise indicated. Any undefined terms have their art recognized meanings.

"Polynucleotide" as used herein refers to an oligonucleotide, nucleotide, and fragments or portions thereof, and to DNA or RNA of genomic or synthetic origin which can be single- or double-stranded, and represent the sense or antisense strand.

"Promoter" refers to a DNA regulatory region having a sequence capable of initiating transcription of a downstream (3' direction) sequence.

"Transcriptional terminator" refers to a DNA regulatory region capable of terminating transcription of an upstream (5' direction) sequence.

A "codon" is a series of three contiguous nucleotides that encode a specific amino acid residue in a polypeptide chain or encode the termination of translation (e.g. a "stop" codon).

"Translationally optimized sequence" refers to a non-natural DNA sequence wherein the codons have been altered based on the preferences of the organism expressing the sequence for one of the several codons that encode the same amino acid in order to facilitate more efficient expression of the DNA sequence.

A "deletion" is defined as a change in nucleotide sequence in which one or more nucleotide bases are absent as compared to a nucleotide sequence of a naturally occurring reference polynucleotide.

An "insertion" or "addition" is that change in a nucleotide sequence which has resulted in the addition of one or more nucleotide bases as compared to a nucleotide sequence of a naturally occurring reference polynucleotide.

A "substitution" results from the replacement of one or more nucleotides by different nucleotides as compared to a nucleotide sequence of a naturally occurring reference polynucleotide.

By "construct" or "polynucleotide construct" is meant a nucleic acid sequence that has been constructed to comprise one or more functional units not found together in nature.

By "operably linked" is meant that a DNA sequence and a regulatory sequence (e.g. a promoter) are connected in such a way as to permit gene expression when the appropriate molecules (e.g., transcriptional activator proteins) are bound to the regulatory sequence. Operably linking a DNA sequence and a regulatory sequence can be accomplished by operably inserting the regulatory sequence upstream (e.g. in the 5' direction) of the DNA sequence, or by operably inserting the DNA sequence downstream (e.g. in the 3' direction) of the regulatory sequence.

The term "endogenous" refers to any naturally-occurring component of a cell.

The term "exogenous" refers to any non-naturally-occurring component of a cell that originates outside the cell.

The term "heterologous" or "chimeric" refers to two components that are defined by structures derived from different sources. For example, where "heterologous" is used in the context of a chimeric promoter, the chimeric promoter can include operably linked nucleotide sequences that can be derived from different polynucleotide reference sequences (e.g., a first component from an alpha and a second component from a beta reference nucleotide sequence). A chimeric polynucleotide containing two or more defined segments, each of which is from a different reference sequence, can be naturally-occurring or man-made (non-naturally-occurring). Non-naturally occurring chimeric polynucleotide sequence refers to "man-made chimeras" and may encompass, e.g., a promoter with heterologous components that are not found together in nature.

Other exemplary "heterologous" nucleic acids include expression constructs in which a nucleic acid comprising a coding sequence is operably linked to a regulatory element (e.g., a promoter) that has a genetic origin different from that of the coding sequence (e.g., to provide for expression in a host cell of interest, which may be of different genetic origin relative to the promoter, the coding sequence or both). For example, a chimeric promoter operably linked to a polynucleotide encoding an fHbp polypeptide or domain thereof is said to be a heterologous nucleic acid.

"Domain deletion promoter" as used herein refers to a polynucleotide promoter sequence that is derived from a native promoter sequence, but in which one or more domains (e.g. a transcription factor binding domain and/or a base pair extension domain) has been deleted.

"Recombinant" as used herein refers to a nucleic acid encoding a gene product, a gene product (e.g., polypeptide) encoded by such a nucleic acid, or a cell (e.g. a bacterial cell) that has been manipulated by the hand of man, and thus is provided in a context or form in which it is not found in nature. "Recombinant" thus encompasses, for example, a polynucleotide sequence encoding a gene product operably linked to a heterologous promoter (such that the construct that provides for expression of the gene product from an operably linked promoter is not found in nature). For example, a "recombinant fHbp" encompasses an fHbp encoded by a construct that provides for expression from a promoter heterologous to the fHbp coding sequence, fHbp polypeptides that are modified relative to a naturally-occurring fHbp (e.g., as in a fusion protein), and the like. It should be noted that a recombinant fHbp polypeptide can be endogenous to or heterologous to a *Neisseria meningitidis* strain in which such a recombinant fHbp-encoding construct is present. A recombinant organism (e.g. a recombinant bacterium) can be created by incorporating exogenous DNA into an organism to achieve a permanent or transient genetic change. Genetic change can be accomplished either by incorporation of the exogenous DNA into the genome of the host cell, or by transient or stable maintenance of the exogenous DNA as an episomal element.

A "knock-out" or "knockout" of a target gene refers to an alteration in the sequence of the gene that results in a decrease of function of the target gene, e.g., such that target gene expression is undetectable or insignificant, and/or the gene product does not function or is not significantly functional. For example, a "knockout" of a gene involved in LPS synthesis means that function of the gene has been substantially decreased so that the expression of the gene is not detectable or is only present at insignificant levels and/or a biological activity of the gene product (e.g., an enzymatic activity) is significantly reduced relative to prior to the modification or is not detectable. "Knock-outs" encompass conditional knock-outs, where alteration of the target gene can occur upon, for example, exposure to a predefined set of conditions (e.g., temperature, osmolarity, exposure to substance that promotes target gene alteration, and the like).

As used herein, the term "isolated" is meant to describe a molecule of interest (e.g., a promoter) that is in an environment different from that in which the molecule naturally occurs. Thus, for example, "isolated" encompasses a naturally-occurring promoter that is isolated from its natural environment and operably linked to a heterologous polynucleotide sequence. "Isolated" may also include compounds that are within samples in which the compound of interest is partially or substantially purified, e.g., isolated surface antigen proteins.

"Enriched" means that a compound of interest in a sample is manipulated by an experimentalist or a clinician so that it is present in at least a three-fold greater concentration by total weight, usually at least 5-fold greater concentration, more preferably at least 10-fold greater concentration, more usually at least 100-fold greater concentration than the concentration of that antigen in the strain from which the antigen composition was obtained. Thus, e.g., if the concentration of a particular antigen is 1 microgram per gram of total bacterial preparation (or of total bacterial protein), an enriched preparation would contain at least 3 micrograms per gram of total bacterial preparation (or of total bacterial protein).

As used herein, the term "substantially purified" refers to a compound (e.g., a surface antigen) that is removed from its natural environment and is at least 60% free, preferably 75% free, and most preferably 90% free from other components with which it is naturally associated.

The term "native" when used in the context of a polynucleotide sequence (e.g. a promoter or a polynucleotide sequence encoding a surface antigen) refers to naturally-occurring sequences (e.g. naturally-occurring porA or nadA promoter sequences, or naturally-occurring fHbp-encoding sequences) as they are typically found in Neisseria meningitidis bacteria.

"Derived from" in the context of a polynucleotide sequence (e.g., a polynucleotide sequence derived from a native Neis serial promoter) is meant to indicate that the polynucleotide has a sequence that is modified relative to a reference polynucleotide, e.g., a naturally-occurring polynucleotide sequence, and is not meant to be limiting as to the source or method by which the polynucleotide is made. A polynucleotide sequence derived from another polynucleotide sequence may include, for example, multiple additions, deletions, or substitutions of specific nucleic acids.

The phrase "a disease caused by Neisseria meningitidis" encompasses any clinical symptom or combination of clinical symptoms that are present in an infection with Neisseria meningitidis bacteria. These symptoms include but are not limited to: colonization of the upper respiratory tract (e.g. mucosa of the nasopharynx and tonsils) by a pathogenic strain of Neisseria meningitidis, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "elicit an immunological response in a subject" means that there is a detectable difference between an immunological response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

A "surface antigen" is an antigen that is present in a surface structure of Neisseria meningitidis (e.g. the outer membrane, inner membrane, periplasmic space, capsule, pili, etc.).

"Serogroup" or "capsular group" as used herein refers to classification of Neisseria meningitidis by virtue of immunologically detectable variations in the capsular polysaccharide. About 12 serogroups are known: A, B, C, X, Y, Z, 29-E, W-135, H, I, K and L. Any one serogroup can encompass multiple serotypes and multiple serosubtypes.

"Serotype" as used herein refers to classification of Neisseria meningitidis strains based on monoclonal antibody defined antigenic differences in the outer membrane protein Porin B. A single serotype can be found in multiple serogroups and multiple serosubtypes.

"Serosubtype" as used herein refers classification of Neisseria meningitidis strains based on antibody defined antigenic variations on an outer membrane protein called Porin A, or upon VR typing of amino acid sequences deduced from DNA sequencing (Sacchi et al., 2000, J. Infect. Dis. 182:1169; see also the Multi Locus Sequence Typing web site). Most variability between PorA proteins occurs in two (loops I and IV) of eight putative, surface exposed loops. The variable loops I and IV have been designated VR1 and VR2, respectively. A single serosubtype can be found in multiple serogroups and multiple serotypes.

A "monovalent vaccine" refers to a vesicle vaccine prepared from a single strain. The strain may be a mutant strain (i.e., genetically modified) or a wildtype strain (naturally occurring). Such vaccines may be combined with other immunogenic or antigenic components to provide a vaccine composition (e.g., combined with one or more recombinant protein antigens).

A "bivalent vaccine" refers to a vesicle vaccine prepared from two different strains. The two strains may be mutant strains or wildtype strains or a combination of a mutant and a wildtype strain. Such vaccines may be combined with other immunogenic or antigenic components to provide a vaccine composition (e.g., combined with one or more recombinant protein antigens).

The term "subject" as used herein can refer to a human or to a non-human animal, e.g. a mammal, including humans, primates, domestic and farm animals, and zoo, sport, laboratory, or pet animals, such as horses, cows, dogs, cats, rodents, and the like.

DETAILED DESCRIPTION

The present disclosure generally provides engineered polynucleotide sequences that facilitate consistent, high-level expression of one or more gene products (e.g., polypeptides, RNA) of interest in recombinant host cells. Methods of use of such sequences, e.g., use in vaccine production, are also provided.

As described in more detail below, some of the polynucleotide sequences of the present disclosure function as promoters, while others function as transcription terminators. The polynucleotide sequences described herein may be operably linked to one or more polynucleotide sequences encoding one or more gene products (e.g., polypeptides, RNA) of interest, and the resulting construct may be introduced into host cells, e.g., Neisseria meningitidis cells, to create recombinant hosts capable of expressing the one or more gene products of interest at high levels. Polynucleotide sequences of the present disclosure that encode a protein of interest may be codon-optimized to increase expression of the protein of interest in recombinant host cells.

Engineered Promoters

Figure 3:
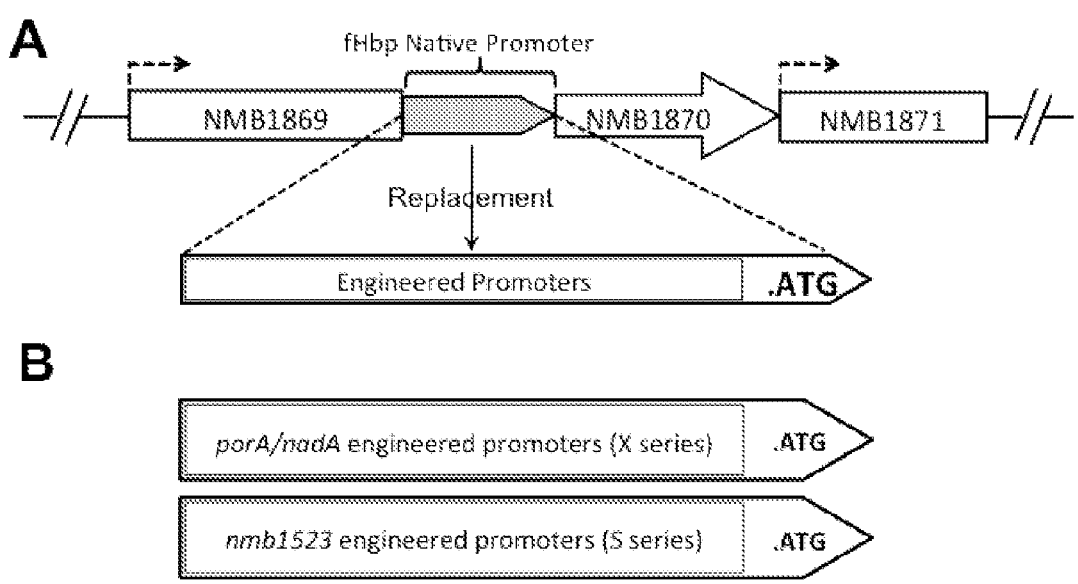

The present disclosure generally provides engineered polynucleotide sequences that can act as promoters in host cells, e.g, Neisseria cells, e.g., N. meningitidis, N. gonorrhoeae or related N. flavescens, N. lactamica, N. polysaccharea, N. cinerea, N. mucosa, N. subflava, N. sicca, N. elongata, or Haemophilus spp. The disclosed promoter sequences facilitate high-level expression of gene products (e.g., proteins of interest, e.g. surface antigens), in host cells. Engineered promoters can be, for example, chimeric promoters that incorporate sequences from two or more different native Neisserial promoters (or variants thereof). Engineered promoters may also be, for example, domain deletion promoters that are derived from a native Neisserial promoter in which one or more functional domains of the promoter have been deleted (e.g., where a transcription factor binding domain and/or a base pair extension domain have been deleted). FIG. 3 shows a diagram representing the strategy employed to identify sequences that are then subsequently tested for facilitating increased promoter output in Neisserial host strains.

The engineered promoters of the present disclosure can provide for an increase in expression of a gene product of interest to which it is operably linked of about 5%, about 10%, about 25%, about 50%, about 75%, or more relative to expression of the gene product from its native promoter. The engineered promoters of the present disclosure can provide for an increase in expression of a gene product of interest that is at least about 2-fold, about 3-fold, about 4-fold, about 5-fold, about 8-fold, about 10-fold or at least about 15-fold relative to expression of the gene product from its native promoter.

When combined with a transcription terminator of the present disclosure, the engineered promoters with the transcription terminator can provide for a further increase in expression of a gene product of interest above that provided by an engineered promoter without a transcription terminator, e.g, by at least about 5%, about 10%, about 15%, about 20%, about 25%, about 30% or more relative to the engineered promoter without the transcription terminator.

Chimeric Promoters

The engineered promoters of the present disclosure that contain combinations of native Neisserial promoter sequences (or variants thereof) are referred to herein as chimeric promoters.

In general, the chimeric promoters contain 1) a 5' portion of a native porA promoter having the contiguous nucleotide sequence ATGGTT (referred to as a "−35 region" due to its location relative to the transcription start site), 2) a spacer portion, and 3) a 3' portion of a native PorA promoter having the contiguous nucleotide sequence TATAAT (referred to as a "−10 region" due to its location relative to the transcription start site). FIGS. 1A and 1B show a schematic representation of the native NadA and PorA promoter sequences, along with their main sequence features.

Figure 4:
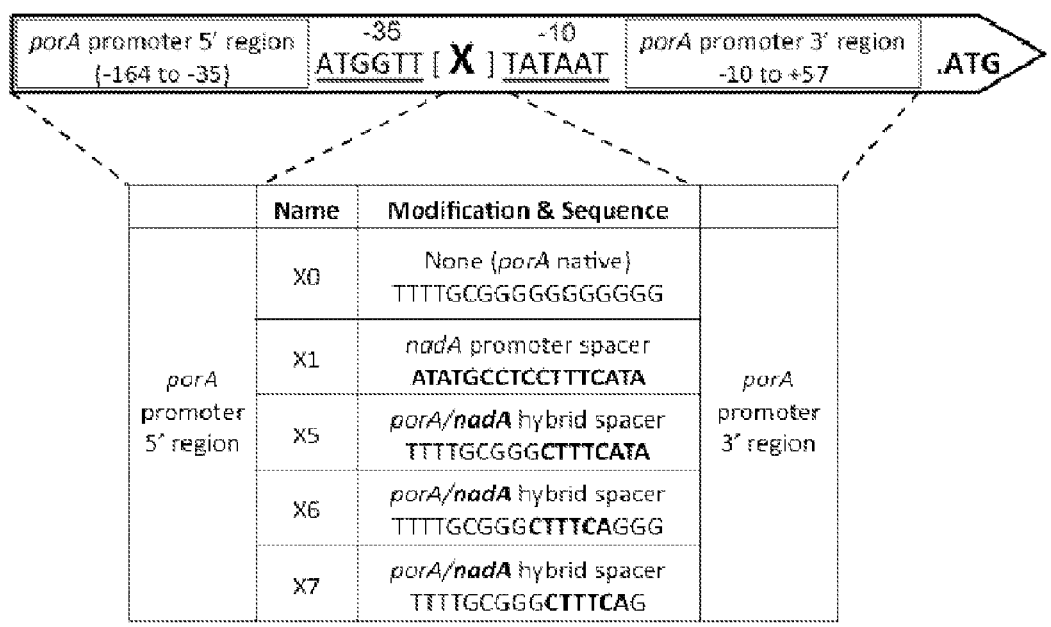

The spacer portion generally includes a 5' portion containing a sequence of 10 to 11 contiguous nucleotides derived from a native PorA and/or NadA promoter, 5 contiguous nucleotides having the sequence TTTCA, and a 3' portion containing a sequence of 1 to 3 contiguous nucleotides derived from a native PorA or NadA promoter. As used herein, the term "analogous" is used to describe a heterologous portion of a chimeric promoter that originates from the same geographical region of the reference or source promoter. For example, a sequence of 10 contiguous nucleotides located adjacent to the −35 region of a NadA promoter would be "analogous" to a sequence of 10 contiguous nucleotides located adjacent to the −35 region of a PorA promoter. FIG. 4 shows the sequence features of several of the chimeric promoters of the present disclosure.

The spacer portion of the chimeric promoters of the present disclosure, in general, has a structure of the formula, from 5' to 3':

$N^1$-TTTCA-$N^2$ (SEQ ID NO: 1), where $N^1$ is contiguous with TTTCA and is of the formula $X^a$(T/A)(T/A)(T/A)(T/G)(C/G)(C/G)(C/G/A)(G/T)C$X^b$ wherein $X^a$ is present or absent, and when present is T or A; and
$X^b$ is present or absent, and when present is A or C; and
where $N^2$ is contiguous with TTTCA and is of the of the formula $X^c X^d X^e$, wherein $X^c$ is present or absent, and when present is T or G,
$X^d$ is present or absent, and when present is A or G, and
$X^e$ is present or absent, and when present is G.

The components of the spacer were selected by replacing a portion of a native Neisserial promoter (e.g., a native PorA promoter) with an analogous portion of another native Neisserial promoter (e.g., a native NadA promoter). In some embodiments, variants of the analogous sequence were used, including nucleotide substitutions, eliminations, or additions. FIG. 5 shows an alignment of the chimeric promoters of the present disclosure.

In some embodiments, the spacer portion is of the sequence ATATGCCTCCTTTCATA (SEQ ID NO: 4). In some embodiments, the spacer portion is of the sequence TATATGCCTCCTTTCATA (SEQ ID NO: 5). In some embodiments, the spacer portion is of the sequence ATAATGCCTCCTTTCATA (SEQ ID NO: 6). In some embodiments, the spacer portion is of the sequence ATATGCATCATTTCATA (SEQ ID NO: 7). In some embodiments, the spacer portion is of the sequence TTTTGCGGGCTTTCATA (SEQ ID NO: 8). In some embodiments, the spacer portion is of the sequence TTTTGCGGGCTTTCAGGG (SEQ ID NO: 9). In some embodiments, the spacer portion is of the sequence TTTTGCGGGCTTTCAG (SEQ ID NO: 10).

The chimeric promoters of the present disclosure can provide for an increase of expression of a gene product of interest of at least about 5%, about 10%, about 15%, about 20%, about 25%, about 50%, about 75%, or more relative to the expression level of the gene product from its native promoter. The engineered promoters of the present disclosure can provide for an increase in expression of a gene product of interest of at least 2-fold, about 3-fold, about 4-fold, about 5-fold, about 8-fold, about 10-fold, about 15-fold or more relative ot the expression level of the gene product from its native promoter.

When combined with a transcription terminator of the present disclosure, the chimeric promoter and transcription terminator can provide for a further increase in expression of a gene product of interest above that provided by a chimeric promoter without a transcription terminator, e.g, by at least about 5%, about 10%, about 15%, about 20%, about 25%, about 30% or more relative to the chimeric promoter without the transcription terminator.

Domain Deletion Promoters

The engineered promoters of the present disclosure that are derived from native promoter sequences wherein one or more functional domains of the native promoter have been deleted are referred to herein as domain deletion promoters. In general, the domain deletion promoters of the present disclosure are derived from a native Neisserial promoter. In some embodiments, a domain deletion promoter is derived from a native Neisserial nmb1523 promoter. The native nmb1523 promoter is approximately 580 nucleotides in length, and has a transcription factor binding domain located between nucleotides 105 and 369. The native nmb1523 promoter also has a 66 base pair extension domain located between nucleotides 511 and 577. FIG. 6 shows a schematic representation of several domain deletion promoters of the present disclosure.

Domain deletion promoters are of the general formula, from 5' to 3':

TFB-X-E-ATG wherein TFB refers to a transcription factor binding sequence of a native nmb1523 promoter, E refers to a 66 bp extension sequence of a native nmb1523 promoter, and X refers to a spacer sequence positioned between a TFB sequence and an E sequence of a native nmb1523 promoter, with the proviso that when TFB is present, E is absent, and when E is present, TFB is absent, e.g., so as to provide for domain deletion promoters of the following formulae, from 5' to 3': TFB-X-

ATG, X-E-ATG. In some embodiments, both TFB and E are absent, so as to provide for domain deletion promoters having the formula X-ATG.

In some embodiments, the domain deletion promoter is of the formula, from 5' to 3' TFB-X-ATG such that the promoter includes a native nmb1523 promoter sequence containing the transcription factor binding domain, but lacks the 66 base pair extension domain. In one example, the sequence of this domain deletion promoter comprises:

(SEQ ID NO: 50)
ATTTGTCCTTTCAGGAACAGCAGATTAATTACAGGCGCATTCTAACACAA

CCGCCGCGCCGGCCGATTACCGTTAACCTGTTCATAAACTGTACAGCACA

TATTTCAATGTAAATCTTTGTTATTTTATTGCGGTGTAACTTTTTTACAA

CATTCTTAAAACCATTCCGACCTGTCTGCCGACTTTCCCAATCCGCCTTA

ATAAATCATACAAGATACTGAAATTATATTAATCTCTATAATATTTATCC

CTATCGAATTTTTAACAGCAAAACCGTTTTACAGGATTTATCAATCCGCC

CGCCAGAAAACTTTTCATTCAAACCTTTTTCCCATCTGTACGACATTGCA

ATCCCTTATTCCATAGTGCATAATTACGCAAATTCAGCGATGAATTTCCA

ACCCGG.

In other embodiments, the domain deletion promoter is of the formula, from 5' to 3' X-E-ATG such that the promoter includes a nucleotide sequence of a native nmb1523 promoter sequence containing the 66 base pair extension domain, but lacks the transcription factor binding domain. In one example, the sequence of the domain deletion promoter comprises:

(SEQ ID NO: 51)
CATGGATCCACAGCAAAACCGTTTTACAGGATTTATCAATCCGCCCGCCA

GAAAACTTTTCATTCAAACCTTTTTCCCATCTGTACGACATTGCAATCCC

TTATTCCATAGTGCATAATTACGCAAATTCAGCGATGAATTTCCAACCCG

GTTTGTAGTATGGTCGATAAAGACCTATTTGTTTCAATAATTTAAATTGG

TTCTAAAGGTTACTCATATGCGA.

In other embodiments, the domain deletion promoter is of the formula, from 5' to 3' X-ATG such that the promoter includes the spacer element, but lacks the transcription factor binding domain and the 66 base pair extension domain of the native nmb1523 promoter. In one example, the sequence of the domain deletion promoter comprises:

(SEQ ID NO: 52)
CATGGATCCACAGCAAAACCGTTTTACAGGATTTATCAATCCGCCCGCCA

GAAAACTTTTCATTCAAACCTTTTTCCCATCTGTACGACATTGCAATCCC

TTATTCCATAGTGCATAATTACGCAAATTCAGCGATGAATTTCCAACCCG

GCATATGCGA.

The domain deletion promoters of the present disclosure can provide for an increase in expression of a gene product of interest by at least about 5%, about 10%, about 15%, about 20%, about 25%, about 50%, about 75%, or more relative to an expression level of the gene product from its native promoter. The domain deletion promoters of the present disclosure can provide for an increase in expression of a gene product of at least about 2-fold, about 3-fold, about 4-fold, about 5-fold, about 8-fold, about 10-fold or more relative to an expression level of the gene product from its native promoter.

When combined with a transcription terminator of the present disclosure, the domain deletion promoter and transcription terminator can provide for a further increase in expression of a gene product of interest above that provided by a domain deletion promoter without a transcription terminator, e.g., by at least about 5%, about 10%, about 15%, about 20%, about 25%, about 30% or more relative to the domain deletion promoter without the transcription terminator.

Transcription Terminators

The present disclosure generally provides polynucleotide sequences that function as transcription terminators, which can further facilitate efficient expression of gene products in a host cell, e.g., a *Neisseria* cell. Without being held to theory, the transcription terminator sequences generally function by dissociating RNA polymerase from the DNA template sequence, thus terminating the transcription process.

The present disclosure generally provides transcription terminator sequences that can be operably linked to the 3' end of a polynucleotide sequence encoding a surface antigen to facilitate efficient expression. In some embodiments, polynucleotide constructs comprising a transcription terminator sequence are provided in which the transcription terminator sequence is heterologous to the promoter sequence, the coding sequence, or both. In other embodiments, a transcription terminator sequence can be a native sequence that is found operably attached to the 3' end of a coding sequence in nature. Transcription terminator sequences can be naturally-occurring transcription terminators of native surface antigen coding sequences, e.g., fHbp coding sequences, especially native fHbp coding sequences that naturally exhibit increased expression relative to other fHbp coding sequences.

The polynucleotide sequences of the present disclosure that function as transcription terminators generally have at least about 85% sequence identity to the following sequence:

(SEQ ID NO: 53)
TAACCATTGTGAAAATGCCGTCCGAACACGATAATTTACCGTTCGGACGG

CATTTGTA.

In some embodiments, the transcription terminator sequence has up to about 90%, up to about 95%, or up to about 98% sequence identity to the sequence disclosed above.

As shown in FIG. 15, the presence of a transcription terminator sequence operably linked to the 3' end of a polynucleotide sequence encoding a surface antigen resulted in increased expression of the surface antigen in a recombinant host. Use of transcription terminator sequences to increase expression is further described in Example 9.

Polynucleotide Constructs

The polynucleotide sequences of the present disclosure can be provided in a variety of forms, such as a construct, e.g., an expression construct, for use in the methods described herein. Examples include circular, linear, double-stranded, extrachromosomal DNA molecules (plasmids), cosmids (plasmids containing COS sequences from lambda phage), viral genomes comprising non-native nucleic acid sequences, and the like. A "vector" is any molecule or agent capable of transferring gene sequences to target cells. Typically, "vector construct," "expression vector," and "gene transfer vector," mean any polynucleotide construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning and expression vehicles, as well as integrating vectors.

The constructs of the present disclosure may include expression constructs comprising an engineered promoter operably linked to, for example, one or more polynucleotides encoding one or more gene products of interest (e.g., a polypeptide or mRNA). In some embodiments, an expression construct may also include a transcription terminator sequence operably linked to the 3' end of a coding sequence of interest. An "expression cassette" comprises any nucleic acid construct capable of directing the expression of one or more coding sequences of interest, which are operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

The nucleic acid constructs of the present disclosure may also include specific nucleotide sequences (e.g., restriction enzyme recognition sequences or homologous recombination sequences) that can facilitate the transfer of nucleic acid sequences between constructs or into the genome of a host. For example, constructs may be provided in which an engineered promoter (or expression construct comprising an engineered promoter) is flanked by homologous recombination sequences to facilitate genomic insertion of the target sequence into the genome of a host cell (e.g., a Neisseria cell) by homologous recombination at a desired location in the genome of the cell.

The present disclosure generally provides expression constructs that may comprise an engineered promoter sequence of the present disclosure operably linked to one or more polynucleotide sequences that encode a gene product of interest (e.g., a protein of interest, e.g., an antigen of interest, such as a surface antigen (e.g., fHbp)). In some embodiments, the expression constructs of the present disclosure also include a transcription terminator sequence that is operably linked to the 3' end of a polynucleotide sequence that encodes a gene product (e.g., a protein) of interest. In some embodiments, expression constructs of the present disclosure may contain a plurality of polynucleotide sequences that encode one or more gene products (e.g., proteins) of interest. In such embodiments, the polynucleotide sequences that encode the gene products (e.g., proteins) of interest may encode different gene products (e.g., proteins) of interest, or may encode the same gene products (e.g., proteins) of interest.

In some embodiments, expression constructs of the present disclosure may include an engineered promoter sequence that is operably linked to a polynucleotide sequence that encodes a gene product (e.g., a protein) of interest, such that a single engineered promoter sequence drives expression of a single gene product (e.g., protein) of interest.

In some embodiments, expression constructs of the present disclosure may include an engineered promoter sequence that is operably linked to a plurality of polynucleotide sequences that encode one or more gene products (e.g., proteins) of interest, such as two or more, or such as three or more, polynucleotide sequences that encode gene products (e.g., proteins) of interest, such that a single engineered promoter sequence drives expression of a plurality of polynucleotide sequences that encode one or more gene products (e.g., proteins) of interest. In such embodiments, the polynucleotide sequences that encode the gene products (e.g., proteins) of interest may encode the same gene product, or may encode different gene products (e.g., may encode different surface antigens). As described above, in some embodiments, the expression constructs of the present disclosure may include a transcription terminator sequence that is operably linked to the 3' end of one of the gene product of interest-encoding polynucleotide sequences. Expression constructs of the present disclosure may also contain restriction enzyme recognition sequences and/or homologous recombination sequences that facilitate transfer of the polynucleotide sequences between constructs or into a suitable host.

Recombinant Hosts

In general, the present disclosure involves the use of recombinant hosts for the replication and expression of nucleic acid constructs. Any of a variety of suitable host cells (e.g., various suitable Neisserial strains) may be used with the constructs and methods of the present disclosure, including but not limited to naturally-occurring strains and genetically modified strains.

In some embodiments, replication hosts are used to replicate nucleic acid constructs of the present disclosure. Constructs are introduced into the replication host using any suitable technique, and the host cells are then cultured under appropriate conditions that facilitate replication of the construct. After the host cells have been cultured for a sufficient time, the cells are lysed and the replicated nucleic acid constructs are isolated and purified for further use in the methods of the present disclosure.

Suitable replication hosts are well known in the art, and include, e.g. DH5 alpha competent cells, DH10B cells, XL-1 Blue cells, JM109 cells, and the like.

Any of a variety of suitable host cells may be used as expression hosts to express an antigen of interest using various combinations of the polynucleotide sequences of the present disclosure. In some embodiments, pathogenic or commensal *Haemopilus* spp. or *Neisseria* spp. or strains derived from pathogenic *Neisseria* spp., particularly strains pathogenic for humans or derived from strains pathogenic or commensal for humans, are used as expression hosts. Exemplary *Nessserial* spp. include *N. meningitidis*, *N. flavescens*, *N. gonorrhoeae*, *N. lactamica*, *N. polysaccharea*, *N. cinerea*, *N. mucosa*, *N. subflava*, *N. sicca*, *N. elongata*, and the like. "Derived from" in the context of bacterial strains is meant to indicate that a strain was obtained through passage in vivo, or in vitro culture, of a parental strain and/or is a recombinant cell obtained by modification of a parental strain.

*N. meningitidis* strains can be divided into serologic capsular groups (also called serogroups), PorB serotypes and PorA serosubtypes on the basis of reactions with polyclonal (Frasch, C. E. and Chapman, 1973, J. Infect. Dis. 127: 149-154) or monoclonal antibodies that interact with different surface antigens. Serogrouping is based on immunologically detectable variations in the capsular polysaccharide. About 12 serogroups (A, B, C, X, Y, Z, 29-E, and W-135) are known. PorA serosubtypes can also be classified by differences in DNA sequences of two variable regions (VR1 and VR2), and are referred to VR types (see, e.g., Russell et al. Emerging Infect Dis 2004 10:674-78; Sacchi C T, et al. Clin Diagn Lab Immunol 1998; 5:845-55; Sacchi et al, J. Infect Dis 2000; 182:1169-76).

The Neisserial strain to be used as an expression host can be selected according to a number of different characteristics that may be desired. For example, the strain may be selected according to a desired serogroup, serotype, serosubtype, and the like; decreased capsular polysaccharide production, and the like.

Alternatively or in addition, a suitable expression host strain can be a capsule deficient strain. Capsule deficient strains can be used to produce vesicle-based vaccines that provide for a reduced risk of eliciting a significant autoantibody response in a subject to whom the vaccine is administered (e.g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell ELISA using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. J. Infect. Dis. (2003) 187(10):1616-28)), as well as methods of identifying and/or generating capsule-deficient strains (see, e.g., Fisseha et al. (2005) Infect. Immun. 73(7):4070-4080; Stephens et al. (1991) Infect Immun 59(11):4097-102; Frosch et al. (1990) Mol. Microbiol. 1990 4(7):1215-1218)) are known in the art.

Modification of a Neisserial host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes.

Strains that are deficient in sialic acid biosynthesis may also be used as expression hosts. Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetylglucosamine-6-phosphate 2-epimerase gene (known as synX AAF40537.1 or siaA AAA20475), with strains having this gene inactivated being of special interest. For example, in one embodiment, a capsule deficient strain is generated by disrupting production of a functional synX gene product (see, e.g., Swartley et al. (1994) J. Bacteriol. 176(5):1530-4).

Capsular deficient strains can also be generated from naturally-occurring strains using non-recombinant techniques, e.g., by use of bactericidal anti-capsular antibodies to select for strains that are reduced in capsular polysaccharide.

Where the use of two or more expression hosts is involved (e.g., to produce antigenic compositions of vesicles from different strains), the hosts can be selected so as to differ in on or more strain characteristics.

Methods suitable for the growth and maintenance of recombinant Neisserial strains are well known in the art. In general, bacterial cells are grown at approximately 35-37° C. in appropriate growth media (e.g. Mueller-Hinton broth (BD Biosciences, Franklin Lakes, N.J., US) supplemented or not with 0.25% glucose (w/v) and 0.02 mM cytidine 5'-monophospho-N-acetylneuraminic acid (Sigma-Aldrich, St Louis, Mo., US), Regular or modified Frantz Media, Minimal media, Catling Media, etc).

Gene Products Suitable for Expression from an Engineered Promoter

The polynucleotide sequences and methods of the present disclosure generally facilitate consistent, high-level expression of any gene product of interest (e.g., a protein of interest, e.g., a surface antigen of interest) in a recombinant host. The promoter sequences and/or transcription terminator sequences of the present disclosure can be operably linked to a polynucleotide sequence encoding any gene product of interest in order to facilitate its expression in a recombinant host. In some embodiments, the polynucleotide coding sequences of the present disclosure comprise translationally optimized sequences, wherein the codons in the coding sequence have been optimized to facilitate efficient expression in the host organism. This technique is described in more detail below.

The following are examples of gene products that are contemplated by the compositions and methods of the present disclosure. The following examples of gene products are in no way limiting, and those of skill in the art will readily appreciate that the sequences and methods of the present disclosure may be used to express any gene product of interest.

Gene products of interest that are suitable for expression include, but are not necessarily limited to, naturally-occurring polypeptides (e.g., as encoded by an endogenous genomic sequence), and recombinant polypeptides, where a recombinant polypeptide may be a polypeptide having an amino acid sequence endogenous or exogenous to the host cell. Where the polypeptide is an exogenous polypeptide, the polypeptide may have an amino acid sequence of a naturally-occurring polypeptide that is not endogenous to the host cell and/or have an amino acid sequence that is non-naturally occurring (e.g., a man-made polypeptide having an amino acid sequence that does not occur in nature). Polypeptides can be of any of a variety of classes, including but not limited to e.g., secreted proteins, outer membrane proteins, (e.g., surface antigens), and intracellular proteins. Gene products of interest also include protein-encoding and non-protein-encoding RNAs, where the RNAs may be either endogenous or exogenous to the host cell.

The polynucleotides and methods of the present disclosure find use in facilitating expression of gene products such as those provided herein, e.g., to facilitate vaccine production in a recombinant host. As set out in the examples in more detail below, various gene products, including but not limited to Neisserial outer membrane proteins and their variants and subvariants, are well known in the art and find use in connection with the sequences and methods of the present disclosure.

fHbp

Factor H binding protein (fHbp), also known in the literature as GNA1870, ORF2086, rLP-2086, and "741", is a *Neisseria meningitidis* surface antigen. FIG. 2 shows a schematic diagram of the genes located upstream and downstream of the fHbp gene in two different Neisserial strains. "fHbp polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring fHbp polypeptide, and which are capable of eliciting antibodies that specifically bind a naturally-occurring fHbp polypeptide present on a *Neisseria meningitidis* bacterium. "fHbp polypeptide" also encompasses fusion proteins, e.g., a fHbp polypeptide having a heterologous polypeptide at the N- and/or C-terminus.

Nucleic acids encoding fHbp polypeptides for use in the present disclosure are known in the art. Suitable fHbp polypeptides are described in, for example, WO 2004/048404; Masignani et al. 2003 J Exp Med 197:789-799; Fletcher et al. Infect Immun 2004 2088-2100; Welsch et al. J Immunol 2004 172:5606-5615; and WO 99/57280. Nucleic acid (and amino acid sequences) for fHbp variants and subvariants are also provided in GenBank as accession nos.: NC_003112, GeneID: 904318 (NCBI Ref. NP_274866) (from *N. meningitidis* strain MC58); AY548371 (AAT01290.1) (from *N. meningitidis* strain CU385); AY548370 (AAT01289.1) (from *N. meningitidis* strain H44/76); AY548377 (AAS56920.1) (from *N. meningitidis* strain M4105); AY548376 (AAS56919.1) (from N. strain M1390); AY548375 (AAS56918.1) (from *N. meningitidis* strain N98/254); AY548374 (AAS56917.1) (from *N. meningitidis* strain M6190); AY548373 (AAS56916.1) (from *N. meningitidis* strain 4243); and AY548372 (AAS56915.1) (from *N. meningitidis* strain BZ83).

fHbp polypeptides useful in the present disclosure include non-naturally occurring (artificial or mutant) fHbp polypeptides that differ in amino acid sequence from a naturally-occurring fHbp polypeptide, but which are present in the membrane of a Nesserial host so that vesicles prepared from the host contain fHbp in a form that provides for presentation of epitopes of interest, preferably a bactericidal epitope, and provides for an anti-fHbp antibody response. In one embodiment, the fHbp polypeptide is a variant 1 (v.1) or variant 2 (v.2) or variant 3 (v.3) fHbp polypeptide, with subvariants of v.1 v.2 and v.3 being of interest, including subvariants of v.1 (see, e.g., Welsch et al. J Immunol 2004 172:5606-5615). Subvariants are defined by peptide alleles or identification numbers (ID) as specified on the website: pubmlst.org/*neisseria*/fHbp/. In one embodiment, the fHbp polypeptide comprises an amino acid sequence of a fHbp polypeptide that is most prevalent among the strains endemic to the population of a subject to be vaccinated.

fHbp polypeptides useful in the present disclosure also include fusion proteins, where the fusion protein comprises a fHbp polypeptide having a fusion partner at its N-terminus or C-terminus. Fusion partners of interest include, for example, glutathione S transferase (GST), maltose binding protein (MBP), His-tag, and the like, as well as leader peptides from other proteins, particularly lipoproteins (e.g., the amino acid sequence prior to the N-terminal cysteine may be replaced with another leader peptide of interest).

Other fHbp polypeptide-encoding nucleic acids can be identified using techniques well known in the art, where fHbp polypeptides can be identified based on amino acid sequence similarity to a known fHbp polypeptide. Such fHbp polypeptides generally share at least about 60%, 65%, 70%, 75%, 80%, 85%, 90%, 95% or greater sequence identity at the nucleotide or amino acid level. Sequence identity can be determined using methods for alignment and comparison of nucleic acid or amino acid sequences, which methods are well known in the art. Comparison of longer sequences may require more sophisticated methods to achieve optimal alignment of two sequences. Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e. resulting in the highest percentage of sequence similarity over the comparison window) generated by the various methods is selected.

PorA

PorA is another *Neisseria meningitidis* surface antigen. "PorA polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring PorA polypeptide, and which are capable of eliciting antibodies that specifically bind a naturally-occurring PorA polypeptide present on a *Neisseria meningitidis* bacterium. "PorA polypeptide" also encompasses fusion proteins, e.g., a PorA polypeptide having a heterologous polypeptide at the N- and/or C-terminus.

Nucleic acids encoding PorA polypeptides for use in the present disclosure are known in the art. Suitable PorA polypeptides include those that confer a serosubtype of P1.7,16; P1.19,15; P1.7,1; P1.5,2; P1.22a,14; P1.14; P1.5,10; P1.7,4; P1.12,13; as well as variants of such PorA polypeptides which may or may not retain reactivity with conventional serologic reagents used in serosubtyping.

Also of interest are PorA polypeptides characterized according to PorA variable region (VR) typing (see, e.g., Russell et al. Emerging Infect Dis 2004 10:674-678; Sacchi C T, et al, Clin Diagn Lab Immunol 1998; 5:845-55; Sacchi et al, J. Infect Dis 2000; 182:1169-1176). A substantial number of distinct VR types have been identified, which can be classified into VR1 and VR2 family "prototypes". A web-accessible database describing this nomenclature and its relationship to previous typing schemes is found at *neisseria*.org/nm/typing/porA. Alignments of exemplary PorA VR1 and VR2 types is provided in Russell et al. Emerging Infect Dis 2004 10:674-678.

Exemplary PorA polypeptides as characterized by PorA serosubtypes include P1.5,2; P1.5a,2a; P1.5a,2c; P1.5a,2c; P1.5a,2c; P1.5b,10; P1.5b,10; P1.5b, C; P1.7,16; P1.7d,1; P1.7d,1; P1.7d,1; P1.7d,1; P1.7b,3; P1.7b,4; P1.7b,4; P1.12,16; P1.12a,13a; P1.22,9; P1.23,14; P1.23,14; P1.19,15; P1.B,1; P1.C,1; P1.E,A; P1.E,A; P1.E,A; P1.5,2; P1.5,2; P1.5a,10a; P1.5b,10; P1.5b,10; P1.5b,10b; P1.7,16; P1.7,16; P1.7b,1; P1.7b,13e; P1.7b,4; P1.7b,4; P1.7d,1; P1.7d,1; P1.7b,13a; P1.23,3; P1.23,3; P1.23,3; P1.19,15; P1.19,1; P1.19,15; P1.19,15; P1.19,15; P1.19,15; P1.19,15; P1.19,15; P1.19,15; P1.E,A; P1.E,A; P1.E,16a; P1.E,4a; P1.E,4a; P1.Ea,3; P1.Eb,9; P1.Eb,9; P1.Eb,9; P1.Eb,9; P1.Eb,9; P1.F,16; P1.7a,1; P1.7b,3; P1.7d,1; P1.Ea,3; P1.5b,10; P1.5b,10; P1.5b,10; P1.5b,10; P1.5b,10; P1.5b,10; P1.5b,10b; P1.5b,10; P1.22,14a; P1.F,16; P1.D,2d; P1.D,2; P1.D,2d; P1.19c,2c; P1.D,10f; P1.A,10e; P1.A,10g; P1.A,10; P1.19,15; P1.19,15; P1.19,15; P1.19,15; P1.7b,16; P1.7,16b; P1.7,16; P1.19,15; P1.Eb,9; P1.5,2e; P1.E,A; P1.7b,13d; P1.Ea,3; P1.7,16b; P1.Ec,1; P1.7b,4; P1.7b,4; P1.7,9; P1.19,15; P1.19,15; P1.19,15; P1.19,15a; P1.19a,15b; P1.19,15; P1.5b,16; P1.19b,13a; P1.5,16; P1.5,2; P1.5,2b; P1.7b,16; P1.7,16b; P1.7b,3; P1.Ea,3; P1.5a,2c; P1.F,16; P1.5a,9; P1.7c,10c; P1.7b,13a; P1.7,13a; P1.7a,10; P1.20,9; P1.22,B; P1.5b,del; P1.5b,10; P1.7,13a; P1.12a,13f; P1.12a,13; P1.12a,13a; P1.12a,13a; P1.12a,13; P1.12a,13; P1.E,13b; P1.7b,13a; P1.7b,13; P1.5,2; P1.5,2; P1.Ea,3; P1.22,9; P1.5,2; P1.5,2; P1.19,15; P1.5,2; P1.12b,13a; P1.5c,10a; P1.7e,16e; P1.B, 16d; P1.F,16e; P1.F,16e; P1.7b,13e; P1.B,16d; P1.7e,16e; P1.7b,13g; P1.B,16f; P1.7,16c; P1.22,14b; P1.22,14c; P1.7, 14; P1.7,14; and P1.23,14.

Amino acid sequences of exemplary PorA polypeptides are found at GenBank accession nos. X57182, X57180, U92941, U92944, U92927, U92931, U92917, U92922, X52995, X57184, U92938, U92920, U92921, U92929, U92925, U92916, X57178, AF051542, X57181, U92919, U92926, X57177, X57179, U92947, U92928, U92915, X57183, U92943, U92942, U92939, U92918, U92946, U92496, U97260, U97259, AF042541, U92923, AF051539, AF051538, U92934, AF029088, U92933, U97263, U97261, U97262, U92945, AF042540, U92935, U92936, U92924, AF029086, AF020983, U94958, U97258, U92940, AF029084, U92930, U94959, U92948, AF016863, AF029089, U92937, AF029087, U92932, AF029090, AF029085, AF051540, AF051536, AF052743, AF054269, U92495, U92497, U92498, U92499, U92500, U92501, U92502, U92503, AF051541, X12899, Z48493, Z48489, Z48485, Z48494, Z48487, Z48488, Z48495, Z48490, Z48486, Z48491, Z48492, X66478, X66479, X66477, X66480, X81110, X79056, X78467, X81111, X78802, Z14281/82, Z14273/74, Z14275/76, Z14261/62, Z14265/66, Z14277/78, Z14283/84, Z14271/72, Z14269/70, Z14263/64, Z14259/60, Z14257/58, Z14293/94, Z14291/92, Z14279/80, Z14289/90, Z14287/88, Z14267/68, Z14285/86, L02929, X77423, X77424, X77433, X77426, X77428, X77430, X77427, X77429, X77425, X77432, X77431, X77422, Z48024/25, Z48032/33, Z48020/21, Z48022/23, Z48028/29, Z48016/17, Z48012/13, Z48014/15, Z48018/19, Z48026/27, U31060, U31061, U31062, U31063, U31064, U31065, U31066, U31067, U93898, U93899, U93900, U93901, U93902, U93903, U93904, U93905, U93906, U93907, and U93908.

NspA

NspA is another *Neisseria meningitidis* surface antigen. "NspA polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring NspA polypeptide, and which are capable of eliciting antibodies that specifically bind a naturally-occurring NspA polypeptide present on a *Neisseria meningitidis* bacterium. "NspA polypeptide" also encompasses fusion proteins, e.g., a NspA polypeptide having a heterologous polypeptide at the N- and/or C-terminus.

Nucleic acids encoding NspA polypeptides for use in the present disclosure are known in the art. Suitable NspA polypeptides are described in, for example, Martin et al., J Exp Med, Apr. 7, 1997, 185(7).

Nucleic acid (and amino acid sequences) for NspA variants and subvariants are also provided in GenBank as accession nos.: U52069, GQ293900.1, AF175678.1, AF175683.1, AF175682.1, AF175681.1, AF175680.1, AF175679.1, AF175677.1, AF175676.1.

TbpB

TbpB is a *Neisseria* surface antigen. "TbpB polypeptide" as used herein encompasses naturally-occurring and synthetic (non-naturally occurring) polypeptides that share at least about 60%, 65%, 70%, 75%, 80%, 85%, 90%, 95% or greater sequence identity at the nucleotide or amino acid level with a naturally-occurring TbpB polypeptide, and which are capable of eliciting antibodies that specifically bind a naturally-occurring TbpB polypeptide present on a *Neisseria meningitidis* bacterium. "TbpB polypeptide" also encompasses fusion proteins, e.g., a TbpB polypeptide having a heterologous polypeptide at the N- and/or C-terminus.

Nucleic acids encoding TbpB polypeptides for use in the present disclosure are known in the art. Suitable TbpB polypeptides are described in, for example, Rokbi, B. et al., "Heterogeneity of tbpB, the transferrinbinding protein B gene, among serogroup B *Neisseria meningitidis* strains of the ET-5 complex," Clinical and Diagnostic Laboratory Immunology 4(5): 522-529 (1997).

Nucleic acid (and amino acid sequences) for TbpB variants and subvariants are also provided in GenBank as accession nos.: DQ355978.1, AJ704760.1, AJ704759.1, AJ704758.1, AJ704757.1, AJ704756.1, AJ704755.1, AJ704754.1, AJ704753.1, AJ704752.1, AJ704751.1.

TbpA

TbpA is a *Neisseria* surface antigen. "TbpA polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring TbpA polypeptide, and which are capable of eliciting antibodies that specifically bind a naturally-occurring TbpA polypeptide present on a *Neisseria* bacterium. "TbpA polypeptide" also encompasses fusion proteins, e.g., a TbpA polypeptide having a heterologous polypeptide at the N- and/or C-terminus.

Nucleic acids encoding TbpA polypeptides for use in the present disclosure are known in the art. Suitable TbpA polypeptides are described in, for example, J. Med. Microbiol. 1998 September; 47(9): 757-60.

Nucleic acid (and amino acid sequences) for TbpA variants and subvariants are also provided in GenBank as: Accession: EU339282.1 GI: 166863281, Accession: M96731.1 GI: 150360, Accession: AF240638.1 GI: 9719359, Accession: AF241227.1 GI: 9719361, Accession: AF124338.1 GI: 8439550, Accession: X94533.1 GI: 2764816, Accession: X99615.1 GI: 2764959, Accession: X99614.1 GI: 2764957, Accession: X99613.1 GI: 2764956, Accession: X99612.1 GI: 2764955, Accession: X99611.1 GI: 2764954, Accession: X99610.1 GI: 2764952.

LbpA

LbpA is a *Neisseria* surface antigen. "LbpA polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring LbpA polypeptide, and which are capable of eliciting antibodies that specifically bind a naturally-occurring LbpA polypeptide present on a *Neisseria* bacterium. "LbpA polypeptide" also encompasses fusion proteins, e.g., a LbpA polypeptide having a heterologous polypeptide at the N- and/or C-terminus.

Nucleic acids encoding LbpA polypeptides for use in the present disclosure are known in the art. Suitable LbpA polypeptides are described in, for example, Vaccine (2006) Vol. 24 Issue 17, pp. 3545-57.

Nucleic acid (and amino acid sequences) for LbpA variants and subvariants are also provided in GenBank as: Accession: DQ058017.1 GI: 68359439, Accession: U16260.1 GI: 915277, Accession: AF049349.1 GI: 3582727, Accession: DQ058018.1 GI: 68359441, Accession: X79838.1 GI: 509053.

LbpB

LbpB is a *Neisseria* surface antigen. "LbpB polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring LbpB polypeptide, and which are capable of eliciting antibodies that specifically bind a naturally-occurring LbpB polypeptide present on a *Neisseria* bacterium. "LbpB polypeptide" also encompasses fusion proteins, e.g., a LbpB polypeptide having a heterologous polypeptide at the N- and/or C-terminus.

Nucleic acids encoding LbpB polypeptides for use in the present disclosure are known in the art. Suitable LbpB polypeptides are described in, for example, Vaccine (2006) Vol. 24 Issue 17, pp. 3545-57.

Nucleic acid (and amino acid sequences) for LbpB variants and subvariants are also provided in GenBank as: Accession: AF123382.1 GI: 4884690, Accession: AF072890.1 GI: 4106392, Accession: AF031432.1 GI: 3213214, Accession: AF022781.1 GI: 2843172, Accession: AF123380.1 GI: 4884686, Accession: AF123383.1 GI: 4884692, Accession: AF123381.1 GI: 4884688.

GNA2132

GNA2132 is a *Neisseria* surface antigen. "GNA2132 polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring GNA2132 polypeptide, and which are capable of eliciting antibodies that specifically bind a naturally-occurring GNA2132 polypeptide present on a *Neisseria* bacterium. "GNA2132 polypeptide" also encompasses fusion proteins, e.g., a GNA2132 polypeptide having a heterologous polypeptide at the N- and/or C-terminus.

Nucleic acids encoding GNA2132 polypeptides for use in the present disclosure are known in the art. Suitable GNA2132 polypeptides are described in, for example, Proc Natl Acad Sci U.S.A. 2010 Feb. 23; 107(8): 3770-5.

Nucleic acid (and amino acid sequences) for GNA2132 variants and subvariants are also provided in GenBank as: Accession: FJ750981.1 GI: 224830211, Accession: AY315195.1 GI: 32455020, Accession: AY315194.1 GI: 32455018, Accession: AY315193.1 GI: 32455016, Accession: AY315192.1 GI: 32455014, Accession: GQ302857.1 GI: 254547346, Accession: AY315196.1 GI: 32455022, Accession: AF226448.1 GI: 7228725, Accession: AF226447.1 GI: 7228723, Accession: AF226446.1 GI: 7228721, Accession: AF226445.1 GI: 7228719, Accession: FN908855.1 GI: 308814886, Accession: FN908854.1 GI: 308814884, Accession: FJ615459.1 GI: 222107907, Accession: FJ615446.1 GI: 222107881.

NadA

NadA is a *Neisseria* surface antigen. "NadA polypeptide" as used herein encompasses naturally-occurring and synthetic (non-naturally occurring) polypeptides which share at least about 60%, 65%, 70%, 75%, 80%, 85%, 90%, 95% or greater sequence identity at the nucleotide or amino acid level with a naturally-occurring NadA polypeptide, and which are capable of eliciting antibodies that specifically bind a naturally-occurring NadA polypeptide present on a *Neisseria* bacterium. "NadA polypeptide" also encompasses fusion proteins, e.g., a NadA polypeptide having a heterologous polypeptide at the N- and/or C-terminus.

Nucleic acids encoding NadA polypeptides for use in the present disclosure are known in the art. Suitable NadA polypeptides are described in, for example, Infection and Immunity, July 2004, Vol. 72, No. 7, pp. 4217-23.

Nucleic acid (and amino acid sequences) for NadA variants and subvariants are also provided in GenBank as: Accession: FJ750979.1 GI: 224830207, Accession: DQ239933.1 GI: 83616362, Accession: DQ239932.1 GI: 83616360, Accession: DQ239931.1 GI: 83616359, Accession: DQ239930.1 GI: 83616357, Accession: DQ239929.1 GI: 83616355, Accession: DQ239928.1 GI: 83616354, Accession: DQ239927.1 GI: 83616353, Accession: DQ239926.1 GI: 83616351, Accession: FJ619647.1 GI: 222159590.

Further Examples of Gene Products of Interest

Other examples of gene products that find use with the sequences and methods of the present disclosure include the following:

Opacity outer membrane protein (see, e.g., Hobbs et al., Microbiology 144:157-66 (1998)), Genbank Accession Numbers: U03412.1, U37255.1, U37256.1, U37257.1, AF016292.1, AF016285.1, AF001204.1, AF001203.1;

FetA (see, e.g., Biegel et al, *J. Bacteriology* 181(9):2895-901 (1999)), Genbank Accession Numbers: JN182195.1 GI: 343174597, EF157665.1 GI: 120971583, EF153764.1 GI: 120971579, EF153762.1 GI: 120971576;

MafB, MspA, App, Opa, Opc, NhhA, MafA-1, MafA2, NalP, Mip, NMB1483, HmbR (see, e.g., Echenique-Rivera et al., *PLoS Pathog* 7(5): 1-18 (2011));

The foregoing gene products are in no way intended to limit the scope of the present disclosure, and merely serve as examples of antigens that may be expressed using the polynucleotide sequences and methods disclosed herein.

Codon Optimization

Polynucleotide sequences encoding gene products of interest encompass naturally-occurring sequences as well as codon-optimized sequences. Naturally-occurring sequences may be codon-optimized in order to further facilitate increased expression levels based on known codon preferences of the host organism selected for expression. For example, a known polynucleotide sequence encoding a surface antigen (e.g., fHbp) may be altered to replace those codons that are not preferred by the host organism with redundant codons that encode the same amino acid residue, but which are preferred by the host organism and therefore facilitate more efficient expression of the coding sequence in the host organism.

A variety of computer algorithms that facilitate codon optimization are publicly available via the internet. See, e.g., Puigb P., Guzman E., Romeu A., and Garcia-Vallv S., OPTI-MIZER: A web server for optimizing the codon usage of DNA sequences. Nucleic Acids Research, 35:W126-W131 (2007). Such algorithms generally allow a user to input a known polynucleotide sequence encoding a gene product. Once the sequence has been provided, the user may specify any desired codon-usage preferences (e.g., the most frequently-used codons for each amino acid residue in the chosen expression host) and the computer algorithm will then provide the user with a codon-optimized sequence. For example, FIGS. 16 and 17 show tables that provide the mean codon usage per thousand for each amino acid residue in the *Neisseria meningitidis* FAM18 and Z2491 strains, respectively. Once the mean codon usage has been determined for a given expression host, the polynucleotide sequence encoding a gene product of interest can be engineered by replacing redundant codons with codons that encode the same amino acid residue, but which are more frequently utilized by the expression host, i.e., codons that encode the same amino acid residue but have a higher mean usage value. FIG. 18 is a sequence comparison showing the nucleotide sequence of a native fHbp ID 9 compared with a codon-optimized sequence for the same gene product. In the codon-optimized sequence, less-preferred codons have been replaced with more frequently-utilized redundant codons. Codon optimization is further described in Example 10.

Methods of Making

Polynucleotide sequences of the present disclosure may be generated by any means known in the art, including but not limited to mutagenesis techniques, including chemical mutagenesis, polymerase chain reaction (PCR), site-directed mutagenesis of one or more nucleotides, and the like. Polynucleotide sequences may also be chemically synthesized using reagents and techniques known in the art. Expression constructs according to the present disclosure may be generated by using techniques known in the art, including but not limited to PCR, cloning, and the like. Practicing the present invention may involve the use of conventional molecular biology, microbiology, recombinant DNA, and immunology techniques that are well known in the art. Such techniques are fully explained in the literature, e.g. Sambrook *Molecular Cloning; A Laboratory Manual, Second Edition* (1989); *DNA Cloning, Volumes I and II* (D. N. Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Immobilized Cells and Enzymes* (IRL Press, 1986); B. Perbal, *A Practical Guide to Molecular Cloning* (1984); the *Methods in Enzymology* series (Academic Press, Inc.); Mayer and Walker, eds. (1987), *Immunochemical Methods in Cell and Molecular Biology* (Academic Press, London).

In general, the polynucleotide sequences of the present disclosure may be cloned into a suitable vector or expression construct for use in the methods of the present disclosure. In some embodiments, an engineered promoter sequence is operably linked to a polynucleotide sequence encoding a surface antigen, which is operably linked to a transcription terminator sequence. The resulting sequence (comprising a promoter sequence, a surface antigen-encoding sequence, and a transcription terminator sequence) may then be isolated, e.g., by PCR or with restriction enzymes, and cloned into a suitable vector or construct. In some embodiments, constructs may contain polynucleotide sequences that can be used to introduce a target sequence into the genome of a host, e.g., by homologous recombination.

Methods of Use

In general, the present disclosure provides methods for expressing one or more gene products of interest, e.g., one or more proteins of interest, e.g., one or more surface antigens of interest, in recombinant host organsims at high levels. The methods involve combining the polynucleotide sequences of the present disclosure in ways that facilitate high-level expression of a gene product (e.g., a protein) of interest in a selected recombinant host organism, e.g., a *Neisseria meningitidis* bacterium. The methods of the present disclosure find use in, e.g., production of vaccines, where consistent, high-level expression of surface antigens is desirable.

As described above, some of the polynucleotide sequences of the present disclosure function as promoters in host organisms. Unlike some naturally-occurring promoter sequences, the present promoters do not cause variable expression, but instead provide consistent, high-level expression of one or more gene product-encoding polynucleotide sequences to which they are operable linked. Other polynucleotide sequences of the present disclosure function as transcription terminators that facilitate efficient transcription, and therefore enhanced expression of gene product-encoding sequences to which they are operably linked. Various combinations of the polynucleotide sequences of the present disclosure may be used to facilitate high-level expression ofone or more gene products of interest (e.g., surface antigens) in recombinant hosts. In addition, the present disclosure provides for codon-optimization of polynucleotide sequences encoding a protein product to be expressed, e.g., a surface antigen, based on the codon preferences of the recombinant organism chosen for expression. The methods of the present disclosure involve combining these polynucleotide sequences in various ways to facilitate consistent, high-level expression of one or more gene product of interest in a selected recombinant host organism.

Introduction of Promoters Upstream of Endogenous Host Sequences

In some embodiments, the methods of the present disclosure involve inserting a polynucleotide promoter sequence of the present disclosure into the genome of a suitable host organism, e.g., a *Neisseria* host cell, upstream (e.g., in the 5' direction) of a native gene, e.g., a native surface antigen gene. The recombinant host cells are then cultured under conditions that facilitate expression of the native gene. In embodiments where *N. meningitidis* are chosen as the host organsims, vesicles produced by the host cells can then be isolated and used to prepare vaccine compositions that can be administered to a subject in order to induce an immunological response in the subject.

For example, in some embodiments, a chimeric promoter (e.g., X1-X7) or a domain deletion promoter (e.g., S1-S3) is inserted into the genome of a Neisserial strain upstream of a native fHbp gene. Introduction of the engineered promoter sequence facilitates high levels of expression of the fHbp gene.

Introduction of Expression Constructs

In some embodiments, the methods of the present disclosure involve inserting an expression construct comprising an engineered promoter operably linked to one or more polynucleotide sequences that encode a gene product of interest, e.g., a protein of interest into the genome of a host organism. In some embodiments, a transcription terminator sequence is operably linked to the 3' end of the polynucleotide sequence encoding a gene product of interest. For example, in some embodiments, an expression construct comprising a chimeric promoter (e.g., X1-X7) or a domain deletion promoter (e.g., S 1-S3) operably linked to a polynucleotide sequence encoding fHbp and operably linked to a transcription terminator having the sequence described above is inserted into a suitable region of the genome of the Neisserial host cell (e.g., the lpxL1 locus).

In some embodiments, an expression construct may be inserted into the genome of the host in a location that disrupts expression of one or more host genes. For example, in some embodiments, an expression construct may be inserted into the genome of a host in a location that disrupts expression of a gene that facilitates production of endotoxin (lipopolysaccharide, LPS). The resulting recombinant host is an endotoxin knockout host, which may be useful in the production of vaccines with reduced endotoxin.

In some embodiments, a first engineered promoter sequence is inserted into the genome of a host cell upstream of a native gene, e.g., a native surface antigen gene, and an expression construct comprising a second engineered promoter sequence operably linked to a polynucleotide sequence encoding a gene product of interest is inserted into the genome of the host cell in a suitable location within the genome of the host cell (e.g., the lpxL1 locus).

In some embodiments, the first and second promoter sequences are the same, while in other embodiments, the first and second promoter sequences are different. For example, in some embodiments, chimeric promoter X1 is inserted into the genome of a Neisserial cell upstream of a native fHbp gene and an expression construct comprising chimeric promoter X1 operably linked to a polynucleotide sequence encoding fHbp is inserted into the lpxL1 locus of the host Neisserial cell. In other embodiments, chimeric promoter X1 is inserted into the genome of a Neisserial strain upstream of a native fHbp gene and an expression construct comprising domain deletion promoter S1 operably linked to a polynucleotide sequence encoding fHbp is inserted into the lpxL1 locus of the host Neisserial cell.

Introduction of an engineered promoter upstream of a native gene, e.g., a native surface antigen gene, results in increased expression of the gene, while introduction of a second copy of the gene driven by an engineered promoter at another location within the host genome can facilitate increased expression even further. In some embodiments, additional expression constructs comprising one or more polynucleotide sequences that encode one or more gene products of interest (e.g., one or more proteins of interest) may be inserted into the host cell genome as well. In some embodiments, introduction of a third, fourth, or fifth copy of a gene product of interest (e.g., a surface antigen of interest) driven by an engineered promoter increases expression of the gene product of interest even further.

In some embodiments, several different gene products of interest may be expressed in the same host cell. For example, in some embodiments, an engineered promoter is inserted upstream of a first native surface antigen gene (e.g., fHbp), and one or more expression constructs comprising different surface antigen genes (e.g., NspA) driven by the same or different engineered promoter sequences are also inserted into the genome of the host cell. The resuling host cell expresses two or more different surface antigens, and may be useful in the production of vaccines.

Vectors and Methods for Introducing Genetic Material into Neisserial Host Cells

Methods and compositions that can be readily adapted to provide for genetic modification of a host cell with a nucleic acid construct of the present disclosure are known in the art. Exemplary vectors and methods are provided in, e.g., WO 02/09746 and O'Dwyer et al. *Infect Immun* 2004; 72:6511-80.

Methods for transfer of genetic material into a host cell include, for example, conjugation, transformation, electroporation, calcium phosphate methods and the like. In general, the method for transfer should provide for stable expression of the introduced construct. The construct can be provided as an inheritable episomal element (e.g., plasmid) or can be genomically integrated.

Suitable vectors will vary in composition depending on what type of recombination event is to be performed. Integrative vectors can be conditionally replicative or can be suicide plasmids, bacteriophages, transposons or linear DNA fragments obtained by restriction hydrolysis or PCR amplification. Selection of the recombination event can be accomplished by use of selectable genetic markers such as genes conferring resistance to antibiotics (for instance kanamycin, erythromycin, chloramphenicol, or gentamycin), genes conferring resistance to heavy metals and/or toxic compounds, or genes complementing auxotrophic mutations (for instance pur, leu, met, aro).

Vaccine Production

Antigenic compositions contemplated by the present disclosure generally include vesicles prepared from Neisserial cells that express a surface antigen. As referred to herein, "vesicles" is meant to encompass outer membrane vesicles as well as microvesicles (which are also referred to as blebs).

Antigenic compositions for use in the production of vaccines can contain outer membrane vesicles (OMV) prepared from the outer membrane of a cultured strain of *Neisseria meningitidis* spp. genetically modified to express a surface antigen, e.g. fHbp. OMVs may be obtained from *Neisseria meningitidis* grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

Antigenic compositions can contain microvesicles (MV) (or "blebs") containing surface antigens, where the MV or blebs are released during culture of a *Neisseria meningitidis* strain genetically modified to express a surface antigen. For example, MVs may be obtained by culturing a strain of *Neisseria meningitidis* in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An exemplary strain that produces high levels of blebs is described in PCT Publication No. WO 01/34642. In addition to bleb production, strains for use in MV production may also be selected on the basis of production of other surface antigens, where strains that produce higher levels of specific surface antigens may be of particular interest (for examples of *N. meningitidis* strains having different NspA production levels, see, e.g., Moe et al. (1999 *Infect. Immun.* 67: 5664)). Other strains of interest for use in production of blebs include strains having an inactivated GNA33 gene, which encodes a lipoprotein required for cell separation, membrane architecture and virulence (see, e.g., Adu-Bobie et al. (2004) *Infect Immun.* 72:1914-1919).

The antigenic compositions of the present disclosure can contain vesicles from one strain, or from 2, 3, 4, 5 or more strains, which strains may be homologous or heterologous, usually heterologous, to one another. For example, the strains may be homologous or heterologous with respect to a particular surface antigen, such as porA and/or fHbp. The vesicles can be prepared from strains that express more than one variant or subvariant of a specific surface antigen (e.g., 1, 2, 3, or more variants of fHbp) which may be composed of fHbp amino acid sequences from different variants (v.1, v.2, or v.3) or subvariants (e.g., a subvariant of v.1, v.2, or v.3).

The antigenic compositions can comprise a mixture of OMVs and MVs presenting the same or different surface antigens, where the surface antigens may optionally present epitopes from different combinations of variants and/or subvariants and where the OMVs and/or MVs may be from the same or different strains. Vesicles from different strains can be administered as a mixture, or can be administered serially.

Where desired (e.g., where the strains used to produce vesicles are associated with endotoxin or particularly high levels of endotoxin), the vesicles can optionally be treated to reduce endotoxin, e.g., to reduce toxicity following administration. Although potentially less desirable, reduction of endotoxin can be accomplished by extraction with a suitable detergent (for example, BRIJ-96, sodium deoxycholate, sodium lauroylsarcosinate, Empigen BB, Triton X-100, TWEEN 20 (sorbitan monolaurate polyoxyethylene), TWEEN 80, at a concentration of 0.1-10%, preferably 0.5-2%, and SDS). Where detergent extraction is used, it is preferable to use a detergent other than deoxycholate.

The vesicles of the antigenic compositions can be prepared without detergent, e.g., without use of deoxycholate. Although detergent treatment is useful to remove endotoxin activity, it may negatively impact the surface antigen proteins in preparation. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from *Neisseria* mutants in which lipooligosaccharide or other antigens that may be undesirable in a vaccine (e.g. Rmp) is reduced or eliminated.

Vesicles can be prepared from *N. meningitidis* strains that contain genetic modifications that result in decreased or no detectable toxic activity of lipid A. For example, such strain can be genetically modified in lipid A biosynthesis (Steeghs et al. (1999) *Infect Immun* 67:4988-93; van der Ley et al. (2001) *Infect Immun* 69:5981-90; Steeghs et al. (2004) *J Endotoxin Res* 10:113-9; Fissha et al, (2005) *Infect Immun* 73:4070). The immunogenic compositions may be detoxified by modification of LPS, such as downregulation and/or inactivation of the enzymes encoded by lpxL1 or lpxL2, respectively. Production of a penta-acylated lipid A made in lpxL1 mutants indicates that the enzyme encoded by lpxL1 adds the C12 to the N-linked 3-OH C14 at the 2' position of GlcN II. The major lipid A species found in lpxL2 mutants is tetra-acylated, indicating the enzyme encoded by lpxL2 adds the other C12, i.e., to the N-linked 3-OH C14 at the 2 position of GlcN I. Mutations resulting in a decreased (or no) expression of these genes (or decreased or no activity of the products of these genes) result in altered toxic activity of lipid A (van der Ley et al. (2001) *Infect Immun* 69:5981-90). Tetra-acylated (lpxL2 mutant) and penta acylated (lpxL1 mutant) lipid A are less toxic than the wild-type lipid A. Mutations in the lipid A 4'-kinase encoding gene (lpxK) also decrease the toxic activity of lipid A. Of particular interest for use in production of vesicles (e.g., MV or OMV) are *N. meningitidis* strains genetically modified so as to provide for decreased or no detectable functional lpxL1-encoded protein, e.g., where the *Neisseria* bacterium (e.g., *N. meningitidis* strain) is genetically modified to provide for decreased or no activity of a gene product of the lpxL1 gene. For example, the *Neisseria* bacterium can be genetically modified to have an lpxL1 gene knockout, e.g., where the lpxL1 gene is disrupted. See, e.g., US Patent Publication No. 2009/0035328. The *Neisseria* bacterium can be genetically modified to provide for decreased or no activity of a gene product of the lpxL1 gene and/or the lpxL2 gene. Such vesicles provide for reduced toxicity as compared to *N. meningitidis* strains that are wild-type for LPS production, while retaining immunogenicity of a surface antigen, e.g., fHbp.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoPc), or low Mg++ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF secretion from human monocytes.

Polymyxin B resistant strains are also suitable for use, as such strains have been shown to have reduced LPS toxicity (see, e.g., van der Ley et al. (1994) In: Proceedings of the ninth international pathogenic *Neisseria* conference. The Guildhall, Winchester, England). Alternatively, synthetic peptides that mimic the binding activity of polymyxin B may be added to the antigenic compositions to reduce LPS toxic activity (see, e.g., Rustici et al. (1993) *Science* 259:361-365; Porro et al. (1998) *Prog Clin Biol Res.* 397:315-25).

Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

Kits

Also provided by the present disclosure are kits for using the polynucleotide sequences disclosed herein to practice the methods described above. Kits may contain one or more polynucleotide sequences of the present disclosure in the form of vectors or expression constructs to be used in the production of additional expression constructs and/or recombinant *Neisseria meningitidis* strains. Kits may also contain one or more polynucleotide sequences encoding an antigen to be expressed in a *Neisseria meningitidis* host strain in the form of a vector or an expression construct. Kits may further include one or more recombinant *Neisseria meningitidis* strains that comprise one or more of the engineered promoter sequences disclosed herein and/or a polynucleotide sequence encoding an antigen and/or a transcription terminator sequence.

In addition to the above-mentioned components, the kits can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); and the like.

Methods and Materials

The following methods and materials were used in the Examples below.

Bacterial Strains

The six N. meningitidis strains used in the examples that follow are listed in Table 1.

TABLE 1

N. meningitidis strains used in the following examples.

| Strain Name | Alternative Strain Designation | Capsular Group | fHbp ID |
|---|---|---|---|
| CH21A | Senegal 1/99 | A | 5 |
| CH248B | H44/76 | B | 1 |
| CH253B | NZ98/254 | B | 14 |
| CH36W | BuFa1/03 | W | 23 |
| CH38W | Su1/06 | W | 9 |
| CH164X | Uganda 5/07 | X | 74 |

Measurement of fHbp Expression by Western Blot fHbp expression was measured by a quantitative Western blot, which was performed as previously reported (Pajon, Vaccine 2010 Feb. 25; 28(9):2122-9) with minor changes. For fHbp sequences in variant group 1, anti-fHbp mAb JAR 3 was used for detection of fHbp sequence variants ID 1, 4 or 9, and JAR 5 was used for ID 74. For fHbp in variant groups 2 or 3, anti-fHbp mAb JAR 31 was used (Beernink, Infect Immun. 2008 September; 76(9):4232-40). The results for the test strains were reported as percentages of the amount of fHbp expressed by bacterial cells from the corresponding reference strains H44/76 or 8047 with high expression of fHbp variant 1 (ID 1) and 2 (ID 77), respectively.

Flow Cytometry

Binding of mouse anti-fHbp mAbs to live meningococci was measured to assess the relative amounts of fHbp on the bacterial surface accessible to antibody in mutants engineered to have increased or decreased fHbp relative to a control. Flow cytometry was performed as described previously using a combination of two mouse anti-fHbp mAbs, JAR4 and JAR5 (Welsch, J Infect Dis. 2008 Apr. 1; 197(7): 1053-61), each at a final concentration of 10 μg/mL. Controls in the assay included a mouse mAb, specific for group A (JW-A1) or B (SEAM 12) polysaccharides (Moe, Mol. Immunol. 2006 March; 43(9):1424-31).

Example 1

High fHbp Levels Driven by Engineered Promoters in a Series of Isogenic Mutants of CH21A, a Serogroup a Strain Expressing fHbp ID 5.

Figure 7:
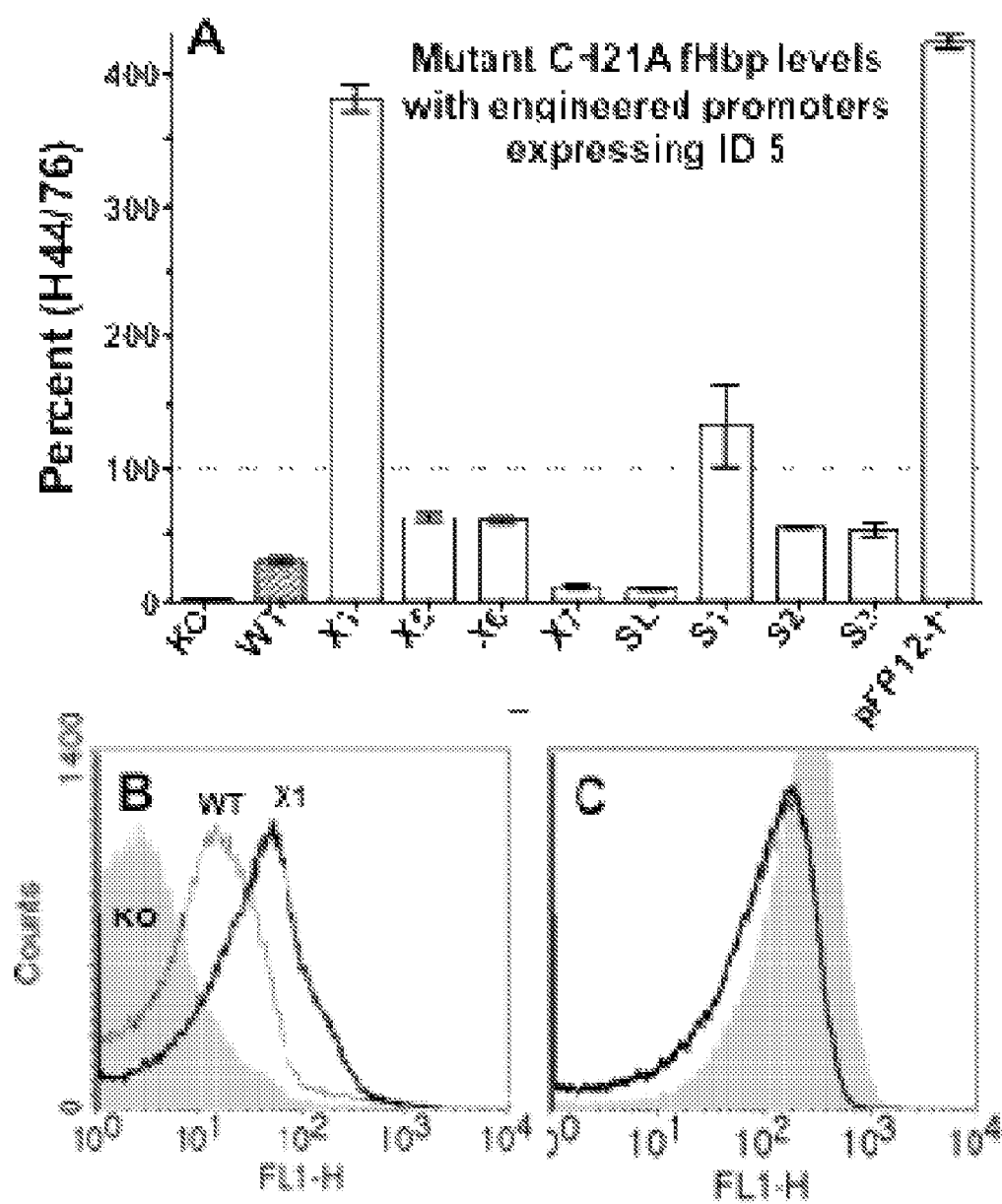

Neisseria meningitidis strain CH21A, which is a serogroup A strain expressing fHbp ID 5, was used to test the ability of the engineered promoters of the present disclosure to drive expression. Chimeric promoters and domain deletion promoters were operatively inserted into the genome of the CH21A host strain upstream of the fHbp gene, and subsequent expression of fHbp was measured by quantitative Western blot. The results are shown in FIG. 7. Values in Panel A are percentages compared with expression of fHbp by the reference group B strain H44/76, which is a relatively high expresser of fHbp ID 1 (variant group 1). Error bars represent ranges of values measured in two independent experiments. Control strains include the parent wildtype strain and a fHbp KO, which is a mutant with the fHbp gene inactivated and which does not produce any fHbp protein; WT, CH21A wild type isolate which is a naturally low fHbp ID 5 producer; X1, X5-X7, chimeric promoters; SL and S1-S3, domain deletion promoters; pFP12-f, plasmid construct that replicates in neisseria expressing high levels of fHbp, but not suitable for vaccine production due to plasmid instability. X1 promoter is able to drive fHbp expression levels to similar levels to those seen from the plasmid-based system pFP12-f. Panel B shows flow cytometry data using monoclonal antibodies specific for fHbp (JAR4 and JAR5 mixture at a total concentration of 4 μg/mL) for KO (light gray), WT (dashed line), and X1 (solid line) strains. Panel C shows flow cytometry data for anti-capsular monoclonal antibody JW-A1, which recognizes capsular group A polysaccharide. The data show similar expression levels for the capsular polysaccharide among all tested strains, although the fHbp KO mutant seemed to have slightly higher capsular content.

Example 2

Figure 8:
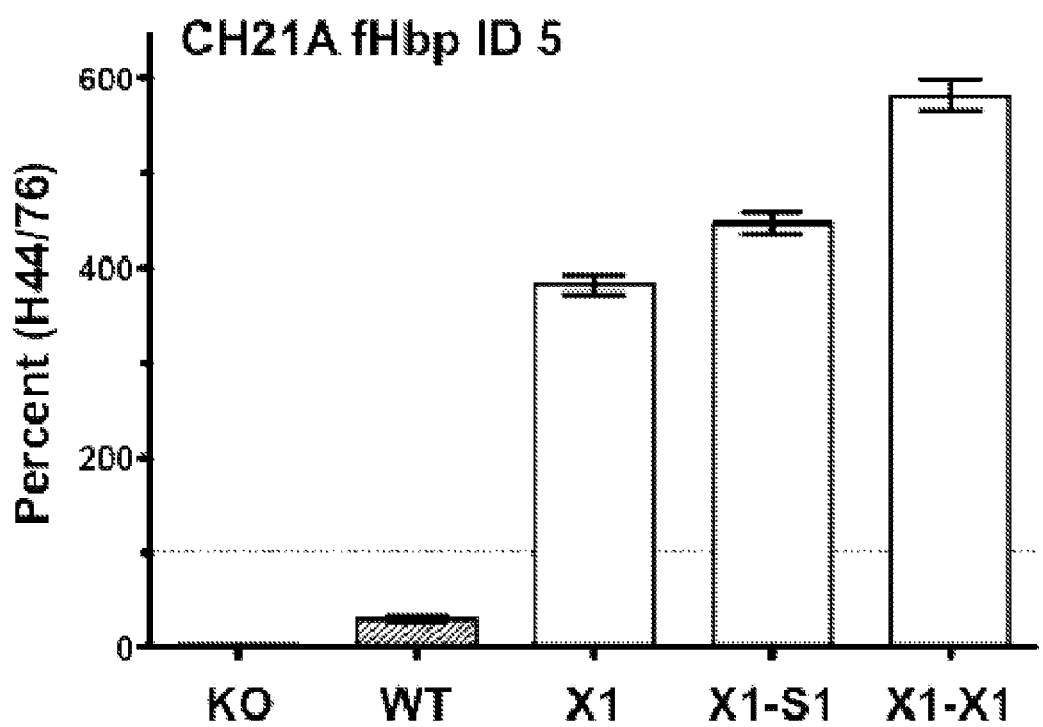

Insertion of a Second Copy of the fHbp Gene Augments fHbp Levels in CH21A As Compared to Single-Copy or Wild Type Strains Chimeric promoter X1 was operably inserted upstream of the fHbp gene in Neisseria meningitidis strain CH21A. In addition, an expression construct comprising the chimeric promoter X1 or domain deletion promoter S1 operably linked to a copy of the fHbp gene was inserted into the lpxL1 locus of the host strain to provide a second copy of the fHbp gene. Subsequent expression of fHbp was measured by a quantitative Western blot. The results are shown in FIG. 8. Values are mean percentages compared with expression of fHbp by the reference group B strain H44/76, which is a relatively high expresser of fHbp ID 1 (variant group 1). Error bars represent ranges in values measured in two independent experiments. KO, a mutant that in which the fHbp gene was inactivated, which did not express the protein; WT, wild type isolate which is a naturally low fHbp ID 5 producer; X1, chimeric promoter; X1-S1, a mutant containing X1-fHbp in the fHbp native locus and a second copy of the fHbp gene in the form of a S1-fHbp genetic cassette inserted into the lpxL1 locus; X1-X1 a mutant containing X1-fHbp in the fHbp native locus and a second copy of the X1-fHbp genetic cassette inserted into the lpxL1 locus. The insertion of the second copy into the lpxL1 locus also resulted in the attenuation of endotoxic activity. These data indicate that multiple copies of the engineered promoter-gene of interest can drive increased expression levels regardless of the location in the genome.

Example 3

High fHbp Levels Driven by Chimeric Promoters

Figure 9:
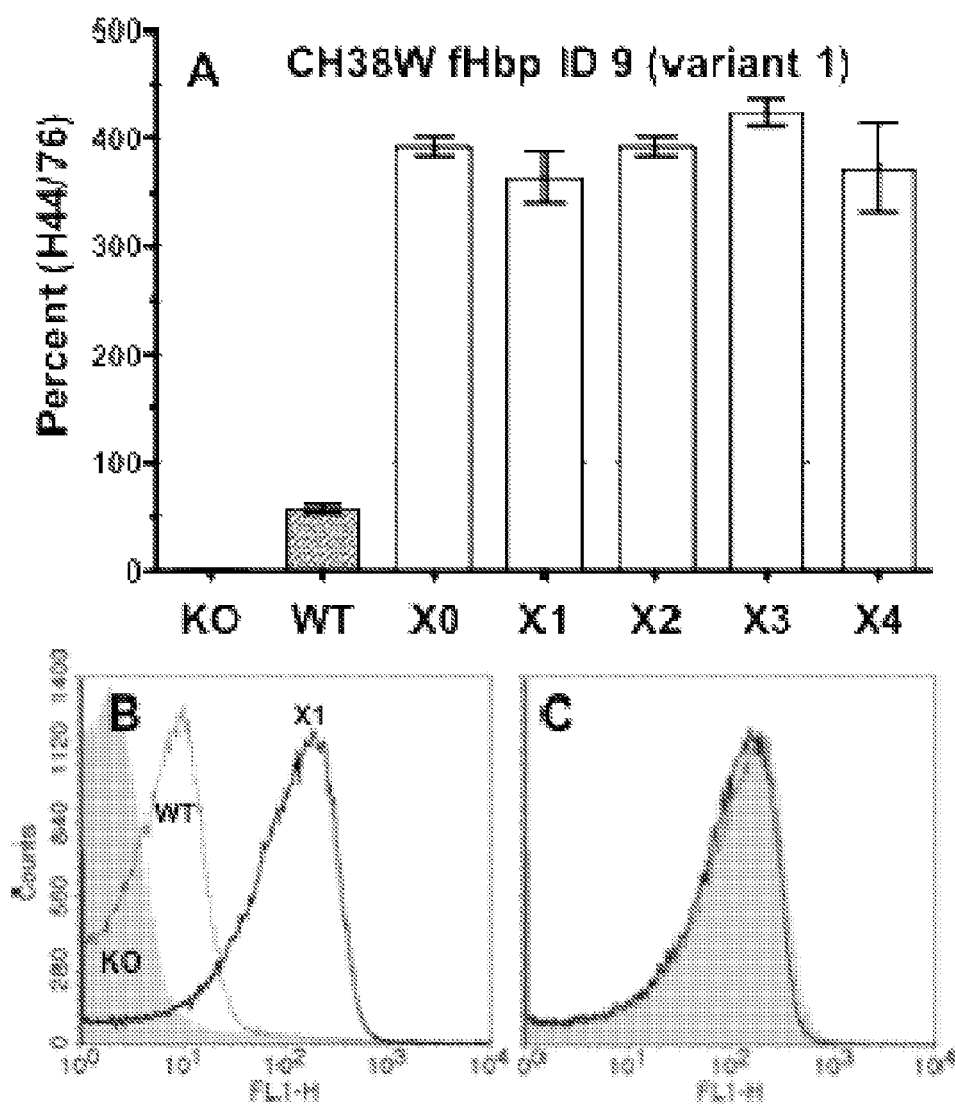

Neisseria meningitidis strain CH38W, a serogroup W-135 strain expressing fHbp ID 9, was used to test the ability of the chimeric promoters of the present disclosure to drive expression. Chimeric promoters X1-X4 were operatively inserted into the genome of the CH38W host strain upstream of the fHbp gene, and subsequent expression of fHbp was measured by quantitative Western blot. The results are shown in FIG. 9. Values are mean percentages (+/− ranges from two experiments) compared with expression of fHbp by the reference group B strain H44/76, which is a relatively high expresser of fHbp ID 1 (variant group 1). KO, a mutant in which the fHbp gene was inactivated by the insertion of an antibiotic marker (rendering the strain incapable of producing any detectable fHbp protein); WT, CH38W wild type isolate which is a naturally low producer of fHbp ID 9; X1-X4, chimeric promoters. Expression levels with these promoters were similar to or higher than that achieved by the native porA promoter (X0). Panel B shows flow cytometry data collected using monoclonal antibodies specific for fHbp (JAR4 and JAR5 mixture at 4 ug/mL) for KO (light gray), WT (dashed line), and X1 (solid line) strains. Panel C shows flow cytometry data collected using an anti-capsular monoclonal antibody JW-W1 that recognizes capsular group W135 polysaccharide.

Example 4

Figure 10:
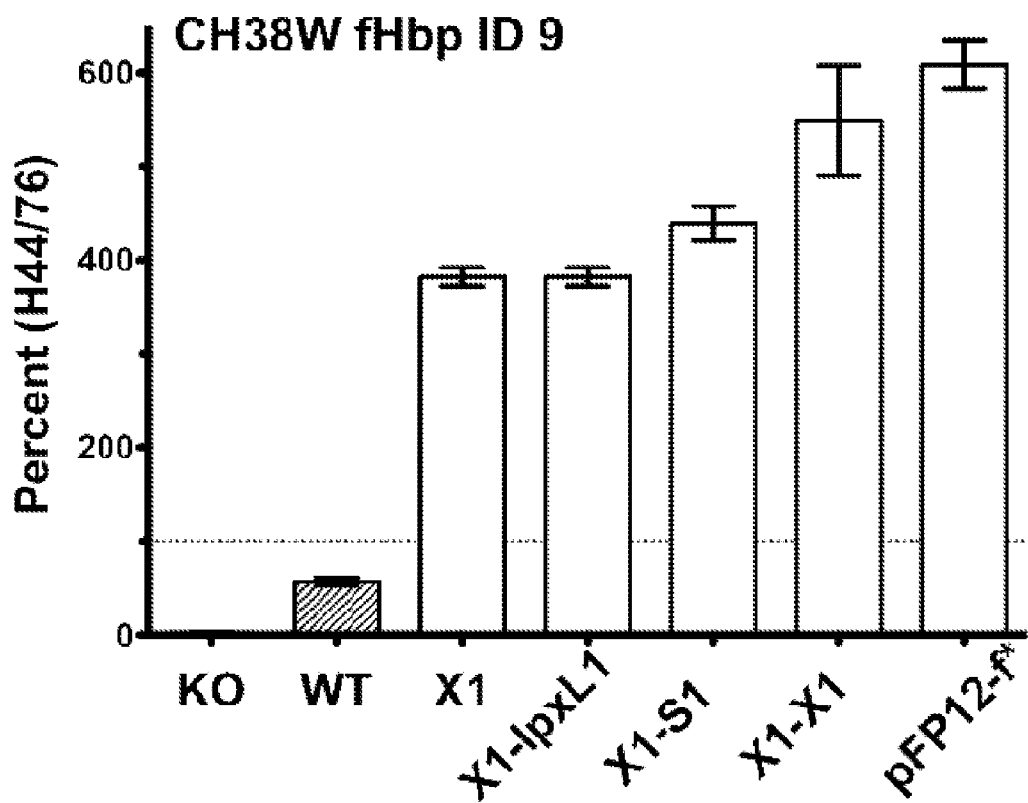

Insertion of a Second Copy of the fHbp Gene Driven by an Engineered Promoter into the lpxL1 Locus in Addition to Insertion of an Engineered Promoter At the Native fHbp Site Chimeric promoter X1 was operably inserted upstream of the fHbp gene in *Neisseria meningitidis* strain CH38W. In addition, an expression construct comprising the chimeric promoter X1 or domain deletion promoter S1 operably linked to a copy of the fHbp gene was inserted into the lpxL1 locus of the host strain to provide a second copy of the fHbp gene. Subsequent expression of fHbp was measured by quantitative Western blot. The results are shown in FIG. 10. KO, a mutant with an inactivated fHbp gene (and no fHbp protein expression); WT, wild type isolate which is a naturally low fHbp ID 5 producer; X1, isogenic mutant constructed substituting native fHbp promoter with X1 promoter; X1-lpxL1, a mutant that has the native fHbp gene inactivated and a copy of X1-fHbp expression construct inserted into the lpxL1 locus; X1-S1, a mutant containing X1-fHbp in the fHbp native locus and a second copy of the fHbp gene in the form of a S1-fHbp genetic cassette inserted into the lpxL1 locus;

X1-X1, a mutant containing X1-fHbp in the fHbp native locus and a second copy of the X1-fHbp genetic cassette inserted into the lpxL1 locus. Values are mean percentages (+/− ranges in replicate experiments) compared with expression of fHbp by the reference group B strain H44/76, which is a relatively high expresser of fHbp ID 1 (variant group 1).

Example 5

Over-Production of fHbp Model Antigen by CH248B Capsular Group B Strain

Figure 11:
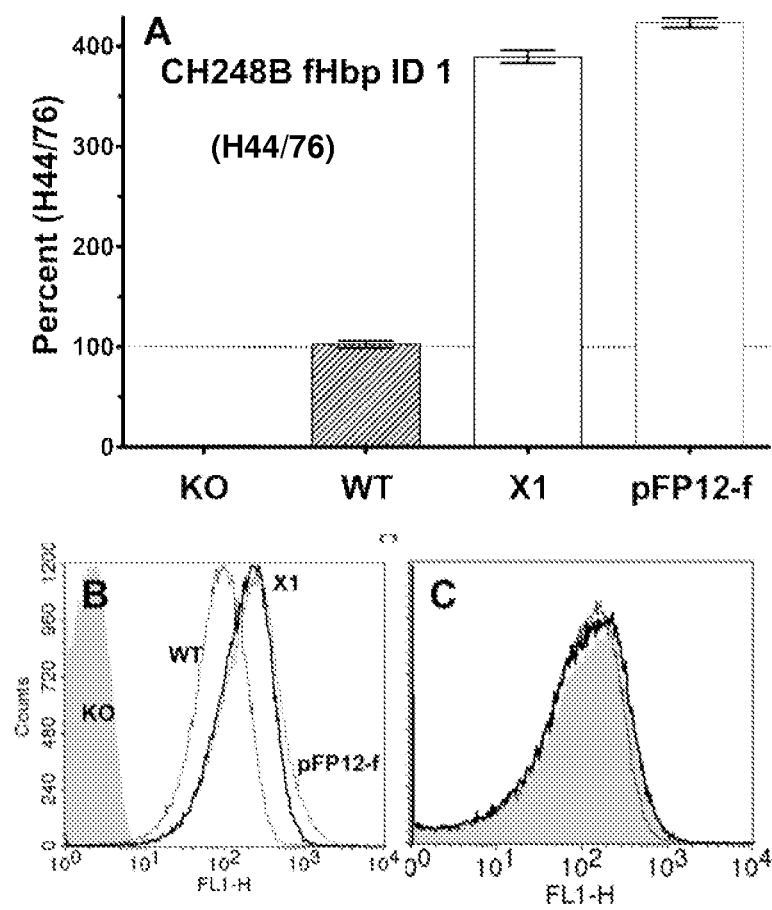

*Neisseria meningitidis* strain CH248B, a capsular group B strain, was used to test the ability of the chimeric promoters of the present disclosure to drive expression. This strain also is referred to as H44/76. Chimeric promoter X1 was operatively inserted into the genome of the CH248B host strain upstream of the fHbp gene, and subsequent expression of fHbp was measured by quantitative Western blot. The results are shown in FIG. 11. Values are mean percentages (+/− ranges in replicate experiments) compared with expression of fHbp alone, as this is the reference group B strain and a relatively high expresser of fHbp ID 1 (variant group 1). KO, a mutant that lacks fHbp gene and protein; WT, wild type isolate which is a naturally high fHbp ID 1 producer; X1, isogenic mutant constructed substituting native fHbp promoter with X1 promoter; pFP12-f, strain containing a plasmid construct that replicates in *Neisseria* expressing high levels of fHbp ID 1, but is not suitable for vaccine production due to plasmid instability. Panel B shows flow cytometry data collected using monoclonal antibodies specific for fHbp (JAR4 and JAR5 mixture at 4 ug/mL) for KO (light gray), WT (dashed line), X1 (solid line), and pFP12-f (dotted line) strains. The X1 chimeric promoter was able to drive surface fHbp expression levels to similar levels to that of the plasmid based system pFP12-f. Panel C shows flow cytometry data collected using an anti-capsular monoclonal antibody SEAM-12 that recognizes capsular group B polysaccharide.

Example 6

Over-Production of fHbp Model Antigen in CH253B Capsular Group B Strain

Figure 12:
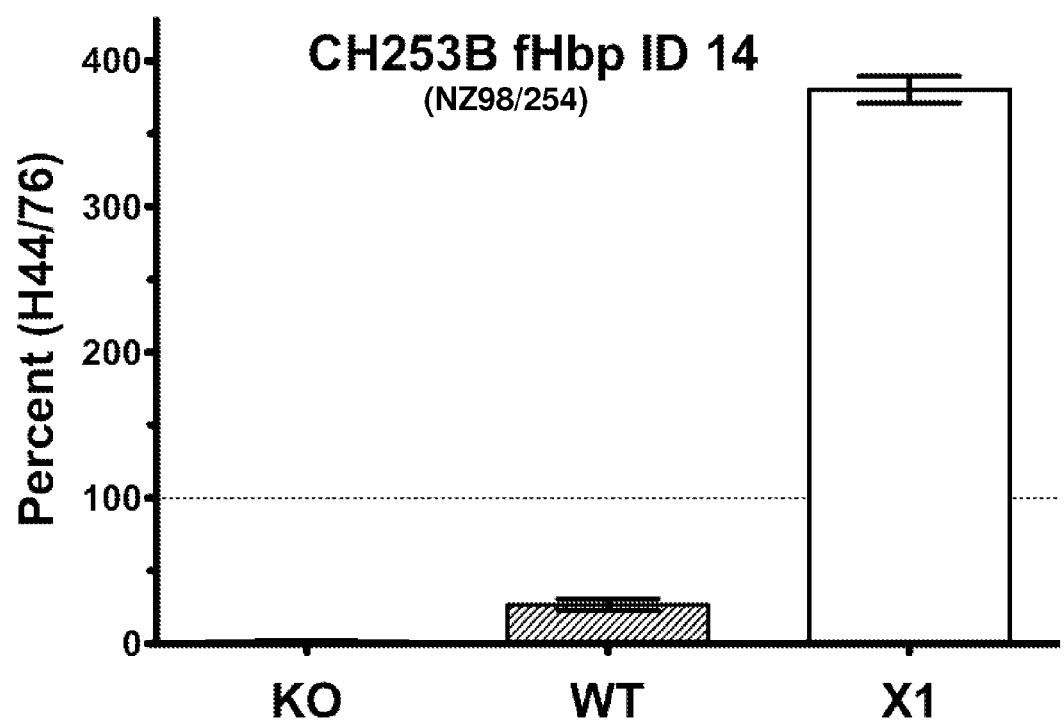
FIG. 12 shows quantitative Western blot data measuring fHbp ID 14 expression levels among CH253B (also known as NZ98/254) derivatives.

*Neisseria meningitidis* strain CH253B, a capsular group B strain expressing fHbp ID 14, was used to test the ability of chimeric promoter X1 to drive expression. Chimeric promoter X1 was operatively inserted into the genome of the CH253B host strain (also known as NZ98/254) upstream of the fHbp gene, and subsequent expression of fHbp was measured by quantitative Western blot. The results are shown in FIG. 12. Values are mean percentages (+/− ranges in replicate experiments) compared with expression of fHbp by the reference group B strain H44/76, which is a relatively high expresser of fHbp ID 1 (variant group 1). KO, a mutant that lacks fHbp gene and protein; WT, wild type isolate which is a naturally low fHbp ID 14 producer; X1, isogenic mutant constructed substituting native fHbp promoter with X1 promoter. Chimeric promoter X1 achieved significantly higher expression of fHbp as compared to the wild type isolate.

Example 7

Over-Production of fHbp Model Antigen by CH164X Capsular Group X Strain

Figure 13:
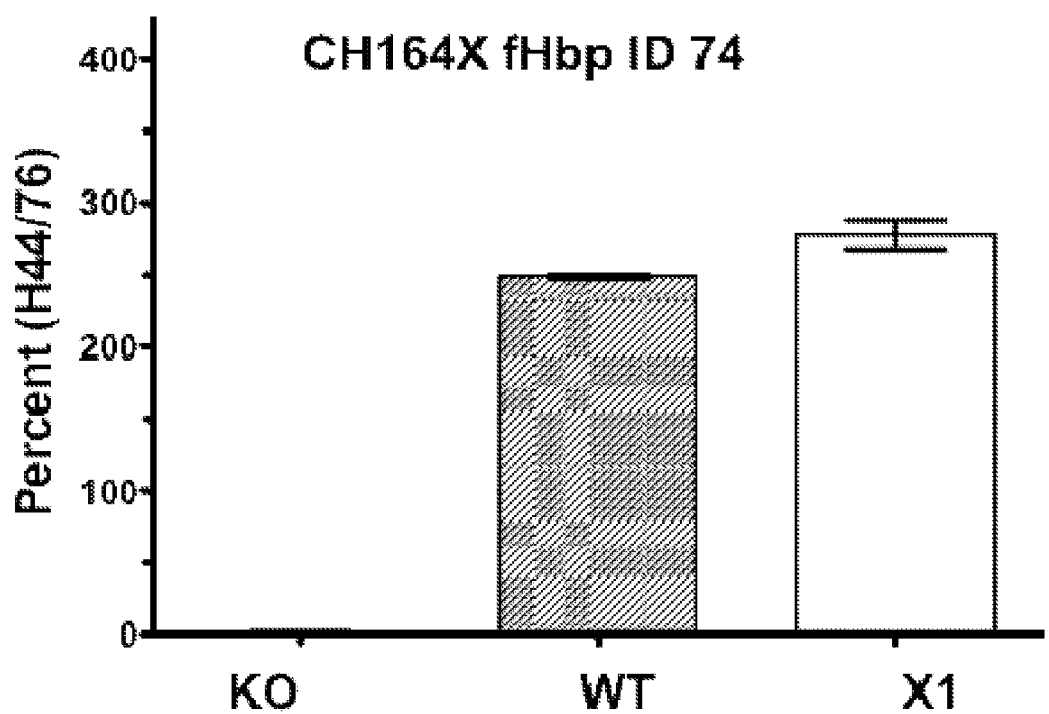
FIG. 13 shows expression levels of fHbp ID 74 among engineered CH164X Neisserial isolates as measured by a quantitative Western blot.

*Neisseria meningitidis* strain CH164X, a capsular group X strain expressing fHbp ID 74, was used to test the ability of chimeric promoter X1 to drive expression. Chimeric promoter X1 was operatively inserted into the genome of the CH164X host strain upstream of the fHbp gene, and subsequent expression of fHbp was measured by quantitative Western blot. The results are shown in FIG. 13. KO, a mutant that lacks fHbp gene and protein; WT, wild type isolate which is a naturally low fHbp ID 74 producer; X1, isogenic mutant constructed substituting native fHbp promoter with X1 promoter. Chimeric promoter X1 achieved significantly higher expression of fHbp as compared to the wild type isolate.

Example 8

Over-Production of fHbp Variant 2 Model Antigen by CH36W Capsular Group W135 Strain

*Neisseria meningitidis* strain CH36W, a capsular group W135 strain expressing fHbp ID 23 (variant 2), was used to test the ability of chimeric promoter X1 to drive expression. Chimeric promoter X1 was operatively inserted into the genome of the CH36W host strain upstream of the fHbp ID 23 gene, and subsequent expression of fHbp was measured by quantitative Western blot. The results are shown in FIG. 14. Panel A shows quantitative Western blot data of expression levels in CH36W mutants. Values are mean percentages (+/− ranges in two replica experiments) compared with expression of fHbp by the reference group B strain 8047, which is a relatively high expresser of fHbp ID 77 (variant group 2). KO, a mutant in which the fHbp gene was inactivated and which does not express the protein; WT, wild type isolate which is a naturally low fHbp ID 23 producer; X1, chimeric promoter. Panel B shows flow cytometry data collected using monoclonal antibodies specific for fHbp (JAR31, at 4 ug/mL) for KO (light gray), WT (dashed line), and X1 (solid line) strains. Panel C shows flow cytometry data collected using and anticapsular monoclonal antibody JW-W1 used as control that recognizes capsular group W135 polysaccharide. Collectively, the data illustrates the ability of engineered promoters to drive increased expression of a variant group 2 fHbp.

Example 9

Use of a Transcription Terminator Sequence to Increase Expression

*Neisseria meningitidis* strain CH21A, a capsular group A strain, was used to evaluate the influence of a transcription terminator sequence on the expression level of fHbp ID 5. An X1 promoter sequence was inserted into the genome of the CH21A strain upstream of a sequence encoding fHbp ID 5. In a first recombinant host, the native transcription terminator having the sequence TAACCATTGTGAAAATGCCGTC-CGAACACGATAATTTACCGTTCGGACGG CATTTGTA (SEQ ID NO: 53) was operably linked to the 3' end of the fHbp ID 5 coding sequence. In a second recombinant host, the native transcription terminator sequence was deleted. Both recombinant hosts were then cultured under the same conditions, and the expression level of fHbp ID 5 was compared between the two hosts. Results are shown in FIG. 15. The expression level of fHbp ID 5 was higher in the host containing the transcription terminator sequence, indicating that the transcription terminator sequence facilitates higher expression.

Example 10

Determination of Codon Usage Frequency for Use in Codon Optimization

Codon usage frequency was determined in FAM18 and Z2491, two different *Neisseria meningitidis* strains. Codon usage mean and standard deviation results for the two strains are shown in FIGS. 16 and 17. For each amino acid residue, the codon with the highest mean usage value was identified. Next, a polynucleotide sequence encoding fHbp ID 9 was engineered for expression in each strain based on the codon usage results. The fHbp ID 9 coding sequence was uploaded to an online codon optimization tool, and the codon usage preferences for each strain were provided. The online codon optimization tool replaced redundant codons in the coding sequence with the preferred codon for each amino acid residue. A comparison of an original fHbp sequence with the codon-optimized sequence is shown in FIG. 18.

Codon optimization was also performed for polynucleotide sequences encoding fHbp ID 23, ID 4, ID 28, ID 1, ID 14, ID 45, ID 55, ID 19, ID 77, NspA (nmb0663), NspA (nmc0612, nma0862), NHbp (nmb2132), TbpB (Tbp2, nmb0461), TbpA (tbp1, nmb0461), LbpB (nmb1541), LbpA (nmb1540), Opacity protein (Class 5, nmb1053), NadA (nmb1994), PorA (nmb1429), and feta (nmb1988). The codon-optimized sequences are shown in FIGS. 19-38.

Example 11

Use of a Single Engineered Promoter Sequence to Drive Expression of Multiple Surface Antigens Engineered promoter sequences were used to drive expression of multiple polynucleotides encoding surface antigens that were organized in an operon-like fashion. FIG. 39, Panel A. This allowed for over-expression of multiple surface antigens under the control of a single copy of the engineered promoter. The system can be used to express a plurality of polynucleotides at the same time due to the high output of the engineered promoters. Examples of tested surface antigen-encoding polynucleotide sequence configurations are provided in FIG. 39, Panels B and C, where fHbp is over-expressed together with NspA (Panel B) and both TbpB and TbpA (Panel C).

To further illustrate this approach, engineered promoter X1 was operably inserted upstream of an fHbp-encoding polynucleotide sequence in *Neisseria meningitidis* strain CH38W, a capsular W-135 strain expressing fHbp ID 9 and NspA, both at low levels. The NspA-encoding polynucleotide sequence was operably inserted just downstream of the fHbp-encoding sequence. The transcription terminator sequence from fHbp was operably linked to the 3' end of the NspA-encoding polynucleotide sequence. Subsequent expression of both fHbp and NspA was measured by quantitative Western blot using monoclonal antibodies specific to each of the antigens. FIG. 40 shows quantitative Western blot data of expression levels in the CH38W mutant strain, containing both the fHbp-encoding polynucleotide sequence and the NspA-encoding polynucleotide sequence under the control of the X1 engineered promoter (FIG. 39, Panel B). Values shown are mean fluorescence units (+/− ranges in two replicates) compared to the expression of either fHbp or NspA in the wild type (WT) isolate. Both fHbp and NspA expression levels in the mutant are significantly higher than in the WT strain. These data indicate that expression of multiple polynucleotide sequences can be driven to high levels by a single engineered promoter.

What is claimed is:

1. A promoter, comprising:

a 5' portion of a native *N. meningitidis* porA promoter comprising the sequence ATGGTT (SEQ ID NO:2);

a spacer portion; and a 3' portion of a native *N. meningitidis* porA promoter comprising the sequence TATAAT (SEQ ID NO:3), wherein the spacer comprises a sequence of the formula $N^1$-TTTCA-$N^2$ (SEQ ID NO:1), wherein $N^1$ is $X^a$(T/A)(T/A)(T/A)(T/G)(C/G)(C/G)(C/G/A)(G/T)C$X^b$ and $N^2$ is $X^c X^d X^e$, wherein:

$X^a$ is present or absent, and when present is T or A;

$X^b$ is present or absent, and when present is A or C;

$X^c$ is present or absent, and when present is T or G;

$X^d$ is present or absent, and when present is A or G; and $X^e$ is present or absent, and when present is G, wherein the 5' portion, the spacer, and the 3' portion are operably linked to provide for transcription in *N. meningitidis*.

2. The promoter of claim 1, wherein the spacer comprises the sequence ATATGCCTCCTTTCATA (SEQ ID NO:4).

3. The promoter of claim 1, wherein the spacer comprises the sequence TATATGCCTCCTTTCATA (SEQ ID NO:5).

4. The promoter of claim 1, wherein the spacer comprises the sequence ATAATGCCTCCTTTCATA (SEQ ID NO:6).

5. The promoter of claim 1, wherein the spacer comprises the sequence ATATGCATCATTTCATA (SEQ ID NO:7).

6. The promoter of claim 1, wherein the spacer comprises the sequence TTTTGCGGGCTTTCATA (SEQ ID NO:8).

7. The promoter of claim 1, wherein the spacer comprises the sequence TTTTGCGGGCTTTCAGGG (SEQ ID NO:9).

8. The promoter of claim 1, wherein the spacer comprises the sequence TTTTGCGGGCTTTCAG (SEQ ID NO:10).

9. A nucleic acid construct comprising the promoter from claim 1 operably linked to a polynucleotide encoding a gene product of interest.

10. A *Neisseria meningitides* bacterium comprising the promoter from claim 1, or the nucleic acid construct of claim 9.

11. The *Neisseria meningitidis* bacterium of claim 10, wherein the promoter is operably positioned in the genome of the bacterium to facilitate expression of an endogenous polynucleotide or a recombinant polynucleotide.

12. The *Neisseria meningitidis* bacterium of claim 11, wherein the endogenous polynucleotide encodes a *Neisseria meningitidis* surface antigen.

13. A method of expressing a *Neisseria meningitidis* surface antigen, the method comprising:

culturing the *Neisseria meningitidis* bacterium of claim 10, wherein said culturing facilitates expression of the surface antigen.

14. A method of expressing a *Neisseria meningitidis* surface antigen, the method comprising:

operably inserting a promoter sequence from claim 1 into the genome of a *Neisseria meningitides* host upstream of a native surface antigen gene; and culturing the *Neisseria meningitidis* host, wherein said culturing facilitates expression of the surface antigen.

15. A method of expressing a *Neisseria meningitidis* surface antigen, the method comprising:

inserting a nucleic acid construct comprising a promoter sequence from claim 1 operably linked to a polynucleotide sequence encoding a surface antigen into the genome of a *Neisseria meningitides* host; and culturing the *Neisseria meningitidis* host, wherein said culturing facilitates expression of the surface antigen.

16. A method of expressing a *Neisseria meningitidis* surface antigen, the method comprising:

operably inserting a first promoter sequence upstream of a native surface antigen gene in the genome of a *Neisseria meningitidis* host;

inserting a nucleic acid construct comprising a second promoter sequence operably linked to a polynucleotide sequence encoding a surface antigen into the genome of the *Neisseria meningitidis* host; and culturing the *Neisseria meningitidis* host, wherein said culturing facilitates expression of the surface antigen;

wherein the first and second promoters are each a promoter according to claim 1.

17. The method of claim 16, wherein said first and second promoters are the same.

18. The method of claim 16, wherein said first and second promoters are different.

19. The nucleic acid construct of claim 9, wherein the promoter is operably linked to a first polynucleotide that encodes a gene product of interest, and wherein the first polynucleotide is operably linked to a second polynucleotide that encodes a gene product of interest, such that the promoter drives expression of the first and the second polynucleotides.

20. The nucleic acid construct of claim 19, wherein the first polynucleotide and the second polynucleotide each encode the same gene product of interest.

21. The nucleic acid construct of claim 19, wherein the first polynucleotide and the second polynucleotide each encode different gene products of interest.

22. The nucleic acid construct of claim 20, wherein the gene product of interest is a *Neisseria meningitidis* surface antigen.

23. The nucleic acid construct of claim 21, wherein each of the different gene products of interest are *Neisseria meningitidis* surface antigens.

24. The nucleic acid construct of claim 19, further comprising a transcription terminator that is operably linked to the 3' end of the second polynucleotide sequence.

25. The nucleic acid construct of claim 9, wherein the promoter is operably linked to a first polynucleotide that encodes a gene product of interest, and wherein the first polynucleotide is operably linked to a second polynucleotide that encodes a gene product of interest, and wherein the second polynucleotide is operably linked to a third polynucleotide that encodes a gene product of interest, such that the promoter drives expression of the first, the second, and the third polynucleotides.

26. The nucleic acid construct of claim 25, wherein the first, the second, and the third polynucleotides each encode the same gene product of interest.

27. The nucleic acid construct of claim 26, wherein the gene product of interest is a *Neisseria meningitidis* surface antigen.

28. The nucleic acid construct of claim 25, wherein two of the polynucleotides encode a first gene product of interest, and wherein one of the polynucleotides encodes a second gene product of interest that is different from the first gene product of interest.

29. The nucleic acid construct of claim 28, wherein the first gene product of interest is a *Neisseria meningitidis* surface antigen.

30. The nucleic acid construct of claim 28, wherein the second gene product of interest is a *Neisseria meningitidis* surface antigen.

31. The nucleic acid construct of claim 25, wherein the first, the second, and the third polynucleotides each encode a different gene product of interest.

32. The nucleic acid construct of claim 31, wherein each of the different gene products of interest is a *Neisseria meningitidis* surface antigen.

33. The nucleic acid construct of claim 25, further comprising a transcription terminator that is operably linked to the 3' end of the third polynucleotide.

* * * * *

SEQUENCE LISTING

```
<160> NUMBER OF SEQ ID NOS: 53

<210> SEQ ID NO 1
<211> LENGTH: 19
<212> TYPE: DNA
<213> ORGANISM: Artificial Sequence
<220> FEATURE:
```

```
<223> OTHER INFORMATION: Synthetic Nucleic Acid
<220> FEATURE:
<221> NAME/KEY: misc_feature
<222> LOCATION: (1)..(1)
<223> OTHER INFORMATION: W at this location can be present or absent
<220> FEATURE:
<221> NAME/KEY: misc_feature
<222> LOCATION: (11)..(11)
<223> OTHER INFORMATION: M at this location can be present or absent
<220> FEATURE:
<221> NAME/KEY: misc_feature
<222> LOCATION: (17)..(17)
<223> OTHER INFORMATION: K at this location can be present or absent
<220> FEATURE:
<221> NAME/KEY: misc_feature
<222> LOCATION: (18)..(18)
<223> OTHER INFORMATION: R at this location can be present or absent
<220> FEATURE:
<221> NAME/KEY: misc_feature
<222> LOCATION: (19)..(19)
<223> OTHER INFORMATION: G at this location can be present or absent

<400> SEQUENCE: 1
wwwwkssvkc mtttcakrg                                                 19

<210> SEQ ID NO 2
<211> LENGTH: 6
<212> TYPE: DNA
<213> ORGANISM: Artificial sequence
<220> FEATURE:
<223> OTHER INFORMATION: Synthetic Nucleic Acid

<400> SEQUENCE: 2 atggtt                                                                6

<210> SEQ ID NO 3
<211> LENGTH: 6
<212> TYPE: DNA
<213> ORGANISM: Artificial sequence
<220> FEATURE:
<223> OTHER INFORMATION: Synthetic Nucleic Acid

<400> SEQUENCE: 3 tataat                                                                6

<210> SEQ ID NO 4
<211> LENGTH: 17
<212> TYPE: DNA
<213> ORGANISM: Artificial sequence
<220> FEATURE:
<223> OTHER INFORMATION: Synthetic Nucleic Acid

<400> SEQUENCE: 4
atatgcctcc tttcata                                                   17

<210> SEQ ID NO 5
<211> LENGTH: 18
<212> TYPE: DNA
<213> ORGANISM: Artificial sequence
<220> FEATURE:
<223> OTHER INFORMATION: Synthetic Nucleic Acid

<400> SEQUENCE: 5
tatatgcctc ctttcata                                                  18

<210> SEQ ID NO 6
<211> LENGTH: 18
<212> TYPE: DNA
<213> ORGANISM: Artificial sequence
```

```
<220> FEATURE:
<223> OTHER INFORMATION: Synthetic Nucleic Acid

<400> SEQUENCE: 6
ataatgcctc ctttcata                                              18

<210> SEQ ID NO 7
<211> LENGTH: 17
<212> TYPE: DNA
<213> ORGANISM: Artificial sequence
<220> FEATURE:
<223> OTHER INFORMATION: Synthetic Nucleic Acid

<400> SEQUENCE: 7
atatgcatca tttcata                                               17

<210> SEQ ID NO 8
<211> LENGTH: 17
<212> TYPE: DNA
<213> ORGANISM: Artificial sequence
<220> FEATURE:
<223> OTHER INFORMATION: Synthetic Nucleic Acid

<400> SEQUENCE: 8
ttttgcgggc tttcata                                               17

<210> SEQ ID NO 9
<211> LENGTH: 18
<212> TYPE: DNA
<213> ORGANISM: Artificial sequence
<220> FEATURE:
<223> OTHER INFORMATION: Synthetic Nucleic Acid

<400> SEQUENCE: 9
ttttgcgggc tttcaggg                                              18

<210> SEQ ID NO 10
<211> LENGTH: 16
<212> TYPE: DNA
<213> ORGANISM: Artificial sequence
<220> FEATURE:
<223> OTHER INFORMATION: Synthetic Nucleic Acid

<400> SEQUENCE: 10
ttttgcgggc tttcag                                                16

<210> SEQ ID NO 11
<211> LENGTH: 197
<212> TYPE: DNA
<213> ORGANISM: Neisseria meningitidis

<400> SEQUENCE: 11
taacagatat taatgccgaa ctacctaact gcaagaatta aataaataaa taaataaata     60
aataaataat aaattgcgac aatgtattgt atatatgcct cctttcatat atactttaat    120
atgtaaacaa acttggtggg gataaaatac ttacaaaaga tttccgcccc atttttatc    180 cactcacaaa ggtaatg                                                  197

<210> SEQ ID NO 12
<211> LENGTH: 177
<212> TYPE: DNA
<213> ORGANISM: Neisseria meningitidis

<400> SEQUENCE: 12
```

```
aataagctat tgttttatat caaaatataa tcattttaa aataaaggtt gcggcattta      60
tcagatattg ttctgaaaaa tggttttttg cggggggggg ggtataattg aagacgtatc    120
gggtgtttgc ccgatgtttt taggttttta tcaaatttac aaaaggaagc ccatatg      177
```

<210> SEQ ID NO 13
<211> LENGTH: 45
<212> TYPE: DNA
<213> ORGANISM: Neisseria meningitidis

<400> SEQUENCE: 13

```
gacaatgtat tgtatatatg cctcctttca tatatacttt aatat                    45
```

<210> SEQ ID NO 14
<211> LENGTH: 45
<212> TYPE: DNA
<213> ORGANISM: Neisseria meningitidis

<400> SEQUENCE: 14

```
ttctgaaaaa tggttttttg cggggggggg ggtataattg aagac                    45
```

<210> SEQ ID NO 15
<211> LENGTH: 17
<212> TYPE: DNA
<213> ORGANISM: Artificial sequence
<220> FEATURE:
<223> OTHER INFORMATION: Synthetic Nucleic Acid

<400> SEQUENCE: 15

```
ttttgcgggg ggggggg                                                   17
```

<210> SEQ ID NO 16
<211> LENGTH: 17
<212> TYPE: DNA
<213> ORGANISM: Artificial sequence
<220> FEATURE:
<223> OTHER INFORMATION: Synthetic Nucleic Acid

<400> SEQUENCE: 16

```
atatgcctcc tttcata                                                   17
```

<210> SEQ ID NO 17
<211> LENGTH: 17
<212> TYPE: DNA
<213> ORGANISM: Artificial sequence
<220> FEATURE:
<223> OTHER INFORMATION: Synthetic Nucleic Acid

<400> SEQUENCE: 17

```
ttttgcgggc tttcata                                                   17
```

<210> SEQ ID NO 18
<211> LENGTH: 18
<212> TYPE: DNA
<213> ORGANISM: Artificial sequence
<220> FEATURE:
<223> OTHER INFORMATION: Synthetic Nucleic Acid

<400> SEQUENCE: 18

```
ttttgcgggc tttcaggg                                                  18
```

<210> SEQ ID NO 19
<211> LENGTH: 16
<212> TYPE: DNA
<213> ORGANISM: Artificial sequence

```
<220> FEATURE:
<223> OTHER INFORMATION: Synthetic Nucleic Acid

<400> SEQUENCE: 19
ttttgcgggc tttcag                                                      16

<210> SEQ ID NO 20
<211> LENGTH: 40
<212> TYPE: DNA
<213> ORGANISM: Neisseria meningitidis

<400> SEQUENCE: 20
aatggttttt tgcggggggg ggggtataat tgaagacgta                             40

<210> SEQ ID NO 21
<211> LENGTH: 40
<212> TYPE: DNA
<213> ORGANISM: Neisseria meningitidis

<400> SEQUENCE: 21
aatggttata tgcctccttt catatataat tgaagacgta                             40

<210> SEQ ID NO 22
<211> LENGTH: 41
<212> TYPE: DNA
<213> ORGANISM: Artificial Sequence
<220> FEATURE:
<223> OTHER INFORMATION: Synthetic Nucleic Acid

<400> SEQUENCE: 22
aatggtttat atgcctcctt tcatatataa ttgaagacgt a                           41

<210> SEQ ID NO 23
<211> LENGTH: 41
<212> TYPE: DNA
<213> ORGANISM: Artificial Sequence
<220> FEATURE:
<223> OTHER INFORMATION: Synthetic Nucleic Acid

<400> SEQUENCE: 23
aatggttata atgcctcctt tcatatataa ttgaagacgt a                           41

<210> SEQ ID NO 24
<211> LENGTH: 40
<212> TYPE: DNA
<213> ORGANISM: Artificial Sequence
<220> FEATURE:
<223> OTHER INFORMATION: Synthetic Nucleic Acid

<400> SEQUENCE: 24
aatggttata tgcatcattt catatataat tgaagacgta                             40

<210> SEQ ID NO 25
<211> LENGTH: 40
<212> TYPE: DNA
<213> ORGANISM: Artificial Sequence
<220> FEATURE:
<223> OTHER INFORMATION: Synthetic Nucleic Acid

<400> SEQUENCE: 25
aatggttttt tgcgggcttt catatataat tgaagacgta                             40

<210> SEQ ID NO 26
<211> LENGTH: 41
<212> TYPE: DNA
```

<213> ORGANISM: Artificial Sequence
<220> FEATURE:
<223> OTHER INFORMATION: Synthetic Nucleic Acid

<400> SEQUENCE: 26
aatggttttt tgcgggcttt cagggtataa ttgaagacgt a 41

<210> SEQ ID NO 27
<211> LENGTH: 39
<212> TYPE: DNA
<213> ORGANISM: Artificial Sequence
<220> FEATURE:
<223> OTHER INFORMATION: Synthetic Nucleic Acid

<400> SEQUENCE: 27
aatggttttt tgcgggcttt cagtataatt gaagacgta 39

<210> SEQ ID NO 28
<211> LENGTH: 858
<212> TYPE: DNA
<213> ORGANISM: Artificial Sequence
<220> FEATURE:
<223> OTHER INFORMATION: Synthetic Nucleic Acid

<400> SEQUENCE: 28
atgacccgct ccaaacccgt aaatcgcacc accttcttct gcttgtcgct gaccgccgca 60
ctgatcttga ccgcctgctc ctccggcggc ggtggcagcg gtggcggtgg cgtggcagca 120
gatatcggtg caggcttggc ggacgcactg accgcaccgt tggatcacaa agacaaaggc 180
ctgcaatcct tgacgctgga tcagagcgtc tccaaaaacg aaaaattgaa actggcagcc 240
caaggcgccg aaaaaaccta tggtaacggc gacagcctga atacgggcaa attgaaaaat 300
gataaagtct cccgctttga cttcatccgc caaattgaag ttgatggcca gttgattacc 360
ctggaaagcg gcgaatttca agtttacaaa cagtcgcaca gcgccttgac cgcgctgcaa 420
acggaacaag tgcaggattc ggaagacagc ggcaaaatgg tagccaaacg ccagtttcgc 480
atcggtgata ttgcgggcga acatacctcc ttcgacaaat tgcccaaagg tggctcggcg 540
acctatcgcg gtacggcatt tggctcggat gacgccggtg gcaaactgac ctacacgatc 600
gacttcgccg tgaaacaagg tcacggcaaa attgaacatt tgaaatcccc ggaactgaac 660
gtagatttgg cggcagccta tatcaaaccc gacaaaaaac gccatgccgt catttccggc 720
tcggttctgt ataatcagga tgaaaaaggt agctactcct tgggcatctt cggtggccaa 780
gcacaggaag tggccggctc ggcggaagtt gaaacggcga acggtatcca tcacatcggc 840
ttggcagcaa aacagtaa 858

<210> SEQ ID NO 29
<211> LENGTH: 858
<212> TYPE: DNA
<213> ORGANISM: Neisseria meningitidis

<400> SEQUENCE: 29
atgactagga gcaaacctgt gaaccgaact accttttttct gcctttctct gaccgccgcc 60
ctgattctga ccgcctgcag tagcggaggc ggcggaagcg gaggcggcgg tgtcgccgcc 120
gacatcggtg cggggcttgc tgatgcacta accgcaccgc tcgaccataa agacaaaggt 180
ttgcagtctt tgacgctgga tcagtccgtc agcaaaaacg agaaactgaa gctggcggca 240
caaggtgcgg aaaaaactta tggaaacggc gacagcctca atacgggcaa attgaagaac 300
gacaaggtca gccgcttcga ctttatccgt caaatcgaag tggacgggca gctcattacc 360

```
ttggagagcg gagagttcca agtgtacaaa caaagccatt ccgccttaac cgcccttcag    420
actgagcaag tacaagactc ggaggattcc gggaagatgg ttgcgaaacg ccagttcaga    480
atcggcgaca tagcgggcga acatacgtct tttgacaagc ttcccaaagg cggcagtgcg    540
acatatcgcg ggacggcgtt cggttcagac gatgctggcg aaaactgac ctatactata    600 gatttcgccg tcaaacaggg acacggcaaa atcgaacatt tgaaatcgcc cgaactcaat    660
gtcgacctgg ccgccgccta tcaagccg ataaaaaac gccatgccgt catcagcggt      720
tccgtccttt acaaccaaga cgagaaaggc agttactccc tcggcatctt tggcgggcaa    780
gcccaggaag ttgccggcag cgcggaagtg gaaaccgcaa acggcataca ccatatcggt    840
cttgccgcca agcagtaa                                                  858
```

<210> SEQ ID NO 30
<211> LENGTH: 840
<212> TYPE: DNA
<213> ORGANISM: Artificial Sequence
<220> FEATURE:
<223> OTHER INFORMATION: Synthetic Nucleic Acid

<400> SEQUENCE: 30

```
atgaccggct ccaaacccgt gaaccgcacc gcattctgct gcttttcgtt gaccgccgca    60
ctgattctga ccgcctgctc gtcgggcggc ggtggcgtgg cagcagatat cggtgcaggc    120
ttggcggacg cactgaccgc accgttggat cataaagaca aaggcctgca atccttgacg    180
ctggatcagt cggtacgcaa aaacgaaaaa ttgaaactgg cagcccaagg cgccgaaaaa    240
acctatggta acggcgactc cctgaatacg ggcaaattga aaaatgataa agtgtcgcgc    300
tttgacttca tccgccaaat tgaagtagat ggccagttga tcaccctgga atcgggcgaa    360
tttcaaattt acaaacagga ccacagcgca gtcgttgccc tgcaaatcga aaaaatcaac    420
aacccggata aaatcgacag cttgattaac cagcgctcgt ttctggttag cggcttgggt    480
ggcgaacaca ccgccttcaa tcaactgccg agcggtaaag ccgaatatca tggcaaagcg    540
tttagctccg atgaccccaa cggccgcctg cactattcca tcgatttcac caaaaaacaa    600
ggttacggcc gcattgaaca tttgaaaacg cccgaacaga atgtcgaact ggccagcgcg    660
gaattgaaag cagatgaaaa atcccatgcg gttatcttgg gcgacacccg ctatggtggc    720
gaagaaaaag gcacgtacca cttggcactg ttcggtgacc gcgcacagga aattgcaggc    780
tcggcgacgg taaaaatccg cgaaaaagtt cacgaaatcg gtattgcagg taaacagtaa    840
```

<210> SEQ ID NO 31
<211> LENGTH: 843
<212> TYPE: DNA
<213> ORGANISM: Artificial Sequence
<220> FEATURE:
<223> OTHER INFORMATION: Synthetic Nucleic Acid

<400> SEQUENCE: 31

```
atgacccgct cgaaacccgt gaaccgcacc gcattctgct gcttgtcgtt gaccgccgcc    60
ctgattttga ccgcctgctc gtccggcggc ggtggcgtgg cagcagatat cggtgcaggc    120
ttggcagacg ccctgaccgc accgttggat cacaaagaca atcgctgca aagcttgacg    180 ctggatcaga gcgtatccaa aaacgaaaaa ttgaaactgg cagcccaagg cgccgaaaaa    240
acctatggta acggcgacag cctgaatacg ggcaaattga aaaatgataa agtctcccgc    300
tttgacttca tccgccaaat tgaagttgat ggccagttga ttaccctgga aagcggcgaa    360
```

| | |
|---|---|
| tttcaagtct acaaacagtc gcacagcgcg ttgaccgcac tgcaaacgga acaagtgcag | 420 |
| gactccgaac attcgggcaa aatggtagcg aaacgccagt ttcgcatcgg tgatattgcc | 480 |
| ggcgaacaca ccagcttcga caaattgccc gaaggtggcc gcgcaaccta tcgcggtacg | 540 |
| gcatttggca gcgatgacgc gtccggcaaa ctgacctaca cgatcgattt cgcggcaaaa | 600 |
| caaggtcacg gcaaaattga acatttgaaa tcgccggaac tgaacgtgga cttggccgcg | 660 |
| tccgatatca aacccgacaa aaacgccat gcggtcattt ccggctcggt tctgtataat | 720 |
| caggccgaaa aaggtagcta ctccttgggc atcttcggtg gccaagccca ggaagttgcg | 780 |
| ggctcggcag aagtagaaac cgcaaatggt atccgccaca tcggcttggc agcaaaacaa | 840 |
| taa | 843 |

```
<210> SEQ ID NO 32
<211> LENGTH: 753
<212> TYPE: DNA
<213> ORGANISM: Artificial Sequence
<220> FEATURE:
<223> OTHER INFORMATION: Synthetic Nucleic Acid

<400> SEQUENCE: 32
```

| | |
|---|---|
| ggcgtagcag ctgacatcgg taccggcctg gcggacgctc tgaccgcccc gttggaccat | 60 |
| aaagacaaag gcctgaaaag cctgaccttg gaagacagca ttccgcaaaa cggtacactc | 120 |
| acgctgagcg ctcaaggcgc cgaaaaaacc ttcaaagcgg cgacaaaga taactctctg | 180 |
| aacaccggca aactgaaaaa tgacaaaatt tctcgcttcg acttcgtaca aaaaatcgaa | 240 |
| gtcgacggtc aaacaatcac attggcaagc ggcgaattcc aaatttataa acaaaaccac | 300 |
| tcagccgttg tcgccctgca aattgagaaa attaacaacc ctgacaaaac ggactccctg | 360 |
| atcaaccaac gttccttctt ggtgtctggc ctgggcggtg aacataccgc gttcaatcaa | 420 |
| ctacctggtg gtaaagcgga atatcacggt aaagctttct cttccgacga ccccaacggc | 480 |
| cgtttgcact actccatcga tttcaccaaa aaacaggggtt atggtcgcat tgaacacctg | 540 |
| aaaacccctgg agcaaaatgt agaattggcc gctgccgaac tgaaggctga cgaaaaatct | 600 |
| cacgccgtta tcctgggtga tacccgctac ggttctgaag aaaaaggcac ttaccacctg | 660 |
| gccctgtttg gcgaccgtgc gcaagaaatt gccggcagcg ccaccgtcaa aatcggtgaa | 720 |
| aaagtccacg aaatcggcat tgcgggcaag caa | 753 |

```
<210> SEQ ID NO 33
<211> LENGTH: 747
<212> TYPE: DNA
<213> ORGANISM: Artificial Sequence
<220> FEATURE:
<223> OTHER INFORMATION: Synthetic Nucleic Acid

<400> SEQUENCE: 33
```

| | |
|---|---|
| ggtgttgcgg ccgacatcgg cgccgggctg gccgacgcgc tgacggcgcc tctggaccac | 60 |
| aaagacaaag gcttgcagtc tttgactctg gaccaatctg tacgcaagaa cgaaaaactc | 120 |
| aaactggccg ctcaaggtgc ggaaaagacc tacggcaacg gcgacagcct gaacactggc | 180 |
| aaactgaaaa acgacaaagt gtctcgcttt gacttcatcc gtcaaattga agtcgacggc | 240 |
| cagttgatta ccttagaatc cggcgaattc caagtttaca acagtctca cagcgccttg | 300 |
| acggcgttcc agactgaaca aatccaagat agcgaacact ctggcaaaat ggttgccaaa | 360 |
| cgccagtttc gcatcggcga catcgcaggt gaacacacta gcttcgataa actgccggaa | 420 |
| ggcggccgcg ccacctaccg cggtaccgcg ttcggcagcg acgatgccgg tggcaaattg | 480 |

```
acttatacca ttgattttgc cgcaaaacaa ggcaacggca aaattgaaca cttgaaatct    540
cctgaactga acgtagacct cgcggcagca gacatcaagc cggatggtaa gcgccacgct    600
gtgatcagcg gcagcgtttt gtacaaccaa gcagaaaaag gctcctattc cttaggcatc    660
ttcggcggca aagcacaaga ggtagccggc tcggccgaag taaaaactgt gaacggcatc    720
cgccacatcg gtctggccgc caaacaa                                        747
```

<210> SEQ ID NO 34
<211> LENGTH: 747
<212> TYPE: DNA
<213> ORGANISM: Artificial Sequence
<220> FEATURE:
<223> OTHER INFORMATION: Synthetic Nucleic Acid

<400> SEQUENCE: 34

```
ggggtcgctg cagacattgg cgctggcctg gccgatgcct tgaccgcgcc gctggatcac     60
aaagacaaat ccttgcaaag tttgactctg gaccaatccg tgcgcaaaaa tgaaaaactg    120
aagctggcgg ctcaaggcgc ggagaaaacc tatggcaacg gcgatagcct gaacactggc    180
aaactgaaaa atgacaaagt aagccgtttc gactttatcc gccaaattga agttgacggc    240
caattgatta ccctggaatc cggcgaattc caagtgtaca acaatctca cagcgctttg    300 accgcactcc aaaccgagca agaacaagac cctgaacact cgggtaaaat ggtcgcgaaa    360
cgccgtttta aaatcggcga tatcgccggt gaacacacga gcttcgataa attgccgaag    420
gatgttatgg cgacctaccg cggcactgcc tttggctccg acgacgccgg cggtaaattg    480
acctacacta ttgacttcgc cgccaaacaa ggtcacggca agattgaaca cctgaaaagc    540
ccggaactca acgtggaact ggcaaccgca tacatcaaac cggatgagaa acaccacgcg    600
gttatctctg gcagcgtcct gtacaatcaa gatgaaaaag gctcctactc tttgggtatc    660
ttcggtggtc aagctcaaga gtagcgggc tcggcggaag tggaaaccgc caacggcatt    720
caccacattg gcctggcagc gaaacag                                        747
```

<210> SEQ ID NO 35
<211> LENGTH: 747
<212> TYPE: DNA
<213> ORGANISM: Artificial Sequence
<220> FEATURE:
<223> OTHER INFORMATION: Synthetic Nucleic Acid

<400> SEQUENCE: 35

```
ggcgtcgcgg ccgacattgg cgccggtttg gcggacgcgc tcaccgctcc gttggaccat     60
aaagataaag gcttgcaatc cctgacgttg gatcaaagcg ttcgcaaaaa cgaaaaactg    120
aaattggccg cgcaaggtgc tgaaaaaacc tacggtaacg gtgactcttt gaacaccggt    180
aaattaaaaa acgataaagt cagccgtttc gactttatcc gccaaattga agttgacggt    240
aaattgatta ccctggaaag cggcgaattc caagtctaca acaaagcca cagcgccctg    300 accgctttgc aaacggaaca agttcaagat tccgaagact ccggcaaaat ggttgcaaaa    360
cgccagttcc gtatcgggga tatcgcgggc gaacacacca gcttcgacaa attgcctaaa    420
ggtggttcgg caacctatcg cggtaccgcc ttcggttctg atgacgcggg tgcaaatta    480 acctatacca ttgatttcgc tgccaaacaa ggccatggta aaatcgagca cttgaaatca    540
ccggagctga acgttgaact ggccacggcc tacatcaaac cggacgaaaa acgccacgcc    600
gtaatctccg gttctgtttt gtacaaccaa gatgaaaaag gctcctattc tttgggcatt    660
```

| ttcggcggcc aagcccaaga agtggcgggc tctgcagaag tcgaaaccgc aaacggcatc | 720 |
| cgtcacattg gtctggccgc aaaacag | 747 |

<210> SEQ ID NO 36
<211> LENGTH: 744
<212> TYPE: DNA
<213> ORGANISM: Artificial Sequence
<220> FEATURE:
<223> OTHER INFORMATION: Synthetic Nucleic Acid

<400> SEQUENCE: 36

| ggtgtcgcgg ccgacatcgg tgctggcctg gctgacgccc tgaccgcacc tttggaccac | 60 |
| aaagacaaag gcttgcaatc cctgatgctg gaccaatccg tccggaagaa cgaaaaattg | 120 |
| aagttggcgg cccagggcgc tgaaaaaacc tacggtaatg gtgactccct gaacactggc | 180 |
| aaactgaaaa acgataaagt gtcccgcttt gacttcattc gccaaattga agtggatggt | 240 |
| aaactgatta ccctggaaag cggcgaattc caaatttaca acaagacca tagcgcggtc | 300 |
| gtggcactgc aaatcgaaaa aattaacaac cccgacaaaa tcgattcttt gatcaatcag | 360 |
| cgctccttct tggtcagcgg cttgggcggc gagcacaccg catttaacca attgcctagc | 420 |
| ggcaaagcag aataccacgg taaagcgttt tcctcagacg acgcaggtgg caaattgacc | 480 |
| tacaccattg attttgccgc caaacaaggt catggcaaaa tcgaacacct gaaaactccg | 540 |
| gagcaaaatg tagagctggc atccgccgaa ctgaaagccg acgaaaaatc tcacgcagtg | 600 |
| atcttgggcg acacgcgtta tggcggcgaa gaaaaaggca cctaccacct ggccctgttc | 660 |
| ggtgaccgtg cacaagaaat tgcaggtagc gccactgtga aaatccgcga aaagtacac | 720 |
| gaaattggca ttgcaggtaa acaa | 744 |

<210> SEQ ID NO 37
<211> LENGTH: 744
<212> TYPE: DNA
<213> ORGANISM: Artificial Sequence
<220> FEATURE:
<223> OTHER INFORMATION: Synthetic Nucleic Acid

<400> SEQUENCE: 37

| ggtgtggcgg cggacatcgg cgctggcttg gccgacgcgc tgacggcgcc tctggatcat | 60 |
| aaagataaaa gcctgcaatc tttgacgttg gaccaatctg tccgtaaaaa tgaaaaactg | 120 |
| aagttggccg cgcagggcgc agaaaagact tatggtaacg gtgactcttt aaataccggc | 180 |
| aaactgaaaa acgataaagt ctcccgcttt gatttcatcc gccaaattga ggtcgatggc | 240 |
| caattgatca cgctggagtc tggcgaattc caaatctaca acaagacca ttccgctgtt | 300 |
| gtggctctgc aaatcgaaaa aatcaataac cccgacaaaa tcgactcttt gatcaaccaa | 360 |
| cgtagcttcc tcgtatctgg tctgggcggt gagcacaccg cgttcaacca attgcccagc | 420 |
| ggtaaggccg aataccatgg caaagcgttc tcttctgacg atgcaggtgg taaactgacc | 480 |
| tacaccattg atttcgcagc taaacaaggc catggtaaaa tcgaacatct gaaaccccg | 540 |
| gaacagaatg tagagctggc atctgcagaa ctgaaagccg acgagaaatc acacgccgta | 600 |
| atcctgggcg atacccgcta cggtggtgaa gaaaaaggca cctatcactt ggcactgttc | 660 |
| ggtgaccgtg cacaagaaat cgctggttct gcaaccgtga aaattcgtga aaagtacac | 720 |
| gaaattggca ttgccggaaa acaa | 744 |

<210> SEQ ID NO 38
<211> LENGTH: 747

```
<212> TYPE: DNA
<213> ORGANISM: Artificial Sequence
<220> FEATURE:
<223> OTHER INFORMATION: Synthetic Nucleic Acid

<400> SEQUENCE: 38
ggcgtagccg ctgatatcgg cgccggcctg gcggatgcgt tgacagcacc gctggaccat      60
aaagataaag gtctgcaatc cctgaccttg gatcaaagcg tacgtaaaaa cgaaaaattg     120
aaactagccg cccaaggtgc ggaaaaaacc tacggtaacg gcgattcttt gaacacgggc     180
aaattgaaaa atgacaaagt ctcccgcttt gacttcatcc gccaaattga agttgacgga     240
aaattgatta ccctggaaag cggtgaattc caagtataca aacaaagcca ctctgccttg     300
accgcattgc agaccgaaca agtgcaagac agcgaagata gcggcaaaat ggttgccaaa     360
cgccaattcc gcattggtga catagccggc gaacacacca gtttcgacaa actgcctaaa     420
ggcggttctg ctacttaccg tggcacagcc ttgggctccg acgacgccgg cggtaaattg     480
acctacacta tcgacttcgc cgccaaacaa ggccacggca aaatcgagca cttgaaatca     540
ccggaattga acgtcgaatt ggccaccgcc tacatcaaac cggacgaaaa acgtcatgcc     600
gtgatttctg gctctgtttt gtacaaccaa gacgagaaag gcagctacag cttgggtatt     660
ttcggcggtc aagcccaaga agttgcgggc tccgcagaag tagaaaccgt gaacggcatt     720
caccacattg gcctggctgc aaaacaa                                         747

<210> SEQ ID NO 39
<211> LENGTH: 525
<212> TYPE: DNA
<213> ORGANISM: Artificial Sequence
<220> FEATURE:
<223> OTHER INFORMATION: Synthetic Nucleic Acid

<400> SEQUENCE: 39
atgaaaaaag ccctggccac cctgattgcg ctggcactgc ctgcggcggc actcgccgaa      60
ggcgcaagcg gtttctacgt gcaagccgat gccgcacacg ccaaagcctc gtcctccctg     120
ggttctgcca aaggcttttc tcctcgcatc agcgccggtt accgtatcaa cgatctgagg     180
tttgccgtag actacacgcg ttataaaaac tacaaagcac ccagcactga cttcaaattg     240
tactctatcg gcgcgtctgc tatctatgat ttcgacaccc aatccccggt taaaccttac     300
ttgggagccc gtttgtcctt gaaccgcgca tccgtggacc tgggtggcag cgactccttt     360
tcacaaacca gcatcggtct gggcgtgctg accggtgtaa gctacgctgt cacgcctaac     420
gtagatctgg acgccggtta ccgttacaat tacattggta agttaacac tgtgaaaaat     480
gtacgctccg gcgaactgtc cgcgggcgtc cgcgtaaaat tctga                     525

<210> SEQ ID NO 40
<211> LENGTH: 525
<212> TYPE: DNA
<213> ORGANISM: Artificial Sequence
<220> FEATURE:
<223> OTHER INFORMATION: Synthetic Nucleic Acid

<400> SEQUENCE: 40
atgaaaaaag ccttggccac cttgatcgcc ttggccttgc cggccgccgc cttggccgaa      60
ggcgcctccg gcttctacgt tcaagccgac gccgcccacg ccaaagcctc ctcctccttg     120
ggctccgcca aaggcttctc cccgcgcatc tccgccggct accgcatcaa cgacttgcgc     180
ttcgccgttg actacacccg ctacaaaaac tacaaagccc cgtccaccga cttcaaattg     240
```

| | |
|---|---|
| tactccatcg gcgcctccgc catctacgac ttcgacaccc aatccccggt taaaccgtac | 300 |
| ttgggcgccc gcttgtcctt gaaccgcgcc tccgttgact tgggcggctc cgactccttc | 360 |
| tcccaaacct ccaccggctt gggcgttttg gccggcgttt cctacgccgt taccccgaac | 420 |
| gttgacttgg acgccggcta ccgctacaac tacatcggca agttaacac cgttaaaaac | 480 |
| gttcgctccg gcgaattgtc cgccggcgtt cgcgttaaat tctga | 525 |

<210> SEQ ID NO 41
<211> LENGTH: 1467
<212> TYPE: DNA
<213> ORGANISM: Artificial Sequence
<220> FEATURE:
<223> OTHER INFORMATION: Synthetic Nucleic Acid

<400> SEQUENCE: 41

| | |
|---|---|
| atgtttaagc gttccgttat tgctatggcc tgcattttcg ccttgtccgc ctgcggtggc | 60 |
| ggtggtggcg gcagccccga cgtaaaatct gccgacacct gagcaaacc cgctgcgcct | 120 |
| gttgtatctg aaaagaaac cgaagcgaaa gaagatgctc cgcaggcggg ctcccaaggt | 180 |
| caaggcgcac cttctgccca aggctcacaa gacatggccg cggtgtccga agaaaatacc | 240 |
| ggtaatggtg cgctgttac cgcagacaat ccgaaaaacg aagatgaagt tgctcaaaac | 300 |
| gacatgccac agaacgccgc cggcactgac tcttccaccc ccaaccacac ccctgaccct | 360 |
| aatatgttgg ccggcaacat ggaaaaccaa gccaccgacg caggcgagtc cagccaaccc | 420 |
| gccaaccagc ctgatatggc gaacgcggcc gacggtatgc aaggcgatga cccgagcgca | 480 |
| ggcggtcaaa acgcgggcaa caccgccgcc caaggcgcta accaggctgg taacaaccaa | 540 |
| gccgcaggca gcagcgaccc gatcccggca tcaaacccgg cacctgcaaa cggcggaagc | 600 |
| aacttcggcc gcgttgactt ggcaaacggc gtgctgatcg acggcccgtc tcaaaacatc | 660 |
| accttgaccc attgtaaagg cgactcttgc tccggcaaca atttcctgga cgaggaagtc | 720 |
| cagttgaaat ccgaatttga aaagctgagc gacgcggata aaatttctaa ctataaaaaa | 780 |
| gacggcaaaa acgacaaatt cgtaggcctg gttgccgata gtgtgcagat gaaaggcatc | 840 |
| aaccaataca ttatcttcta taaaccgaaa cctacctcct tcgctcgttt ccgccgtagc | 900 |
| gcccgctccc gccgttcctt gccggccgaa atgcccctga tccccgtaaa ccaagctgac | 960 |
| actttgatcg tagatggcga ggcagttttc tctcaccggcc acagcggcaa tattttcgca | 1020 |
| cccgaaggta actaccgcta cctgacttat ggcgccgaaa aactgccggg tggctcttat | 1080 |
| gcgctgcgcg tccaaggcga gccggcaaaa ggtgaaatgt tggccggcgc tgccgtatat | 1140 |
| aacggcgaag tgttgcactt ccataccgaa aacggtcgcc cgtacccgac ccgcggccga | 1200 |
| tttgctgcta agtcgacttt cggcagcaaa agtgttgacg gtattatcga ctcaggcgac | 1260 |
| gatttgcaca tgggtacgca aaaattcaaa gccgcgatcg acggtaatgg cttcaaaggc | 1320 |
| acctggacgg aaaacggttc tggtgacgtt tctggtaaat tctacggccc cgccggcgaa | 1380 |
| gaggtcgcgg gcaaatattc ataccgccct accgacgccg aaaaggggg ctttggtgtt | 1440 |
| ttcgccggta aaaagaaca agactga | 1467 |

<210> SEQ ID NO 42
<211> LENGTH: 2139
<212> TYPE: DNA
<213> ORGANISM: Artificial Sequence
<220> FEATURE:
<223> OTHER INFORMATION: Synthetic Nucleic Acid

<400> SEQUENCE: 42

```
atgaacaacc cgttggttaa ccaagccgcc atggttttgc cggttttctt gttgtccgcc    60
tgcttgggcg gcggcggctc cttcgacttg gactccgttg acaccgaagc cccgcgcccg   120
gccccgaaat accaagacgt tttctccgaa aaccgcaag cccaaaaaga ccaaggcggc    180
tacggcttcg ccatgcgctt gaaacgccgc aactggtacc cgcaagccaa agaagacgaa   240
gttaaattgg acgaatccga ctgggaagcc accggcttgc cggacgaacc gaaagaattg   300
ccgaaacgcc aaaaatccgt tatcgaaaaa gttgaaaccg actccgacaa caacatctac   360
tcctccccgt acttgaaacc gtccaaccac aaaacggca acaccggcaa cggcatcaac   420
caaccgaaaa accaagccaa agactacgaa aacttcaaat acgtttactc cggctggttc   480
tacaaacacg ccaaacgcga attcaacttg aaagttgaac cgaaatccgc caaaaacggc   540
gacgacggct acatcttcta ccacggcaaa gaaccgtccc gccaattgcc ggcctccggc   600
aaaatcacct acaaaggcgt tggcacttc gccaccgaca ccaaaaaagg ccaaaaattc    660
cgcgaaatca tccaaccgtc caaatcccaa ggcgaccgct actccggctt ctccggcgac   720
gacggcgaag aatactccaa caaaaacaaa tccaccttga ccgacggcca agaaggctac   780
ggcttcacct ccaacttgga agttgacttc acaacaaaa aattgaccgg caaattgatc    840
cgcaacaacg ccaacaccga caacaaccaa gccaccacca cccaatacta ctccttggaa   900
gcccaagtta ccggcaaccg cttcaacggc aaagccaccg ccaccgacaa accgcaacaa   960
aactccgaaa ccaaagaaca cccgttcgtt tccgactcct cctccttgtc cggcggcttc  1020
ttcggcccgc aaggcgaaga attgggcttc cgcttcttgt ccgacgacca aaaagttgcc  1080
gttgttggct ccgccaaaac caaagacaaa ccggccaacg caacaccgc cgccgcctcc   1140
ggcggcaccg acgccgccgc ctccaacggc gccgccggca cctcctccga aaacggcaaa  1200
ttgaccaccg ttttggacgc cgttgaattg aaattgggcg acaaagaagt tcaaaaattg  1260
gacaacttct ccaacgccgc caattggtt gttgacggca tcatgatccc gttgttgccg   1320
gaagcctccg aatccggcaa caaccaagcc aaccaaggca ccaacggcgg caccgccttc  1380
acccgcaaat tcgaccacac cccggaatcc gacaaaaaag acgcccaagc cggcacccaa  1440
accaacggcg cccaaaccgc ctccaacacc gccggcgaca ccaacggcaa aaccaaaacc  1500
tacgaagttg aagtttgctg ctccaacttg aactacttga atacggcat gttgaccgc    1560
aaaaactcca atccgccat gcaagccggc gaatcctcct cccaagccga cgccaaaacc  1620
gaacaagttg aacaatccat gttcttgcaa ggcgaacgca ccgacgaaaa agaaatcccg  1680
tccgaacaaa acatcgttta ccgcggctcc tggtacggct acatcgccaa cgacaaatcc  1740
acctcctggt ccggcaacgc ctccaacgcc acctccggca ccgcgccga ttcaccgtt    1800
aacttcgccg acaaaaaaat caccggcacc ttgaccgccg acaaccgcca agaagccacc  1860
ttcaccatcg acggcaacat caaagacaac ggcttcgaag gcaccgccaa aaccgccgaa  1920
tccggcttcg acttggacca atccaacacc cccgcaccc cgaaagccta catcaccgac  1980
gccaaagttc aaggcggctt ctacggcccg aaagccgaag aattgggcgg ctggttcgcc  2040
tacccgggcg acaaacaaac caaaaacgcc accaacgcct ccggcaactc ctccgccacc  2100
gttgttttcg cgccaaacg ccaacaaccg gttcgctaa                           2139
```

<210> SEQ ID NO 43
<211> LENGTH: 2748
<212> TYPE: DNA
<213> ORGANISM: Artificial Sequence
<220> FEATURE:

<223> OTHER INFORMATION: Synthetic Nucleic Acid

<400> SEQUENCE: 43

```
atgcagcaac aacacctgtt ccgcttcaac attctgtgcc tgagcctgat gactgccctg      60
cctgcgtacg cggagaacgt acaagccggc caagcccaag aaaaacagct ggacaccatc     120
caagtaaaag ccaaaaaaca aaaaactcgc cgcgataacg aggttaccgg tctgggcaaa     180
ttggtgaaat cgtcggacac cttgagcaag gagcaagtat tgaatattcg tgacctgacc     240
cgctacgacc ctggtatcgc cgtcgtagaa cagggccgtg gcgcaagctc aggttattcc     300
attcgtggta tggacaaaaa tcgcgtaagc ctgaccgttg acggcgtctc ccagatccag     360
tcttacacag cccaagccgc tctgggcggt acccgcaccg ccggcagctc aggcgccatt     420
aacgaaatcg aatacgaaaa tgttaaagca gttgaaatta gcaaaggctc caactccgtt     480
gagcaaggct ccggcgcctt ggccggcagc gtagcctttc aaactaaaac cgctgatgac     540
gtgattggcg aaggtcgtca atggggcatc caatcgaaaa ccgcttacag cggcaaaaac     600
cgcggcttga cccaatctat cgcattggcg gtcgtattg gcgtgccga ggcactgctg       660
atccacaccg tcgtcgcgc aggcgaaatc cgcgcccacg aagatgccgg caggggtgtt     720
cagtcccttta accgcttggt tcccgtgaaa gattcatcga actacgcata cttcatcgtg     780
aaagaagaat gcaaaaacgg tagctacgaa acgtgcaaag ctaaccctaa aaaggacgtt     840
gttggcaagg acgaacgcca aactgttagc actcgtgatt acaccggtcc caaccgcttt     900
ctggcagacc cgctgtcata tgaatcccgc tcctggctct ccgcccgggg tttccgcttc     960
gagaacaaac gacactatat tggggggcatc ttggaacaca ctcaacaaac cttcgacacc    1020
cgtgatatga cagtacccgc cttcttgacc aaagctgtct tcgatgcgaa caaaaaacaa    1080
gcgggttctc tacctggcaa tggtaaatac gccggcaatc acaaatacgg cggtctgttt    1140
accaacggtg aaaacggtgc attggtcggc gccgaatacg gcacgggcgt cttttacgac    1200
gagacccata cgaaaagtcg ctacggcttg gagtatgttt atacaaacgc cgacaaagac    1260
acgtgggccg actacgcccg cttgtcttac gaccgtcagg gtattggcct ggacaaccac    1320
tttcaacaaa ctcactgctc cgcggacggg agcgacaaat attgccgccc ttctgcggac    1380
aaaccgttct cctactacaa atccgatcgc gtgatctatg gcgaaagtca tcgactgtta    1440
caggccgcgt tcaaaaaaag cttcgacacc gccaaaattc gtcacaatct gtcggtcaat    1500
ttgggcttcg accgcttcgg tagcaacctg cgtcaccaag attactatta ccaacatgct    1560
aatcgcgcct actcaagtaa cacccccccct caaaacaacg gcaaaaaaat ctcacccaac    1620
ggctccgaaa cttccccctta ctgggtgacc attggtcgtg gcaacgtagt tactggccaa    1680
atttgccgtc tgggtaacaa tacctatacc gattgcactc cgcgctcaat caacggcaaa    1740
agctactacg cagccgttcg cgacaacgtc cgcctcggcc gttgggcaga cgtcggcgct    1800
ggtctgcgct acgactaccg ctctactcac agccgacgacg gcagtgtgag tactggtact    1860
caccgtacct tgtcctggaa tgccggcatc gtcctcaaac ctaccgactg gctggatttg    1920
acctaccgta catccaccgg ctttcgtttg ccttcattcg cggagatgta cggttggcgt    1980
gcaggcgtac aaagcaaagc tgtgaaaatt gatccggaaa atccttcaa taaagaagct    2040
ggcatcgtat tcaaaggcga cttcggcaac ctggaagcat cctggttcaa caacgcctat    2100
cgtgacctga ttgtgcgtgg ctatgaagcc caaattaaag acggcaaaga agaagcgaaa    2160
ggcgacccgg cttacctgaa cgcgcaatct gcgcgcatca ccggcatcaa tatcctgggc    2220
aaaatcgact ggaacggcgt gtgggataaa ctgcccgaag gctggtactc cactttcgct    2280
```

```
tataaccgcg tgcgtgtccg cgatatcaaa aaacgtgctg accgcacaga tatccaatct   2340
cacttattcg atgcaattca accttcccgc tatgtcgttg cttgggtta tgaccaacct    2400 gaaggtaaat ggggcgtgaa tggcatgttg acttactcca aagccaaaga gattaccgaa   2460
ctgttgggct ctcgtgcgtt gttgaacggc aacagccgta acactaaagc aaccgcgcgt   2520
cgcacgcgcc cttggtatat tgtcgatgta tcaggttact ataccgttaa aaaacacttc   2580
accctgcgcg ccggcgttta caatttgttg aactatcgtt atgtcacctg ggaaaatgta   2640
cgtcaaaccg ctggaggcgc cgttaaccaa cataaaaacg tgggcgttta caaccgttac   2700
gcggcgccag gtcgtaacta caccttcagc ttggaaatga aattctaa                2748

<210> SEQ ID NO 44
<211> LENGTH: 2214
<212> TYPE: DNA
<213> ORGANISM: Artificial Sequence
<220> FEATURE:
<223> OTHER INFORMATION: Synthetic Nucleic Acid

<400> SEQUENCE: 44
atgtgcaaac ccaattacgg tggtatcgtg ttgttgccct tgctgctggc ttcctgtatt      60
ggcggcaact ttggcgtaca accggtagtt gaaagcaccc ctactgcgta cccagtgacc     120
ttcaaatcta aagacgttcc gaccccgccg ccggccggtt ccagcgtgga acaaccccca     180
gttaaccgcc cggcagtagg cgccgctatg cgtctcccgc gccgcaatat cgctagctac     240
aaacaggacg gcactgaaat ccctgacaaa caccaagcag aagaacacct gcctctgaaa     300
gaaaaagaca tcctgttcct ggacggcacc ctgaagaac aagcagacaa attgaaaaag     360
aaaatcaacg aacgctatag cgatgttcgc gttattacct ccaaaaaaga agaagagaaa     420
taccaatacc aattcgtacg cgcgggttac gtgttcacgc gcgccgaagg caaagacaac     480
gaaaaagaaa aaacctctga tggcaaagaa ttcgtcaacc gcttctccta cgacggtttc     540
gtttattact ctggcgaacg cccttcccaa tcgttgcctt ccgcaggcac cgtgcaatat     600
agcggcaact ggcaatatat gaccgacgca aaacgccacc gcactggcaa agcagtctca     660
agcactgact gggctacac cacgtactac ggtaacgaaa tcggtgccac ctcctacgaa     720
gctcgcgacg cggacgaccg cgaaaaaac cctgctgaat atactgtcga cttcgacaat     780
aaaaccctga cggcaaact gatcaaaaac cagtacgttc aaaacaaaag caaccccaac     840
gaaccgaaaa aaccgttgac catctacgac atcactgcca ccctggatgg taaccgcttc     900
accggctccg caaaggtatc caccgaagtg aaaacccaac acgctgataa agaatacctg     960
tttttccaca ccgatgccga ccaacgcttg aaggcggct tcttcggcga acggcgaa    1020 gaattggccg acgcttcat ttcgaacgat aactctgtgt ttggcgtttt cgctggcaaa    1080
caaaaaactg aaaccgaaaa tgcggctgac acaaaccgg ccctctcaag cggcaaacac   1140
actaaaatcc tggactctct gaaaattcc gttgacgaag ctagcgacaa aaacccgcgc    1200
gaattcgcta tctcgagtat gcccgacttt ggtcacccgg acaaactgtt ggtcgaaggt    1260
cgcgaaatcc ctctggtgaa caagaacaa accatcgagc tggcagacgg ccgcaaaact    1320
actattcgca cgtgctgtga cttcctcact tacgtcaaaa ttggccgtat gcaaactgag    1380
cgcccggccg caaaacctaa agcccaggat gaagaacgtg atgaggaaga caccggtgtg    1440
gactcagttg aagagggcga agatgagatc gatgacgaag aaggtaccga agacgcagcc    1500
gtgaaagacg aaggctccga agaagatgag gctgtggaag gtgaggacga agctgaagaa    1560
```

```
ccagaagaag agtctcctac tgaagaaggc ggttccggta gcgacggcat cttgccggcc   1620
cctgaagccc cgaaaggtcg taatattgac ttgttcttga aaggcattcg cacggcggaa   1680
accgatattc cgaaaaccgg cgaagctcac tacaccggta cctgggaagc ccgcatcggc   1740
aaaccgatcc aatgggacaa ccaagccgac aaagaagctg ctaaagctgt gtttaccgtt   1800
gacttcggca aaaaatccat ttctggtacc ttgaccgaag agaacggcgt cgaacccgcg   1860
ttccacattg aaaacggcaa aatcgaaggc aacggttttt atgcgaccgc ccgtactcgc   1920
gagaatggca ttaatttgtc tggcaacggc tccacagatc cgaaaacctt tcaagcctcg   1980
aacttgcgcg tagaaggcgg cttctacggc ccacaagcag aagagctggg tggtatcatc   2040
ttcaacaacg acggcaaaag cctgggcatt accgagggca ctgaaaacaa agtggacgta   2100
gaagctgaag ttgatgctga agttgatgtc ggcaagcaat ggagagcga agtaaaacac   2160 cagtttggtg tcgtcttcgg tgccaaaaaa gacatgcagg aagtcgagaa atga         2214
```

<210> SEQ ID NO 45
<211> LENGTH: 2832
<212> TYPE: DNA
<213> ORGANISM: Artificial Sequence
<220> FEATURE:
<223> OTHER INFORMATION: Synthetic Nucleic Acid

<400> SEQUENCE: 45

```
atgaacaaaa aacacggctt tccgttgact cttaccgcct ggctatcgc caccgccttt     60 ccggcttacg ctgctcaagc cggcggcgcc actcctgacg cagcgcaaac ccagtctctg    120
aaagaaatta ccgtacgtgc tgctaaagta ggtcgccgca gcaaagaagc taccggcttg    180
ggcaaaatcg ttaaaacctc cgaaaccctc aacaaagaac aagttctggg cattcgcgac    240
ctgactcgct acgatcctgg tgttgccgta gtcgaacaag gtaatggcgc ctcgggcggt    300
tatagcatcc gtggcgtaga taaaaaccgt gtcgcagtta gcgttgatgg tgttgcccaa    360
atccaagcat ttaccgtgca aggttccttg tccggctacg gtggtcgcgg cggttccggc    420
gccatcaatg aaatcgaata cgaaaacata tccactgtag agattgataa aggtgcaggt    480
tccagcgatc acggttctgg cgcactgggt ggcgctgttg cattccgcac aaaagaagcc    540
gccgacttga ttagcgacgg caaaagctgg ggtattcaag ccaaaactgc ctacggctct    600
aagaaccgtc aattcatgaa aagcttgggt gctggctttt ccaaagatgg ttgggaaggt    660
ctgctgatcc gcactgaacg tcaaggtagg gaaacccgtc cgcacggtga cattgctgat    720
ggcgttgaat acggcattga ccgtctggac gccttccgcc aaacctacga tatcaaacgc    780
aaaaccagag agcccttctt ttctgtcgaa ggtgagcgcg aatcaaaacc tgtcgccaaa    840
ctggcaggct acggtaaata cctgaacaat caattgaacc gttgggttaa gaacgtatt     900 gaacaaaatc agccctgtc tgcagaagaa gaggctcaag tccgcgaagc acaagctcgt    960
cacgaaaact tgagcgcaca agcctacacc ggcggcggac gcattttgcc tgaccctatg   1020
gattatcgct ccgcagctg gttggccaag ctcggctacc gttttggtgg ccgccactac   1080
gttggtggtg ttttcgaaga cacgaagcaa cgttatgata tccgcgacat gactgaaaaa   1140
caatactatg gcaccgatga agccgagaaa tttcgtgata atccggcgt atatgacggc   1200 gatgatttcc gtgacggttt gtacttcgtt ccgaacatcg aagaatggaa aggcgataaa   1260
aatttggtgc gtggcattgg tttgaaatat tctcgcacca aattcattga tgaacaccac   1320
cgtcgtcgtc gtatgggtct gctgtatcgc tacgaaaatg aagcctactc cgacaattgg   1380
gcggataaag ccgttttgtc cttcgataag cagggtgttg ctaccgataa caatacctc    1440
```

```
aaactgaact gcgctgttta ccccgctgtg gataaatctt gccgtgcctc agccgacaaa      1500
ccatactctt acgactccag cgatcgcttc cactaccgcg aacaacacaa cgttttgaac      1560
gcgtctttcg aaaaatcttt gaaaaacaaa tggactaaac atcacttgac cctgggtttt      1620
ggttacgacg catctaaagc tatcagccgt ccggaacaat tgagccataa cgccgccgg       1680 atttccgaaa gcaccggttt cgatgaaaat aaccaggaca atacttgtt gggcaagcct       1740 gaggtcgtgg aaggctcagt ctgcggctac attgaaacct gcgctctcg taaatgtgtt       1800 cctcgcaaaa tcaatggttc taacatccac atcagcttga cgatcgttt ctccatcggc       1860 aaatactttg acttcagcct gggcggccgt tacgaccgca aaaacttcac tacgtccgag      1920
gagctggtac gttccggccg ctatgttgac cgtagctgga attcaggcat tttgttcaaa      1980
ccgaatcgcc acttcagcgt tagctaccgc gcgtcgtccg gctttcgcac cccgagcttc      2040
caagaactct tcggtattga tatttaccac gactacccta aaggctggca acgcccggcg      2100
ttgaaatccg aaaagcagc taatcgcgaa atcggcttgc aatggaaagg cgacttcggt       2160
ttcctggaaa tctcctcttt ccgcaaccgt tacacggata tgatcgcagt cgcagaccac      2220
aaaaccaaac tgccgaacca agccggccaa ctgaccgaaa ttgatatccg cgactactat      2280
aacgcacaaa acatgtcatt gcaaggtgtt aatatcctgg gcaaaatcga ctggaatggc      2340
gtctatggca aattgccgga aggcctctat acgaccctgg cttataaccg catcaaaccg      2400
aaaagcgtgt ccaaccgccc tgggttgtcc ctgcgctcct acgcactgga cgccgtacaa      2460
ccatcgcgct acgtactggg cttcggctac gaccaacccg aaggcaaatg gggagcgaac      2520
atcatgttga cttacagtaa gggtaaaaac ccagacgaat tggcttatct ggcgggcgac      2580
caaaaacgct attccaccaa gcgcgccagc agcagctgga gcacagccga cgtgtcagca      2640
tacttgaacc tgaaaaaacg cttgaccttg cgcgctgcca tttataacat cggtaattat      2700
cgctatgtga cctgggaaag cctgcgccaa accgctgaaa gcaccgctaa ccgccacggc      2760
ggcgatagca attacggtcg ttatgctgcc cctggtcgta atttctccct ggcactggaa      2820
atgaaattct aa                                                          2832
```

<210> SEQ ID NO 46
<211> LENGTH: 819
<212> TYPE: DNA
<213> ORGANISM: Artificial Sequence
<220> FEATURE:
<223> OTHER INFORMATION: Synthetic Nucleic Acid

<400> SEQUENCE: 46

```
atgaaaaaga ccgttttac ctgtgccatg attgcactga ccggtaccgc tgcggccgcc        60
caggaattgc aaaccgcgaa cgaattcacc gttcatactg acctctcttc tatttcctcc      120
actcgtgcct tcttgaaaga aaaacacaaa gcagccaaac acatctctgt acgcgccgac      180
attcctttcg atgccaatca aggtattcgc ctggaagccg ttttggtcg ctccaaaaaa       240 aacattatca atctggaaac cgacgaaaac aagctgggca aaactaaaaa cgtaaaactg      300
cccaccggtg tacccgaaaa tcgtatcgac ctttacaccg gttacaccta tacacagacc      360
ctcagcgact ccttgaactt ccgcgttggt gcaggcttgg gctttgagtc ttccaaggac      420
tcgatcaaaa ctaccaaaca caccctccac tcctctcgtc agtcatggtt ggccaaagta      480
cacgccgatc tgttgtccca attgggcaac ggctggtata ttaacccttg gtctgaggtt      540
aaattcgact tgaactctcg ctacaaattg aacacaggcg tcacaaacct gaaaaagac       600
```

```
attaaccaaa aaacaaacgg ctggggcttc ggcttgggcg ccaacattgg caaaaaactg      660
ggcgaaagcg cttccatcga ggccggtccg ttctacaaac aacgtaccta caaagaatcc      720
ggtgaattct ctgtcactac taaatccgga gacgtatctt tgacaatccc taaaacttcc      780
atccgcgagt atggcttgcg cgtcggcatc aaattttga                              819

<210> SEQ ID NO 47
<211> LENGTH: 1095
<212> TYPE: DNA
<213> ORGANISM: Artificial Sequence
<220> FEATURE:
<223> OTHER INFORMATION: Synthetic Nucleic Acid

<400> SEQUENCE: 47
atgtccatga acacttccc gtccaaagtt ttgaccaccg ccatcttggc caccttctgc        60
tccggcgcct tggccgccac ctccgacgac gacgttaaaa aagccgccac cgttgccatc      120
gttgccgcct acaacaacgg ccaagaaatc aacggcttca agccggcga aaccatctac       180 gacatcggcg aagacggcac catcacccaa aaagacgcca ccgccgccga cgttgaagcc      240
gacgacttca aaggcttggg cttgaaaaaa gttgttacca acttgaccaa accgttaac       300 gaaaacaaac aaacgttga cgccaaagtt aaagccgcca atccgaaat cgaaaaattg       360 accaccaaat tggccgacac cgacgccgcc ttggccgaca ccgacgccgc cttggacgaa      420
accaccaacg ccttgaacaa attgggcgaa acatcacca ccttcgccga agaaaccaaa       480
accaacatcg ttaaaatcga cgaaaaattg gaagccgttg ccgacaccgt tgacaaacac      540
gccgaagcct tcaacgacat cgccgactcc ttggacgaaa ccaacaccaa agccgacgaa      600
gccgttaaaa ccgccaacga agccaaacaa accgccgaag aaaccaaaca aaacgttgac      660
gccaaagtta agccgccga aaccgccgcc ggcaaagccg aagccgccgc cggcaccgcc       720
aacaccgccg ccgacaaagc cgaagccgtt gccgccaaag ttaccgacat caaagccgac      780
atcgccacca caaagccga catcgccaaa aactccgccc gcatcgactc cttggacaaa       840
aacgttgcca acttgcgcaa agaaaacccgc caaggcttgg ccgaacaagc cgccttgtcc     900
ggcttgttcc aaccgtacaa cgttggccgc ttcaacgtta ccgccgccgt tggcggctac     960
aaatccgaat ccgccgttgc catcggcacc ggcttccgct tcaccgaaaa cttcgccgcc    1020
aaagccggcg ttgccgttgg cacctcctcc ggctcctccg ccgcctacca cgttggcgtt    1080
aactacgaat ggtaa                                                       1095

<210> SEQ ID NO 48
<211> LENGTH: 1179
<212> TYPE: DNA
<213> ORGANISM: Artificial Sequence
<220> FEATURE:
<223> OTHER INFORMATION: Synthetic Nucleic Acid

<400> SEQUENCE: 48
atgcgcaaaa aattgaccgc cttggttttg tccgccttgc cgttggccgc cgttgccgac       60
gtttccttgt acggcgaaat caaagccggc gttgaaggcc gcaactacca attgcaattg      120
accgaagccc aagccgccaa cggcggcgcc tccggcaag ttaaagttac caaagttacc       180
aaagccaaat cccgcatccg caccaaaatc tccgacttcg gctccttcat cggcttcaaa     240
ggctccgaag acttgggcga cggcttgaaa gccgtttggc aattggaaca agacgttttcc     300 gttgccggcg gcggcgccac ccaatggggc aaccgcgaat ccttcatcgg cttggccggc      360
gaattcggca ccttgcgcgc cggccgcgtt gccaaccaat tcgacgacgc ctcccaagcc      420
```

```
atcgacccgt gggactccaa caacgacgtt gcctcccaat tgggcatctt caaacgccac      480
gacgacatgc cggtttccgt tcgctacgac tccccggaat tctccggctt ctccggctcc      540
gttcaattcg ttccgatcca aaactccaaa tccgcctaca ccccggccta ctacaccaaa      600
aacaccaaca caacttgac cttggttccg gccgttgttg gcaaaccggg ctccgacgtt       660
tactacgccg gcttgaacta caaaaacggc ggcttcgccg gcaactacgc cttcaaatac      720
gcccgccacg ccaacgttgg ccgcaacgcc ttcgaattgt tcttgatcgg ctccggctcc      780
gaccaagcca aaggcaccga cccgttgaaa aaccaccaag ttcaccgctt gaccggcggc      840
tacgaagaag gcggcttgaa cttggccttg gccgcccaat tggacttgtc cgaaaacggc      900
gacaaaacca aaactccac caccgaaatc gccgccaccg cctcctaccg cttcggcaac       960
gccgttccgc gcatctccta cgcccacggc ttcgacttca tcgaacgcgg caaaaaaggc      1020
gaaaacacct cctacgacca aatcatcgcc ggcgttgact acgacttctc caaacgcacc      1080
tccgccatcg tttccggcgc ctggttgaaa cgcaacaccg gcatcggcaa ctacaccccaa     1140 atcaacgccg cctccgttgg cttgcgccac aaattctaa                            1179
```

```
<210> SEQ ID NO 49
<211> LENGTH: 2145
<212> TYPE: DNA
<213> ORGANISM: Artificial Sequence
<220> FEATURE:
<223> OTHER INFORMATION: Synthetic Nucleic Acid

<400> SEQUENCE: 49
```

```
atgaacaccc cgttgttccg cttgtccttg ttgtccttga ccttggccgc cggcttcgcc       60
cacgccgccg aaaacaacgc caaagttgtt ttggacaccg ttaccgttaa aggcgaccgc      120
caaggctcca aaatccgcac caacatcgtt accttgcaac aaaaagacga atccaccgcc      180
accgacatgc gcgaattgtt gaaagaagaa ccgtccatcg acttcggcgg cggcaacggc      240
acctcccaat tcttgacctt gcgcggcatg ggccaaaact ccgttgacat caaagttgac      300
aacgcctact ccgactccca aatcttgtac caccaaggcc gcttcatcgt tgacccggcc      360
ttggttaaag ttgtttccgt tcaaaaaggc gccggctccg cctccgccgg catcggcgcc      420
accaacggcg ccatcatcac caaaaccgtt gacgcccaag acttgttgaa aggcttggac      480
aaaaactggg gcgttcgctt gaactccggc ttcgcctcca cgaaggcgt ttcctacggc       540 gcctccgttt cggcaaaga aggcaacttc gacggcttgt tctcctacaa ccgcaacaac      600
gaaaaagact acgaagccgg caaaggcttc cgcaacaact tcaacggcgg caaaaccgtt      660
ccgtactccg ccttggacaa acgctcctac ttggccaaaa tcggcacctc cttcggcgac      720
ggcgaccacc gcatcgtttt gtcccacatg aaagaccaac accgcggcat ccgcaccgtt      780
cgcgaagaat tcaccgttgg cggcgacaaa gaacgcatct ccatggaacg ccaagccccg      840
gcctaccgcg aaaccaccca atccaacacc aacttggcct acaccggcaa aaacttgggc      900
ttcgttgaaa aattggacgc caacgcctac gttttggaaa agaacgcta ctccgccgac       960 gactccggca ccggctacgc cggcaacgtt aaaggcccga ccacaccca atcaccacc       1020 cgcggcatga acttcaactt cgactcccgc ttggccgaac aaaccttgtt gaaatacggc      1080
atcaactacc gccaccaaga aatcaaaccg caagccttct tgaactccca attcaaaatc      1140
gaagacaaag aaaaagccac cgacgaagaa aaaacaaaa accgcgaaaa cgaaaaaatc       1200
gccaaagcct accgcttgac caacccgacc aaaaccgaca ccggcgccta catcgaagcc      1260
```

```
atccacgaaa tcgacggctt caccttgacc ggcggcttgc gctacgaccg cttcaaagtt    1320
aaaacccacg acggcaaaac cgtttcctcc aacaacttga acccgtcctt cggcgttatc    1380
tggcaaccgc acgaacactg gtccttctcc gcctcccaca actacgcctc ccgctccccg    1440
cgcttgtacg acgccttgca aacccacggc aaacgcggca tcatctccat cgccgacggc    1500
accaaagccg aacgcgcccg caacaccgaa atcggcttca actacaacga cggcaccttc    1560
gccgccaacg gctcctactt ctggcaaacc atcaaagacg ccttggccaa cccgcaaaac    1620
cgccacgact ccgttgccgt cgcgaagcc gttaacgccg gctacatcaa aaaccacggc    1680
tacgaattgg gcgcctccta ccgcaccggc ggcttgaccg ccaaagttgg cgtttcccac    1740
tccaaaccgc gcttctacga cacccacaaa gacaaattgt tgtccgccaa cccggaattc    1800
ggcgcccaag ttggccgcac ctggaccgcc tccttggcct accgcttcca aaacccgaac    1860
ttggaaatcg gctggcgcgg ccgctacgtt caaaaagccg ttggctccat cttggttgcc    1920
ggccaaaaag accgcaacgg caaattggaa aacgttgttc gcaaaggctt cggcgttaac    1980
gacgttttcg ccaactggaa accgttgggc aaagacacct tgaacgttaa cttgtccgtt    2040
aacaacgttt tcaacacctt ctactacccg cactcccaac gctggaccaa caccttgccg    2100
ggcgttggcc gcgacgttcg cttgggcgtt aactacaaat tctaa                  2145

<210> SEQ ID NO 50
<211> LENGTH: 406
<212> TYPE: DNA
<213> ORGANISM: Artificial Sequence
<220> FEATURE:
<223> OTHER INFORMATION: Synthetic Nucleic Acid

<400> SEQUENCE: 50
atttgtcctt tcaggaacag cagattaatt acaggcgcat tctaacacaa ccgccgcgcc      60
ggccgattac cgttaacctg ttcataaact gtacagcaca tatttcaatg taaatctttg     120
ttattttatt gcggtgtaac ttttttacaa cattcttaaa accattccga cctgtctgcc     180
gactttccca atccgcctta ataaatcata caagatactg aaattatatt aatctctata     240
atatttatcc ctatcgaatt tttaacagca aaaccgtttt acaggattta tcaatccgcc     300
cgccagaaaa cttttcattc aaaccttttt cccatctgta cgacattgca atcccttatt     360
ccatagtgca taattacgca aattcagcga tgaatttcca acccgg                   406

<210> SEQ ID NO 51
<211> LENGTH: 223
<212> TYPE: DNA
<213> ORGANISM: Artificial Sequence
<220> FEATURE:
<223> OTHER INFORMATION: Synthetic Nucleic Acid

<400> SEQUENCE: 51
catggatcca cagcaaaacc gttttacagg atttatcaat ccgccgcca gaaaactttt       60 cattcaaacc ttttttcccat ctgtacgaca ttgcaatccc ttattccata gtgcataatt    120
acgcaaattc agcgatgaat ttccaacccg gtttgtagta tggtcgataa agacctatt     180 gtttcaataa tttaaattgg ttctaaaggt tactcatatg cga                       223

<210> SEQ ID NO 52
<211> LENGTH: 160
<212> TYPE: DNA
<213> ORGANISM: Artificial Sequence
<220> FEATURE:
<223> OTHER INFORMATION: Synthetic Nucleic Acid
```

```
<400> SEQUENCE: 52
catggatcca cagcaaaacc gttttacagg atttatcaat ccgcccgcca gaaaactttt      60
cattcaaacc tttttcccat ctgtacgaca ttgcaatccc ttattccata gtgcataatt     120
acgcaaattc agcgatgaat ttccaacccg gcatatgcga                           160

<210> SEQ ID NO 53
<211> LENGTH: 59
<212> TYPE: DNA
<213> ORGANISM: Artificial Sequence
<220> FEATURE:
<223> OTHER INFORMATION: Synthetic Nucleic Acid

<400> SEQUENCE: 53
taaccattgt gaaaatgccg tccgaacacg ataatttacc gttcggacgg cattttgta       59
```